US011957551B2

(12) United States Patent
Rosati et al.

(10) Patent No.: US 11,957,551 B2
(45) Date of Patent: *Apr. 16, 2024

(54) ABSORBENT ARTICLES WITH CHANNELS AND SIGNALS

(71) Applicant: The Procter & Gamble Company, Cincinnati, OH (US)

(72) Inventors: Rodrigo Rosati, Frankfurt am Main (DE); Carsten Heinrich Kreuzer, Hofheim (DE); Hans Adolf Jackels, Mechernich (DE); Blanca Arizti, Frankfurt am Main (DE); Ernesto G. Bianchi, Oberusel (DE); Donald Carroll Roe, West Chester, OH (US); Darrell Ian Brown, Mason, OH (US); Sarah Ann Sanborn, Frankfurt (DE); Theodore Cory Fites, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 30 days.

This patent is subject to a terminal disclaimer.

(21) Appl. No.: 17/527,204

(22) Filed: Nov. 16, 2021

(65) Prior Publication Data
US 2022/0071810 A1    Mar. 10, 2022

Related U.S. Application Data

(63) Continuation of application No. 16/295,012, filed on Mar. 7, 2019, now Pat. No. 11,207,220, which is a
(Continued)

(51) Int. Cl.
*A61F 13/15*    (2006.01)
*A61F 13/45*    (2006.01)
(Continued)

(52) U.S. Cl.
CPC ............ *A61F 13/45* (2013.01); *A61F 13/533* (2013.01); *A61F 13/535* (2013.01);
(Continued)

(58) Field of Classification Search
CPC ...... A61F 13/45; A61F 13/533; A61F 13/535; A61F 13/536; A61F 13/84;
(Continued)

(56) References Cited

U.S. PATENT DOCUMENTS

| 1,733,997 A | 10/1929 | Steven |
| 1,734,499 A | 11/1929 | Davis |

(Continued)

FOREIGN PATENT DOCUMENTS

| CA | 2001370 | 4/1990 |
| CA | 2291997 | 6/2000 |

(Continued)

OTHER PUBLICATIONS

Robert F. Gould American Chemical Society, "American Chemical Society publication entitled Contact Angle, Wettability and Adhesion", Advances in Chemistry Series 43, Chapter 7, edited by Robert F. Gould, dated 1964.

(Continued)

*Primary Examiner* — Jacqueline F Stephens
(74) *Attorney, Agent, or Firm* — Daniel S. Albrecht; Sarah M. DeCristofaro

(57) ABSTRACT

Absorbent articles herein may provide a topsheet, a backsheet, an absorbent core disposed between the topsheet and the backsheet. The absorbent core may comprise at least one channel having a shape. The backsheet graphics may substantially match the shape.

11 Claims, 18 Drawing Sheets

Related U.S. Application Data continuation of application No. 15/354,017, filed on Nov. 17, 2016, now Pat. No. 10,449,097, which is a continuation of application No. 14/077,355, filed on Nov. 12, 2013, now Pat. No. 9,532,910.

(60) Provisional application No. 61/878,206, filed on Sep. 16, 2013.

(51) Int. Cl.

| | |
|---|---|
| *A61F 13/533* | (2006.01) |
| *A61F 13/535* | (2006.01) |
| *A61F 13/536* | (2006.01) |
| *A61F 13/84* | (2006.01) |
| *A61F 13/53* | (2006.01) |
| *A61F 13/532* | (2006.01) |
| *A61F 13/537* | (2006.01) |

(52) U.S. Cl.
CPC ............ *A61F 13/536* (2013.01); *A61F 13/84* (2013.01); *A61F 2013/4587* (2013.01); *A61F 2013/530562* (2013.01); *A61F 13/5323* (2013.01); *A61F 2013/53765* (2013.01); *A61F 2013/53778* (2013.01); *A61F 2013/8497* (2013.01)

(58) Field of Classification Search
CPC .......... A61F 13/5323; A61F 2013/4587; A61F 2013/530562; A61F 2013/53765; A61F 2013/53778; A61F 2013/8497
See application file for complete search history.

(56) References Cited

U.S. PATENT DOCUMENTS

| | | |
|---|---|---|
| 1,989,283 A | 1/1935 | Limacher |
| 2,058,509 A | 10/1936 | David |
| 2,271,676 A | 2/1942 | Elna |
| 2,450,789 A | 10/1948 | Frieman |
| 2,508,811 A | 5/1950 | Best et al. |
| 2,568,910 A | 9/1951 | Condylis |
| 2,570,796 A | 10/1951 | Rose |
| 2,570,963 A | 10/1951 | Mesmer |
| 2,583,553 A | 1/1952 | Faure |
| 2,705,957 A | 4/1955 | Virginia |
| 2,788,003 A | 4/1957 | Norden |
| 2,788,786 A | 4/1957 | Dexter |
| 2,798,489 A | 7/1957 | Mayes |
| 2,807,263 A | 9/1957 | Mae |
| 2,830,589 A | 4/1958 | Doner |
| 2,890,700 A | 6/1959 | Lonberg-holm |
| 2,890,701 A | 6/1959 | Mary |
| 2,898,912 A | 8/1959 | Jane |
| 2,931,361 A | 4/1960 | Alice |
| 2,977,957 A | 4/1961 | Joseph |
| 3,071,138 A | 1/1963 | Gustavo |
| 3,180,335 A | 4/1965 | Duncan et al. |
| 3,207,158 A | 9/1965 | Kazuko et al. |
| 3,227,160 A | 1/1966 | Margaret |
| 3,386,442 A | 6/1968 | Reinhardt |
| 3,561,446 A | 2/1971 | Jones, Sr. |
| 3,572,342 A | 3/1971 | Lindquist |
| 3,572,432 A | 3/1971 | Aulick |
| 3,575,174 A | 4/1971 | Mogor |
| 3,578,155 A | 5/1971 | Small et al. |
| 3,606,887 A | 9/1971 | Roeder |
| 3,610,244 A | 10/1971 | Jones, Sr. |
| 3,618,608 A | 11/1971 | Brink |
| 3,642,001 A | 2/1972 | Sabee |
| 3,653,381 A | 4/1972 | Warnken |
| 3,670,731 A | 6/1972 | Harmon |
| 3,688,767 A | 9/1972 | Goldstein |
| 3,710,797 A | 1/1973 | Marsan |
| 3,731,688 A | 5/1973 | Litt et al. |
| 3,756,878 A | 9/1973 | Willot |
| 3,774,241 A | 11/1973 | Zerkle |
| 3,776,233 A | 12/1973 | Schaar |
| 3,814,100 A | 6/1974 | Nystrand |
| 3,828,784 A | 8/1974 | Zoephel |
| 3,840,418 A | 10/1974 | Sabee |
| 3,847,702 A | 11/1974 | Jones |
| 3,848,594 A | 11/1974 | Buell |
| 3,848,595 A | 11/1974 | Endres |
| 3,848,597 A | 11/1974 | Endres |
| 3,860,003 A | 1/1975 | Buell |
| 3,863,637 A | 2/1975 | Macdonald et al. |
| 3,882,870 A | 5/1975 | Hathaway |
| 3,884,234 A | 5/1975 | Taylor |
| 3,900,032 A | 8/1975 | Heurlen |
| 3,911,173 A | 10/1975 | Sprague, Jr. |
| 3,920,017 A | 11/1975 | Karami |
| 3,924,626 A | 12/1975 | Lee et al. |
| 3,926,189 A | 12/1975 | Taylor |
| 3,929,134 A | 12/1975 | Karami |
| 3,929,135 A | 12/1975 | Thompson |
| 3,930,501 A | 1/1976 | Schaar |
| 3,938,523 A | 2/1976 | Gilliland et al. |
| 3,968,799 A | 7/1976 | Schrading |
| 3,978,861 A | 9/1976 | Schaar |
| 3,981,306 A | 9/1976 | Krusko |
| 3,987,794 A | 10/1976 | Schaar |
| 3,995,637 A | 12/1976 | Schaar |
| 3,995,640 A | 12/1976 | Schaar |
| 3,999,547 A | 12/1976 | Hernandez |
| 4,014,338 A | 3/1977 | Schaar |
| 4,034,760 A | 7/1977 | Amirsakis |
| 4,055,180 A | 10/1977 | Karami |
| 4,074,508 A | 2/1978 | Reid |
| 4,079,739 A | 3/1978 | Whitehead |
| 4,084,592 A | 4/1978 | Tritsch |
| 4,100,922 A | 7/1978 | Hernandez |
| 4,232,674 A | 11/1980 | Melican |
| 4,257,418 A | 3/1981 | Hessner |
| 4,259,220 A | 3/1981 | Bunnelle et al. |
| 4,296,750 A | 10/1981 | Woon et al. |
| 4,315,508 A | 2/1982 | Bolick |
| 4,324,246 A | 4/1982 | Mullane et al. |
| 4,340,706 A | 7/1982 | Obayashi et al. |
| 4,341,216 A | 7/1982 | Obenour |
| 4,342,314 A | 8/1982 | Radel et al. |
| 4,360,021 A | 11/1982 | Stima |
| 4,381,783 A | 5/1983 | Elias |
| 4,388,075 A | 6/1983 | Mesek et al. |
| 4,410,571 A | 10/1983 | Korpman |
| 4,461,621 A | 7/1984 | Karami et al. |
| 4,463,045 A | 7/1984 | Ahr |
| 4,469,710 A | 9/1984 | Rielley et al. |
| 4,475,912 A | 10/1984 | Coates |
| 4,490,148 A | 12/1984 | Beckestrom |
| 4,507,438 A | 3/1985 | Obayashi et al. |
| 4,515,595 A | 5/1985 | Kievit |
| 4,527,990 A | 7/1985 | Sigl |
| 4,541,871 A | 9/1985 | Obayashi et al. |
| 4,551,191 A | 11/1985 | Kock et al. |
| 4,573,986 A | 3/1986 | Minetola |
| 4,578,072 A | 3/1986 | Lancaster |
| 4,578,702 A | 3/1986 | Campbell, III |
| 4,585,448 A | 4/1986 | Enloe |
| 4,585,450 A | 4/1986 | Rosch et al. |
| 4,589,878 A | 5/1986 | Mitrani |
| 4,596,568 A | 6/1986 | Flug |
| 4,601,717 A | 7/1986 | Blevins |
| 4,606,964 A | 8/1986 | Wideman |
| 4,609,518 A | 9/1986 | Curro et al. |
| 4,610,678 A | 9/1986 | Weisman |
| 4,623,342 A | 11/1986 | Ito et al. |
| 4,624,666 A | 11/1986 | Derossett et al. |
| 4,629,643 A | 12/1986 | Curro |
| 4,636,207 A | 1/1987 | Buell |
| 4,641,381 A | 2/1987 | Heran et al. |
| 4,646,510 A | 3/1987 | Mcintyre |
| 4,662,875 A | 5/1987 | Hirotsu |
| 4,666,983 A | 5/1987 | Tsubakimoto et al. |

(56) References Cited

U.S. PATENT DOCUMENTS

| | | |
|---|---|---|
| 4,670,011 A | 6/1987 | Mesek |
| 4,670,012 A | 6/1987 | Johnson |
| 4,680,030 A | 7/1987 | Coates et al. |
| 4,681,579 A | 7/1987 | Toussant et al. |
| 4,681,581 A | 7/1987 | Coates |
| 4,681,793 A | 7/1987 | Linman et al. |
| 4,690,680 A | 9/1987 | Higgins |
| 4,695,278 A | 9/1987 | Lawson |
| 4,699,622 A | 10/1987 | Toussant |
| 4,704,115 A | 11/1987 | Buell |
| 4,704,116 A | 11/1987 | Enloe |
| 4,710,189 A | 12/1987 | Lash |
| 4,720,321 A | 1/1988 | Smith |
| 4,731,066 A | 3/1988 | Korpman |
| 4,731,070 A | 3/1988 | Koci |
| 4,741,941 A | 5/1988 | Englebert |
| 4,747,846 A | 5/1988 | Boland et al. |
| 4,753,648 A | 6/1988 | Jackson |
| 4,773,905 A | 9/1988 | Molee et al. |
| 4,784,892 A | 11/1988 | Storey et al. |
| 4,785,996 A | 11/1988 | Ziecker |
| 4,787,896 A | 11/1988 | Houghton et al. |
| 4,795,454 A | 1/1989 | Dragoo |
| 4,800,102 A | 1/1989 | Takada |
| 4,802,884 A | 2/1989 | Froeidh |
| 4,806,408 A | 2/1989 | Sa |
| 4,806,598 A | 2/1989 | Morman |
| 4,808,176 A | 2/1989 | Kielpikowski |
| 4,808,178 A | 2/1989 | Aziz |
| 4,826,880 A | 5/1989 | Lesniak |
| 4,834,735 A | 5/1989 | Alemany |
| 4,834,740 A | 5/1989 | Suzuki et al. |
| 4,834,742 A | 5/1989 | Wilson et al. |
| 4,838,886 A | 6/1989 | Kent |
| 4,842,666 A | 6/1989 | Werenicz |
| 4,846,815 A | 7/1989 | Scripps |
| 4,846,825 A | 7/1989 | Enloe et al. |
| 4,848,815 A | 7/1989 | Molloy |
| 4,861,652 A | 8/1989 | Lippert et al. |
| 4,869,724 A | 9/1989 | Scripps |
| 4,886,697 A | 12/1989 | Perdelwitz, Jr. et al. |
| 4,888,231 A | 12/1989 | Angstadt |
| 4,892,528 A | 1/1990 | Suzuki |
| 4,892,535 A | 1/1990 | Bjoernberg et al. |
| 4,892,536 A | 1/1990 | Desmarais |
| 4,894,060 A | 1/1990 | Nestegard |
| 4,894,277 A | 1/1990 | Akasaki |
| 4,900,317 A | 2/1990 | Buell |
| 4,904,251 A | 2/1990 | Igaue et al. |
| 4,909,802 A | 3/1990 | Ahr et al. |
| 4,909,803 A | 3/1990 | Aziz |
| 4,936,839 A | 6/1990 | Molee et al. |
| 4,940,463 A | 7/1990 | Leathers et al. |
| 4,940,464 A | 7/1990 | Van Gompel |
| 4,946,527 A | 8/1990 | Battrell |
| 4,950,264 A | 8/1990 | Osborn, III |
| 4,960,477 A | 10/1990 | Mesek |
| 4,963,140 A | 10/1990 | Robertson |
| 4,966,809 A | 10/1990 | Tanaka et al. |
| 4,968,313 A | 11/1990 | Sabee |
| 4,990,147 A | 2/1991 | Freeland |
| 4,994,053 A | 2/1991 | Lang |
| 5,006,394 A | 4/1991 | Baird |
| 5,019,063 A | 5/1991 | Marsan et al. |
| 5,019,072 A | 5/1991 | Polski |
| 5,021,051 A | 6/1991 | Hiuke |
| 5,030,314 A | 7/1991 | Lang |
| 5,032,120 A | 7/1991 | Freeland et al. |
| 5,034,008 A | 7/1991 | Breitkopf |
| 5,037,416 A | 8/1991 | Allen |
| 5,071,414 A | 12/1991 | Elliott |
| 5,072,687 A | 12/1991 | Mitchell et al. |
| 5,085,654 A | 2/1992 | Buell |
| 5,087,255 A | 2/1992 | Sims |
| 5,092,861 A | 3/1992 | Nomura |
| 5,102,597 A | 4/1992 | Berg et al. |
| 5,114,420 A | 5/1992 | Igaue et al. |
| 5,124,188 A | 6/1992 | Roe et al. |
| 5,135,522 A | 8/1992 | Fahrenkrug et al. |
| 5,137,537 A | 8/1992 | Herron |
| D329,697 S | 9/1992 | Fahrenkrug et al. |
| 5,143,679 A | 9/1992 | Weber |
| 5,147,343 A | 9/1992 | Kellenberger |
| 5,147,345 A | 9/1992 | Lavon |
| 5,149,334 A | 9/1992 | Berg et al. |
| 5,149,335 A | 9/1992 | Kellenberger |
| 5,151,091 A | 9/1992 | Glaug et al. |
| 5,151,092 A | 9/1992 | Buell |
| 5,156,793 A | 10/1992 | Buell |
| 5,167,653 A | 12/1992 | Igaue et al. |
| 5,167,897 A | 12/1992 | Weber |
| 5,175,046 A | 12/1992 | Nguyen |
| 5,180,622 A | 1/1993 | Lahrman et al. |
| 5,190,563 A | 3/1993 | Herron et al. |
| 5,190,606 A | 3/1993 | Merkatoris et al. |
| 5,204,997 A | 4/1993 | Suzuki et al. |
| 5,213,817 A | 5/1993 | Pelley |
| 5,221,274 A | 6/1993 | Buell |
| 5,235,515 A | 8/1993 | Ungpiyakul et al. |
| 5,242,436 A | 9/1993 | Weil |
| 5,246,431 A | 9/1993 | Minetola et al. |
| 5,246,432 A | 9/1993 | Suzuki et al. |
| 5,246,433 A | 9/1993 | Hasse |
| 5,248,309 A | 9/1993 | Serbiak |
| 5,260,345 A | 11/1993 | Desmarais |
| 5,269,775 A | 12/1993 | Freeland |
| 5,281,683 A | 1/1994 | Yano et al. |
| H1298 H | 4/1994 | Ahr et al. |
| 5,300,565 A | 4/1994 | Berg et al. |
| 5,312,386 A | 5/1994 | Correa et al. |
| 5,331,059 A | 7/1994 | Engelhardt et al. |
| 5,336,552 A | 8/1994 | Strack et al. |
| 5,348,547 A | 9/1994 | Payne et al. |
| 5,358,500 A | 10/1994 | Lavon et al. |
| 5,366,782 A | 11/1994 | Curro et al. |
| 5,382,610 A | 1/1995 | Harada et al. |
| 5,387,207 A | 2/1995 | Dyer |
| 5,387,208 A | 2/1995 | Ashton |
| 5,387,209 A | 2/1995 | Yamamoto et al. |
| 5,389,095 A | 2/1995 | Suzuki et al. |
| 5,397,316 A | 3/1995 | Young |
| 5,397,317 A | 3/1995 | Thomas |
| 5,399,175 A | 3/1995 | Glaug et al. |
| 5,401,792 A | 3/1995 | Babu et al. |
| 5,409,771 A | 4/1995 | Dahmen et al. |
| H1440 H | 5/1995 | New et al. |
| 5,411,497 A | 5/1995 | Tanzer |
| 5,415,644 A | 5/1995 | Enloe |
| 5,425,725 A | 6/1995 | Tanzer |
| 5,429,630 A | 7/1995 | Beal et al. |
| 5,433,715 A | 7/1995 | Tanzer |
| 5,451,219 A | 9/1995 | Suzuki et al. |
| 5,451,442 A | 9/1995 | Pieniak et al. |
| 5,460,622 A | 10/1995 | Dragoo et al. |
| 5,460,623 A | 10/1995 | Emenaker et al. |
| 5,462,541 A | 10/1995 | Bruemmer et al. |
| 5,476,458 A | 12/1995 | Glaug et al. |
| 5,486,166 A | 1/1996 | Bishop et al. |
| 5,486,167 A | 1/1996 | Dragoo et al. |
| 5,490,846 A | 2/1996 | Ellis et al. |
| 5,492,962 A | 2/1996 | Lahrman et al. |
| 5,494,622 A | 2/1996 | Heath et al. |
| 5,499,978 A | 3/1996 | Buell |
| 5,507,736 A | 4/1996 | Clear |
| 5,507,895 A | 4/1996 | Suekane |
| 5,509,915 A | 4/1996 | Hanson |
| 5,514,104 A | 5/1996 | Cole et al. |
| 5,518,801 A | 5/1996 | Chappell |
| 5,520,674 A | 5/1996 | Lavon et al. |
| 5,522,810 A | 6/1996 | Allen, Jr. et al. |
| 5,527,300 A | 6/1996 | Sauer |
| 5,531,730 A | 7/1996 | Dreier |
| 5,532,323 A | 7/1996 | Yano et al. |
| 5,542,943 A | 8/1996 | Sageser |

(56) References Cited

U.S. PATENT DOCUMENTS

| | | |
|---|---|---|
| 5,549,592 A | 8/1996 | Fries et al. |
| 5,549,593 A | 8/1996 | Ygge et al. |
| 5,549,791 A | 8/1996 | Herron et al. |
| 5,554,145 A | 9/1996 | Roe |
| 5,559,335 A | 9/1996 | Zeng et al. |
| 5,560,878 A | 10/1996 | Dragoo et al. |
| 5,562,634 A | 10/1996 | Flumene et al. |
| 5,562,646 A | 10/1996 | Goldman |
| 5,569,234 A | 10/1996 | Buell |
| 5,571,096 A | 11/1996 | Dobrin |
| 5,574,121 A | 11/1996 | Irie et al. |
| 5,575,783 A | 11/1996 | Clear |
| 5,580,411 A | 12/1996 | Nease |
| 5,584,829 A | 12/1996 | Lavash et al. |
| 5,586,979 A | 12/1996 | Thomas |
| 5,591,152 A | 1/1997 | Buell |
| 5,591,155 A | 1/1997 | Nishikawa |
| 5,593,399 A | 1/1997 | Tanzer |
| 5,599,335 A | 2/1997 | Goldman |
| 5,601,542 A | 2/1997 | Melius |
| 5,607,414 A | 3/1997 | Richards |
| 5,607,416 A | 3/1997 | Yamamoto et al. |
| 5,607,537 A | 3/1997 | Johnson et al. |
| 5,607,760 A | 3/1997 | Roe |
| 5,609,587 A | 3/1997 | Roe |
| 5,609,588 A | 3/1997 | Dipalma et al. |
| 5,611,879 A | 3/1997 | Morman |
| 5,613,959 A | 3/1997 | Roessler et al. |
| 5,613,960 A | 3/1997 | Mizutani |
| 5,614,283 A | 3/1997 | Potnis et al. |
| 5,622,589 A | 4/1997 | Johnson et al. |
| 5,624,423 A | 4/1997 | Anjur et al. |
| 5,624,424 A | 4/1997 | Saisaka et al. |
| 5,625,222 A | 4/1997 | Yoneda |
| 5,626,571 A | 5/1997 | Young et al. |
| 5,628,741 A | 5/1997 | Buell et al. |
| 5,628,845 A | 5/1997 | Murray et al. |
| 5,635,191 A | 6/1997 | Roe |
| 5,635,271 A | 6/1997 | Zafiroglu |
| 5,637,106 A | 6/1997 | Mitchell et al. |
| 5,643,238 A | 7/1997 | Baker |
| 5,643,243 A | 7/1997 | Klemp |
| 5,643,588 A | 7/1997 | Roe |
| 5,649,914 A | 7/1997 | Glaug et al. |
| 5,650,214 A | 7/1997 | Anderson et al. |
| H1674 H | 8/1997 | Ames et al. |
| 5,658,268 A | 8/1997 | Johns et al. |
| 5,662,634 A | 9/1997 | Yamamoto et al. |
| 5,662,638 A | 9/1997 | Johnson et al. |
| 5,662,758 A | 9/1997 | Hamilton et al. |
| 5,669,894 A | 9/1997 | Goldman |
| 5,674,215 A | 10/1997 | Roennberg |
| 5,681,300 A | 10/1997 | Ahr |
| 5,683,374 A | 11/1997 | Yamamoto et al. |
| 5,685,874 A | 11/1997 | Buell et al. |
| 5,690,624 A | 11/1997 | Sasaki et al. |
| 5,690,627 A | 11/1997 | Clear et al. |
| 5,691,035 A | 11/1997 | Chappell et al. |
| 5,691,036 A | 11/1997 | Lin et al. |
| 5,695,488 A | 12/1997 | Sosalla |
| 5,700,254 A | 12/1997 | Mcdowall |
| 5,702,376 A | 12/1997 | Glaug et al. |
| 5,714,156 A | 2/1998 | Schmidt et al. |
| 5,723,087 A | 3/1998 | Chappell et al. |
| 5,733,275 A | 3/1998 | Davis et al. |
| 5,749,866 A | 5/1998 | Roe et al. |
| 5,752,947 A | 5/1998 | Awolin |
| 5,756,039 A | 5/1998 | Mcfall |
| H1732 H | 6/1998 | Johnson |
| 5,762,641 A | 6/1998 | Bewick-sonntag |
| 5,766,388 A | 6/1998 | Pelley et al. |
| 5,766,389 A | 6/1998 | Brandon et al. |
| 5,772,825 A | 6/1998 | Schmitz |
| 5,776,121 A | 7/1998 | Roe et al. |
| 5,779,831 A | 7/1998 | Schmitz |
| 5,788,684 A | 8/1998 | Abuto et al. |
| 5,795,345 A | 8/1998 | Mizutani et al. |
| 5,797,892 A | 8/1998 | Glaug |
| 5,797,894 A | 8/1998 | Cadieux et al. |
| 5,807,365 A | 9/1998 | Luceri |
| 5,810,796 A | 9/1998 | Kimura |
| 5,810,800 A | 9/1998 | Hunter et al. |
| 5,814,035 A | 9/1998 | Gryskiewicz et al. |
| 5,820,618 A | 10/1998 | Roberts et al. |
| 5,827,257 A | 10/1998 | Fujioka et al. |
| 5,830,202 A | 11/1998 | Bogdanski et al. |
| 5,833,678 A | 11/1998 | Ashton et al. |
| 5,837,789 A | 11/1998 | Stockhausen et al. |
| 5,840,404 A | 11/1998 | Graff |
| 5,843,059 A | 12/1998 | Niemeyer et al. |
| 5,846,231 A | 12/1998 | Fujioka et al. |
| 5,846,232 A | 12/1998 | Serbiak et al. |
| 5,849,816 A | 12/1998 | Suskind et al. |
| 5,851,204 A | 12/1998 | Mizutani |
| 5,855,572 A | 1/1999 | Schmidt |
| 5,858,013 A | 1/1999 | Kling |
| 5,858,515 A | 1/1999 | Stokes et al. |
| 5,865,823 A | 2/1999 | Curro |
| 5,865,824 A | 2/1999 | Chen et al. |
| 5,873,868 A | 2/1999 | Nakahata |
| 5,876,391 A | 3/1999 | Roe et al. |
| 5,879,751 A | 3/1999 | Bogdanski |
| 5,891,118 A | 4/1999 | Toyoshima et al. |
| 5,891,544 A | 4/1999 | Chappell et al. |
| 5,897,545 A | 4/1999 | Kline |
| 5,904,673 A | 5/1999 | Roe et al. |
| 5,925,439 A | 7/1999 | Haubach |
| 5,928,184 A | 7/1999 | Etheredge et al. |
| 5,931,825 A | 8/1999 | Kuen et al. |
| 5,938,648 A | 8/1999 | Beck |
| 5,938,650 A | 8/1999 | Baer et al. |
| 5,941,862 A | 8/1999 | Haynes et al. |
| 5,944,706 A | 8/1999 | Palumbo et al. |
| 5,947,949 A | 9/1999 | Inoue et al. |
| 5,951,536 A | 9/1999 | Osborn, III et al. |
| 5,957,908 A | 9/1999 | Kline |
| 5,968,025 A | 10/1999 | Roe |
| 5,968,029 A | 10/1999 | Chappell et al. |
| 5,980,500 A | 11/1999 | Shimizu et al. |
| 5,981,824 A | 11/1999 | Luceri |
| 5,989,236 A | 11/1999 | Roe et al. |
| 6,004,306 A | 12/1999 | Robles |
| 6,022,430 A | 2/2000 | Blenke et al. |
| 6,022,431 A | 2/2000 | Blenke et al. |
| 6,042,673 A | 3/2000 | Johnson et al. |
| 6,050,984 A | 4/2000 | Fujioka |
| 6,054,631 A | 4/2000 | Gent |
| 6,056,732 A | 5/2000 | Fujioka et al. |
| 6,060,115 A | 5/2000 | Borowski et al. |
| 6,068,620 A | 5/2000 | Chmielewski |
| 6,080,909 A | 6/2000 | Oesterdahl et al. |
| 6,083,210 A | 7/2000 | Young et al. |
| 6,090,994 A | 7/2000 | Chen |
| 6,091,336 A | 7/2000 | Zand et al. |
| 6,093,474 A | 7/2000 | Sironi |
| 6,099,515 A | 8/2000 | Sugito |
| 6,102,892 A | 8/2000 | Putzer et al. |
| 6,103,814 A | 8/2000 | Vandrongelen et al. |
| 6,107,537 A | 8/2000 | Elder |
| 6,110,157 A | 8/2000 | Schmidt |
| 6,117,121 A | 9/2000 | Faulks et al. |
| 6,117,803 A | 9/2000 | Morman et al. |
| 6,120,486 A | 9/2000 | Toyoda et al. |
| 6,120,487 A | 9/2000 | Ashton |
| 6,120,489 A | 9/2000 | Johnson |
| 6,120,866 A | 9/2000 | Arakawa et al. |
| 6,121,509 A | 9/2000 | Ashraf et al. |
| 6,129,717 A | 10/2000 | Fujioka et al. |
| 6,129,720 A | 10/2000 | Blenke et al. |
| 6,132,411 A | 10/2000 | Huber et al. |
| 6,139,912 A | 10/2000 | Onuschak et al. |
| 6,143,821 A | 11/2000 | Houben |
| 6,152,908 A | 11/2000 | Widlund et al. |
| 6,156,023 A | 12/2000 | Yoshioka |

(56) References Cited

U.S. PATENT DOCUMENTS

| | | |
|---|---|---|
| 6,156,424 A | 12/2000 | Taylor |
| 6,160,197 A | 12/2000 | Lassen et al. |
| 6,165,160 A | 12/2000 | Suzuki |
| 6,174,302 B1 | 1/2001 | Kumasaka |
| 6,177,606 B1 | 1/2001 | Etheredge et al. |
| 6,177,607 B1 | 1/2001 | Blaney et al. |
| 6,186,996 B1 | 2/2001 | Martin |
| 6,210,386 B1 | 4/2001 | Inoue |
| 6,210,390 B1 | 4/2001 | Karlsson |
| 6,231,556 B1 | 5/2001 | Osborn, III |
| 6,231,566 B1 | 5/2001 | Lai |
| 6,238,380 B1 | 5/2001 | Sasaki |
| 6,241,716 B1 | 6/2001 | Roennberg |
| 6,254,294 B1 | 7/2001 | Muhar |
| 6,258,996 B1 | 7/2001 | Goldman |
| 6,265,488 B1 | 7/2001 | Nagasuna et al. |
| 6,290,686 B1 | 9/2001 | Tanzer |
| 6,306,122 B1 | 10/2001 | Narawa et al. |
| 6,307,119 B1 | 10/2001 | Cammarota |
| 6,315,765 B1 | 11/2001 | Datta et al. |
| 6,319,239 B1 | 11/2001 | Daniels |
| 6,322,552 B1 | 11/2001 | Blenke et al. |
| 6,325,787 B1 | 12/2001 | Roe et al. |
| 6,326,525 B1 | 12/2001 | Hamajima et al. |
| 6,330,735 B1 | 12/2001 | Hahn et al. |
| 6,334,858 B1 | 1/2002 | Ronnberg et al. |
| 6,336,922 B1 | 1/2002 | Vangompel et al. |
| 6,340,611 B1 | 1/2002 | Shimizu et al. |
| 6,342,715 B1 | 1/2002 | Shimizu et al. |
| 6,350,332 B1 | 2/2002 | Thomas et al. |
| 6,368,687 B1 | 4/2002 | Joseph et al. |
| 6,371,948 B1 | 4/2002 | Mizutani |
| 6,372,952 B1 | 4/2002 | Lash et al. |
| 6,375,644 B2 | 4/2002 | Mizutani |
| 6,376,034 B1 | 4/2002 | Brander |
| 6,383,431 B1 | 5/2002 | Dobrin |
| 6,383,960 B1 | 5/2002 | Everett et al. |
| 6,394,989 B2 | 5/2002 | Mizutani |
| 6,402,729 B1 | 6/2002 | Boberg et al. |
| 6,402,731 B1 | 6/2002 | Suprise et al. |
| 6,403,857 B1 | 6/2002 | Gross et al. |
| 6,406,467 B1 | 6/2002 | Dilnik et al. |
| 6,409,883 B1 | 6/2002 | Makolin |
| 6,410,820 B1 | 6/2002 | Mcfall et al. |
| 6,410,822 B1 | 6/2002 | Mizutani |
| 6,413,248 B1 | 7/2002 | Mizutani |
| 6,413,249 B1 | 7/2002 | Turi et al. |
| 6,414,214 B1 | 7/2002 | Engelhardt et al. |
| 6,416,502 B1 | 7/2002 | Connelly et al. |
| 6,416,697 B1 | 7/2002 | Venturino et al. |
| 6,419,667 B1 | 7/2002 | Avalon et al. |
| 6,423,046 B1 | 7/2002 | Fujioka et al. |
| 6,423,048 B1 | 7/2002 | Suzuki et al. |
| 6,423,884 B1 | 7/2002 | Oehmen |
| 6,429,350 B1 | 8/2002 | Tanzer et al. |
| 6,432,094 B1 | 8/2002 | Fujioka et al. |
| 6,432,098 B1 | 8/2002 | Kline |
| 6,432,099 B2 | 8/2002 | Roennberg |
| 6,437,214 B1 | 8/2002 | Everett et al. |
| 6,441,268 B1 | 8/2002 | Edwardsson |
| 6,443,933 B1 | 9/2002 | Suzuki et al. |
| 6,444,064 B1 | 9/2002 | Henry |
| 6,447,496 B1 | 9/2002 | Mizutani |
| 6,458,111 B1 | 10/2002 | Onishi et al. |
| 6,458,877 B1 | 10/2002 | Ahmed et al. |
| 6,459,016 B1 | 10/2002 | Rosenfeld et al. |
| 6,461,034 B1 | 10/2002 | Cleveland |
| 6,461,342 B2 | 10/2002 | Tanji et al. |
| 6,461,343 B1 | 10/2002 | Schaefer et al. |
| 6,472,478 B1 | 10/2002 | Funk |
| 6,475,201 B2 | 11/2002 | Saito et al. |
| 6,492,574 B1 | 12/2002 | Chen et al. |
| 6,494,872 B1 | 12/2002 | Suzuki et al. |
| 6,494,873 B2 | 12/2002 | Karlsson et al. |
| 6,500,159 B1 | 12/2002 | Carvalho |
| 6,503,233 B1 | 1/2003 | Chen |
| 6,503,979 B1 | 1/2003 | Funk et al. |
| 6,506,186 B1 | 1/2003 | Roessler et al. |
| 6,506,961 B1 | 1/2003 | Levy |
| 6,515,195 B1 | 2/2003 | Lariviere et al. |
| 6,517,525 B1 | 2/2003 | Berthou et al. |
| 6,518,479 B1 | 2/2003 | Graef et al. |
| 6,520,947 B1 | 2/2003 | Tilly et al. |
| 6,521,811 B1 | 2/2003 | Lassen et al. |
| 6,521,812 B1 | 2/2003 | Graef et al. |
| 6,524,294 B1 | 2/2003 | Hilston et al. |
| 6,525,240 B1 | 2/2003 | Graef et al. |
| 6,528,698 B2 | 3/2003 | Mizutani et al. |
| 6,529,860 B1 | 3/2003 | Strumolo et al. |
| 6,531,025 B1 | 3/2003 | Lender et al. |
| 6,531,027 B1 | 3/2003 | Lender et al. |
| 6,534,149 B1 | 3/2003 | Daley et al. |
| 6,559,081 B1 | 5/2003 | Erspamer et al. |
| 6,559,239 B1 | 5/2003 | Riegel et al. |
| 6,562,168 B1 | 5/2003 | Schmitt et al. |
| 6,562,192 B1 | 5/2003 | Hamilton |
| 6,563,013 B1 | 5/2003 | Murota |
| 6,569,137 B2 | 5/2003 | Suzuki et al. |
| 6,573,422 B1 | 6/2003 | Rosenfeld et al. |
| 6,585,713 B1 | 7/2003 | Lemahieu et al. |
| 6,585,858 B1 | 7/2003 | Otto et al. |
| 6,602,234 B2 | 8/2003 | Klemp et al. |
| 6,605,070 B2 | 8/2003 | Ludwig et al. |
| 6,605,172 B1 | 8/2003 | Anderson et al. |
| 6,605,752 B2 | 8/2003 | Magnusson et al. |
| 6,610,900 B1 | 8/2003 | Tanzer |
| 6,630,054 B1 | 10/2003 | Graef et al. |
| 6,632,209 B1 | 10/2003 | Chmielewski |
| 6,632,504 B1 | 10/2003 | Gillespie |
| 6,645,569 B2 | 11/2003 | Cramer |
| 6,646,180 B1 | 11/2003 | Chmielewski |
| 6,648,869 B1 | 11/2003 | Gillies et al. |
| 6,648,870 B2 | 11/2003 | Itoh et al. |
| 6,648,871 B2 | 11/2003 | Kusibojoska et al. |
| 6,649,807 B2 | 11/2003 | Mizutani |
| 6,649,810 B1 | 11/2003 | Minato et al. |
| 6,657,015 B1 | 12/2003 | Riegel et al. |
| 6,657,102 B2 | 12/2003 | Furuya et al. |
| 6,667,424 B1 | 12/2003 | Hamilton |
| 6,670,522 B1 | 12/2003 | Graef et al. |
| 6,673,982 B1 | 1/2004 | Chen |
| 6,673,983 B1 | 1/2004 | Graef et al. |
| 6,673,985 B1 | 1/2004 | Mizutani et al. |
| 6,682,515 B1 | 1/2004 | Mizutani et al. |
| 6,682,516 B2 | 1/2004 | Johnston et al. |
| 6,689,115 B1 | 2/2004 | Coenen et al. |
| 6,689,934 B2 | 2/2004 | Dodge, II et al. |
| 6,695,827 B2 | 2/2004 | Chen |
| 6,700,034 B1 | 3/2004 | Lindsay et al. |
| 6,703,538 B2 | 3/2004 | Lassen et al. |
| 6,705,465 B2 | 3/2004 | Ling et al. |
| 6,706,129 B2 | 3/2004 | Ando et al. |
| 6,706,943 B2 | 3/2004 | Onishi et al. |
| 6,710,224 B2 | 3/2004 | Chmielewski et al. |
| 6,710,225 B1 | 3/2004 | Everett et al. |
| 6,716,205 B2 | 4/2004 | Coenen et al. |
| 6,716,441 B1 | 4/2004 | Osborne et al. |
| 6,717,029 B2 | 4/2004 | Baker |
| 6,726,668 B2 | 4/2004 | Underhill et al. |
| 6,726,792 B1 | 4/2004 | Johnson et al. |
| 6,730,387 B2 | 5/2004 | Rezai et al. |
| 6,734,335 B2 | 5/2004 | Graef et al. |
| 6,746,976 B1 | 6/2004 | Urankar et al. |
| 6,790,798 B1 | 9/2004 | Suzuki |
| 6,802,834 B2 | 10/2004 | Melius et al. |
| 6,809,158 B2 | 10/2004 | Ikeuchi et al. |
| 6,811,642 B2 | 11/2004 | Ochi |
| 6,818,083 B2 | 11/2004 | Mcamish et al. |
| 6,818,166 B2 | 11/2004 | Edwardson et al. |
| 6,830,800 B2 | 12/2004 | Curro et al. |
| 6,832,905 B2 | 12/2004 | Delzer et al. |
| 6,840,929 B2 | 1/2005 | Kurata |
| 6,846,374 B2 | 1/2005 | Coenen et al. |
| 6,858,771 B2 | 2/2005 | Yoshimasa et al. |

(56) References Cited

U.S. PATENT DOCUMENTS

| | | |
|---|---|---|
| 6,863,933 B2 | 3/2005 | Cramer |
| 6,863,960 B2 | 3/2005 | Curro et al. |
| 6,867,345 B2 | 3/2005 | Shimoe et al. |
| 6,867,346 B1 | 3/2005 | Dopps et al. |
| 6,878,433 B2 | 4/2005 | Curro |
| 6,878,647 B1 | 4/2005 | Rezai |
| 6,880,211 B2 | 4/2005 | Jackson et al. |
| 6,891,080 B2 | 5/2005 | Minato et al. |
| 6,904,865 B2 | 6/2005 | Klofta et al. |
| 6,911,574 B1 | 6/2005 | Mizutani |
| 6,923,797 B2 | 8/2005 | Shinohara et al. |
| 6,923,926 B2 | 8/2005 | Walter et al. |
| 6,926,703 B2 | 8/2005 | Sugito et al. |
| 6,929,629 B2 | 8/2005 | Drevik et al. |
| 6,939,914 B2 | 9/2005 | Qin et al. |
| 6,946,585 B2 | 9/2005 | London |
| 6,953,451 B2 | 10/2005 | Berba et al. |
| 6,955,733 B2 | 10/2005 | Miller |
| 6,962,578 B1 | 11/2005 | Lavon |
| 6,962,645 B2 | 11/2005 | Graef et al. |
| 6,965,058 B1 | 11/2005 | Raidel |
| 6,969,781 B2 | 11/2005 | Graef et al. |
| 6,972,010 B2 | 12/2005 | Pesce et al. |
| 6,972,011 B2 | 12/2005 | Mori |
| 6,979,564 B2 | 12/2005 | Glucksmann et al. |
| 6,982,052 B2 | 1/2006 | Daniels et al. |
| 7,001,167 B2 | 2/2006 | Venturino et al. |
| 7,014,632 B2 | 3/2006 | Takino et al. |
| 7,015,370 B2 | 3/2006 | Watanabe et al. |
| 7,037,299 B2 | 5/2006 | Turi et al. |
| 7,037,571 B2 | 5/2006 | Fish et al. |
| 7,048,726 B2 | 5/2006 | Kusagawa et al. |
| 7,056,311 B2 | 6/2006 | Kinoshita et al. |
| 7,067,711 B2 | 6/2006 | Kuroda et al. |
| 7,073,373 B2 | 7/2006 | La Fortune |
| 7,078,583 B2 | 7/2006 | Kudo et al. |
| 7,090,665 B2 | 8/2006 | Ohashi et al. |
| 7,108,759 B2 | 9/2006 | You et al. |
| 7,108,916 B2 | 9/2006 | Ehrnsperger |
| 7,112,621 B2 | 9/2006 | Rohrbaugh |
| 7,122,713 B2 | 10/2006 | Komatsu et al. |
| 7,125,470 B2 | 10/2006 | Graef et al. |
| 7,132,585 B2 | 11/2006 | Kudo et al. |
| 7,147,628 B2 | 12/2006 | Drevik |
| 7,150,729 B2 | 12/2006 | Shimada et al. |
| 7,154,019 B2 | 12/2006 | Mishima et al. |
| 7,160,281 B2 | 1/2007 | Leminh et al. |
| 7,163,528 B2 | 1/2007 | Christon |
| 7,166,190 B2 | 1/2007 | Graef et al. |
| 7,169,136 B2 | 1/2007 | Otsubo et al. |
| 7,183,360 B2 | 2/2007 | Daniel et al. |
| 7,189,888 B2 | 3/2007 | Wang et al. |
| 7,196,241 B2 | 3/2007 | Kinoshita et al. |
| 7,199,211 B2 | 4/2007 | Popp et al. |
| 7,204,830 B2 | 4/2007 | Mishima et al. |
| 7,207,978 B2 | 4/2007 | Takino et al. |
| 7,219,403 B2 | 5/2007 | Miyamoto et al. |
| 7,220,251 B2 | 5/2007 | Otsubo et al. |
| 7,241,280 B2 | 7/2007 | Christon et al. |
| 7,250,481 B2 | 7/2007 | Jaworek et al. |
| 7,252,657 B2 | 8/2007 | Mishima et al. |
| 7,265,258 B2 | 9/2007 | Hamilton |
| 7,270,651 B2 | 9/2007 | Adams |
| 7,285,178 B2 | 10/2007 | Mischler |
| 7,306,582 B2 | 12/2007 | Adams |
| 7,311,696 B2 | 12/2007 | Christon et al. |
| 7,311,968 B2 | 12/2007 | Ehrnsperger et al. |
| 7,312,372 B2 | 12/2007 | Miyama et al. |
| 7,318,820 B2 | 1/2008 | Lavon et al. |
| 7,329,244 B2 | 2/2008 | Otsubo et al. |
| 7,329,246 B2 | 2/2008 | Kinoshita et al. |
| 7,335,810 B2 | 2/2008 | Yoshimasa et al. |
| 7,377,914 B2 | 5/2008 | Lavon |
| 7,429,689 B2 | 9/2008 | Chen |
| 7,435,244 B2 | 10/2008 | Schroer, Jr. et al. |
| 7,465,373 B2 | 12/2008 | Graef et al. |
| 7,500,969 B2 | 3/2009 | Mishima et al. |
| 7,504,552 B2 | 3/2009 | Tamura et al. |
| 7,521,109 B2 | 4/2009 | Suzuki et al. |
| 7,521,587 B2 | 4/2009 | Busam et al. |
| 7,537,832 B2 | 5/2009 | Carlucci et al. |
| 7,547,815 B2 | 6/2009 | Ohashi et al. |
| 7,550,646 B2 | 6/2009 | Tamura et al. |
| 7,563,257 B2 | 7/2009 | Nakajima et al. |
| 7,588,561 B2 | 9/2009 | Kenmochi et al. |
| 7,594,904 B2 | 9/2009 | Rosenfeld et al. |
| 7,598,428 B2 | 10/2009 | Gustavsson et al. |
| 7,625,363 B2 | 12/2009 | Yoshimasa et al. |
| 7,641,642 B2 | 1/2010 | Murai et al. |
| 7,648,490 B2 | 1/2010 | Kuroda et al. |
| 7,652,111 B2 | 1/2010 | Hermeling et al. |
| 7,666,173 B2 | 2/2010 | Mishima et al. |
| 7,666,174 B2 | 2/2010 | Onishi et al. |
| 7,686,790 B2 | 3/2010 | Rasmussen et al. |
| 7,687,596 B2 | 3/2010 | Hermeling et al. |
| 7,695,461 B2 | 4/2010 | Rosenfeld et al. |
| 7,696,402 B2 | 4/2010 | Nishikawa et al. |
| 7,708,725 B2 | 5/2010 | Tamagawa et al. |
| 7,717,150 B2 | 5/2010 | Manabe et al. |
| 7,718,844 B2 | 5/2010 | Olson |
| 7,722,587 B2 | 5/2010 | Suzuki et al. |
| 7,722,590 B2 | 5/2010 | Tsuji et al. |
| 7,727,217 B2 | 6/2010 | Hancock-cooke |
| 7,736,351 B2 | 6/2010 | Nigam et al. |
| 7,737,324 B2 | 6/2010 | Lavon et al. |
| 7,744,576 B2 | 6/2010 | Busam |
| 7,744,578 B2 | 6/2010 | Tanio et al. |
| 7,750,203 B2 | 7/2010 | Becker et al. |
| 7,754,822 B2 | 7/2010 | Daniel et al. |
| 7,754,940 B2 | 7/2010 | Brisebois et al. |
| 7,759,540 B2 | 7/2010 | Litvay et al. |
| 7,763,004 B2 | 7/2010 | Lavon |
| 7,767,875 B2 | 8/2010 | Olson et al. |
| 7,767,876 B2 | 8/2010 | Davis et al. |
| 7,767,878 B2 | 8/2010 | Suzuki |
| 7,772,420 B2 | 8/2010 | Hermeling et al. |
| 7,786,341 B2 | 8/2010 | Schneider et al. |
| 7,795,492 B2 | 9/2010 | Vartiainen |
| 7,803,145 B2 | 9/2010 | Rosenfeld et al. |
| 7,825,291 B2 | 11/2010 | Elfsberg et al. |
| 7,838,722 B2 | 11/2010 | Blessing et al. |
| 7,850,672 B2 | 12/2010 | Guidotti et al. |
| 7,851,667 B2 | 12/2010 | Becker et al. |
| 7,855,314 B2 | 12/2010 | Hanao et al. |
| 7,857,797 B2 | 12/2010 | Kudo et al. |
| 7,858,842 B2 | 12/2010 | Komatsu et al. |
| 7,884,259 B2 | 2/2011 | Hanao et al. |
| 7,888,549 B2 | 2/2011 | Jansson et al. |
| 7,910,797 B2 | 3/2011 | Nandrea et al. |
| 7,931,636 B2 | 4/2011 | Lavon et al. |
| 7,935,207 B2 | 5/2011 | Zhao et al. |
| 7,935,861 B2 | 5/2011 | Suzuki |
| 7,938,813 B2 | 5/2011 | Wang et al. |
| 7,942,858 B2 | 5/2011 | Francoeur et al. |
| 7,951,126 B2 | 5/2011 | Nanjyo et al. |
| 7,959,620 B2 | 6/2011 | Miura et al. |
| 7,982,091 B2 | 7/2011 | Konawa |
| 7,993,319 B2 | 8/2011 | Sperl |
| 8,017,827 B2 | 9/2011 | Hundorf et al. |
| 8,029,486 B2 | 10/2011 | Nakajima et al. |
| 8,030,536 B2 | 10/2011 | Ponomarenko et al. |
| 8,034,991 B2 | 10/2011 | Bruzadin et al. |
| 8,039,684 B2 | 10/2011 | Guidotti et al. |
| 8,052,454 B2 | 11/2011 | Polnyi |
| 8,057,620 B2 | 11/2011 | Perego et al. |
| 8,109,915 B2 | 2/2012 | Shimoe et al. |
| 8,124,828 B2 | 2/2012 | Kline et al. |
| 8,133,212 B2 | 3/2012 | Takada |
| 8,148,598 B2 | 4/2012 | Tsang et al. |
| 8,163,124 B2 | 4/2012 | Moriura et al. |
| 8,167,862 B2 | 5/2012 | Digiacomantonio et al. |
| 8,173,858 B2 | 5/2012 | Kuroda et al. |
| 8,178,747 B2 | 5/2012 | Venturino et al. |
| 8,183,430 B2 | 5/2012 | Haakansson et al. |

(56) References Cited

U.S. PATENT DOCUMENTS

| | | |
|---|---|---|
| 8,186,296 B2 | 5/2012 | Brown |
| 8,187,239 B2 | 5/2012 | Lavon |
| 8,187,240 B2 | 5/2012 | Busam et al. |
| 8,198,506 B2 | 6/2012 | Venturino et al. |
| 8,211,815 B2 | 7/2012 | Baker et al. |
| 8,236,715 B2 | 8/2012 | Schmidt et al. |
| 8,237,012 B2 | 8/2012 | Miyama et al. |
| 8,246,594 B2 | 8/2012 | Sperl et al. |
| 8,258,367 B2 | 9/2012 | Lawson et al. |
| 8,268,424 B1 | 9/2012 | Suzuki et al. |
| 8,273,943 B2 | 9/2012 | Noda et al. |
| 8,282,617 B2 | 10/2012 | Kaneda |
| 8,283,516 B2 | 10/2012 | Litvay |
| 8,317,766 B2 | 11/2012 | Naoto et al. |
| 8,317,768 B2 | 11/2012 | Larsson |
| 8,319,005 B2 | 11/2012 | Becker et al. |
| 8,343,123 B2 | 1/2013 | Noda et al. |
| 8,343,296 B2 | 1/2013 | Blessing et al. |
| 8,360,977 B2 | 1/2013 | Marttila et al. |
| 8,361,047 B2 | 1/2013 | Mukai et al. |
| 8,377,025 B2 | 2/2013 | Nakajima et al. |
| 8,388,590 B2 | 3/2013 | Mason, Jr. et al. |
| 8,450,555 B2 | 5/2013 | Nhan et al. |
| 8,496,637 B2 | 7/2013 | Hundorf et al. |
| 8,519,213 B2 | 8/2013 | Venturino et al. |
| 8,524,355 B2 | 9/2013 | Nakaoka |
| 8,552,252 B2 | 10/2013 | Hundorf et al. |
| 8,568,566 B2 | 10/2013 | Jackels et al. |
| 8,569,571 B2 | 10/2013 | Kline et al. |
| 8,581,019 B2 | 11/2013 | Carlucci et al. |
| 8,603,058 B2 | 12/2013 | Sperl et al. |
| 8,604,270 B2 | 12/2013 | Venturino et al. |
| 8,633,347 B2 | 1/2014 | Bianco et al. |
| 8,664,468 B2 | 3/2014 | Lawson et al. |
| 8,674,170 B2 | 3/2014 | Busam et al. |
| 8,734,417 B2 | 5/2014 | Lavon et al. |
| 8,766,031 B2 | 7/2014 | Becker et al. |
| 8,772,570 B2 | 7/2014 | Kawakami et al. |
| 8,784,594 B2 | 7/2014 | Blessing et al. |
| 8,785,715 B2 | 7/2014 | Wright et al. |
| 8,791,318 B2 | 7/2014 | Becker et al. |
| 8,936,584 B2 | 1/2015 | Zander et al. |
| 9,056,034 B2 | 6/2015 | Akiyama |
| 9,289,330 B2 | 3/2016 | Mason, Jr. et al. |
| 9,326,896 B2 | 5/2016 | Schäfer et al. |
| 9,375,358 B2 | 6/2016 | Ehmsperger et al. |
| 9,532,910 B2 | 1/2017 | Rosati et al. |
| 2001/0007065 A1 | 7/2001 | Blanchard et al. |
| 2001/0008964 A1 | 7/2001 | Kurata et al. |
| 2001/0016548 A1 | 8/2001 | Kugler et al. |
| 2001/0020157 A1 | 9/2001 | Mizutani et al. |
| 2001/0037101 A1 | 11/2001 | Allan et al. |
| 2001/0044610 A1 | 11/2001 | Kim et al. |
| 2002/0007167 A1 | 1/2002 | Dan et al. |
| 2002/0007169 A1 | 1/2002 | Graef |
| 2002/0016122 A1 | 2/2002 | Curro |
| 2002/0016579 A1 | 2/2002 | Stenberg |
| 2002/0045881 A1 | 4/2002 | Kusibojoska et al. |
| 2002/0056516 A1 | 5/2002 | Ochi |
| 2002/0058919 A1 | 5/2002 | Hamilton et al. |
| 2002/0062112 A1 | 5/2002 | Mizutani |
| 2002/0062115 A1 | 5/2002 | Wada et al. |
| 2002/0062116 A1 | 5/2002 | Mizutani et al. |
| 2002/0065498 A1 | 5/2002 | Ohashi et al. |
| 2002/0072471 A1 | 6/2002 | Ikeuchi et al. |
| 2002/0082575 A1 | 6/2002 | Dan et al. |
| 2002/0087139 A1 | 7/2002 | Coenen et al. |
| 2002/0095127 A1 | 7/2002 | Fish et al. |
| 2002/0102392 A1 | 8/2002 | Fish et al. |
| 2002/0115969 A1 | 8/2002 | Mori et al. |
| 2002/0123728 A1 | 9/2002 | Graef et al. |
| 2002/0123848 A1 | 9/2002 | Schneiderman et al. |
| 2002/0151634 A1 | 10/2002 | Rohrbaugh et al. |
| 2002/0151861 A1 | 10/2002 | Klemp et al. |
| 2002/0173767 A1 | 11/2002 | Coenen |
| 2002/0192366 A1 | 12/2002 | Cramer et al. |
| 2002/0197695 A1 | 12/2002 | Glucksmann et al. |
| 2003/0036741 A1 | 2/2003 | Abba et al. |
| 2003/0078553 A1 | 4/2003 | Wada |
| 2003/0084983 A1 | 5/2003 | Rangachari et al. |
| 2003/0088223 A1 | 5/2003 | Vogt et al. |
| 2003/0105190 A1 | 6/2003 | Diehl |
| 2003/0109839 A1 | 6/2003 | Costea |
| 2003/0114811 A1 | 6/2003 | Christon |
| 2003/0114816 A1 | 6/2003 | Underhill et al. |
| 2003/0114818 A1 | 6/2003 | Benecke |
| 2003/0115969 A1 | 6/2003 | Koyano |
| 2003/0120235 A1 | 6/2003 | Boulanger |
| 2003/0120249 A1 | 6/2003 | Wulz et al. |
| 2003/0135176 A1 | 7/2003 | Delzer et al. |
| 2003/0135181 A1 | 7/2003 | Chen |
| 2003/0135182 A1 | 7/2003 | Woon |
| 2003/0139712 A1 | 7/2003 | Dodge et al. |
| 2003/0139715 A1 | 7/2003 | Dodge et al. |
| 2003/0139718 A1 | 7/2003 | Graef et al. |
| 2003/0144642 A1 | 7/2003 | Dopps et al. |
| 2003/0144644 A1 | 7/2003 | Murai |
| 2003/0148684 A1 | 8/2003 | Cramer et al. |
| 2003/0148694 A1 | 8/2003 | Ghiam |
| 2003/0158530 A1 | 8/2003 | Diehl et al. |
| 2003/0158531 A1 | 8/2003 | Chmielewski |
| 2003/0158532 A1 | 8/2003 | Magee |
| 2003/0167045 A1 | 9/2003 | Graef et al. |
| 2003/0171727 A1 | 9/2003 | Graef et al. |
| 2003/0208175 A1 | 11/2003 | Gross et al. |
| 2003/0225385 A1 | 12/2003 | Glaug et al. |
| 2003/0233082 A1 | 12/2003 | Kline |
| 2003/0236512 A1 | 12/2003 | Baker |
| 2004/0019338 A1 | 1/2004 | Litvay et al. |
| 2004/0022998 A1 | 2/2004 | Miyamoto et al. |
| 2004/0033750 A1 | 2/2004 | Everett et al. |
| 2004/0063367 A1 | 4/2004 | Dodge et al. |
| 2004/0064113 A1 | 4/2004 | Erdman |
| 2004/0064115 A1 | 4/2004 | Arora et al. |
| 2004/0064116 A1 | 4/2004 | Arora et al. |
| 2004/0064125 A1 | 4/2004 | Justmann et al. |
| 2004/0065420 A1 | 4/2004 | Graef et al. |
| 2004/0082928 A1 | 4/2004 | Pesce et al. |
| 2004/0097895 A1 | 5/2004 | Busam |
| 2004/0122411 A1 | 6/2004 | Hancock-cooke |
| 2004/0127131 A1 | 7/2004 | Potnis |
| 2004/0127871 A1 | 7/2004 | Odorzynski et al. |
| 2004/0127872 A1 | 7/2004 | Petryk |
| 2004/0134596 A1 | 7/2004 | Rosati et al. |
| 2004/0138633 A1 | 7/2004 | Mishima et al. |
| 2004/0147890 A1 | 7/2004 | Nakahata et al. |
| 2004/0158212 A1 | 8/2004 | Ponomarenko |
| 2004/0162536 A1 | 8/2004 | Becker |
| 2004/0167486 A1 | 8/2004 | Busam |
| 2004/0167489 A1 | 8/2004 | Kellenberger et al. |
| 2004/0170813 A1 | 9/2004 | Digiacomantonio |
| 2004/0193127 A1 | 9/2004 | Hansson et al. |
| 2004/0215160 A1 | 10/2004 | Chmielewski et al. |
| 2004/0220541 A1 | 11/2004 | Suzuki et al. |
| 2004/0225271 A1 | 11/2004 | Datta et al. |
| 2004/0231065 A1 | 11/2004 | Daniel et al. |
| 2004/0236299 A1 | 11/2004 | Tsang et al. |
| 2004/0236455 A1 | 11/2004 | Woltman et al. |
| 2004/0249355 A1 | 12/2004 | Tanio |
| 2004/0260259 A1 | 12/2004 | Baker |
| 2004/0265544 A1 | 12/2004 | Di Salvo et al. |
| 2005/0001929 A1 | 1/2005 | Ochial et al. |
| 2005/0004543 A1 | 1/2005 | Schroer et al. |
| 2005/0004548 A1 | 1/2005 | Otsubo et al. |
| 2005/0008839 A1 | 1/2005 | Cramer |
| 2005/0018258 A1 | 1/2005 | Miyagi et al. |
| 2005/0038401 A1 | 2/2005 | Suzuki et al. |
| 2005/0070867 A1 | 3/2005 | Beruda et al. |
| 2005/0085784 A1 | 4/2005 | Leminh et al. |
| 2005/0090789 A1 | 4/2005 | Graef et al. |
| 2005/0101929 A1 | 5/2005 | Waksmundzki et al. |
| 2005/0148258 A1 | 7/2005 | Chakravarty et al. |
| 2005/0148961 A1 | 7/2005 | Sosalla |
| 2005/0148990 A1 | 7/2005 | Shimoe et al. |

(56) References Cited

U.S. PATENT DOCUMENTS

| | | |
|---|---|---|
| 2005/0154363 A1 | 7/2005 | Minato et al. |
| 2005/0159720 A1 | 7/2005 | Gentilcore |
| 2005/0165208 A1 | 7/2005 | Popp et al. |
| 2005/0171499 A1 | 8/2005 | Nigam et al. |
| 2005/0176910 A1 | 8/2005 | Jaworek et al. |
| 2005/0203475 A1 | 9/2005 | Lavon et al. |
| 2005/0215752 A1 | 9/2005 | Popp et al. |
| 2005/0217791 A1 | 10/2005 | Costello |
| 2005/0229543 A1 | 10/2005 | Tippey |
| 2005/0234414 A1 | 10/2005 | Liu |
| 2005/0245684 A1 | 11/2005 | Daniel et al. |
| 2005/0288645 A1 | 12/2005 | Lavon |
| 2005/0288646 A1 | 12/2005 | Lavon |
| 2006/0004334 A1 | 1/2006 | Schlinz et al. |
| 2006/0021695 A1 | 2/2006 | Blessing |
| 2006/0024433 A1 | 2/2006 | Blessing |
| 2006/0069367 A1 | 3/2006 | Waksmundzki et al. |
| 2006/0069371 A1 | 3/2006 | Ohashi |
| 2006/0073969 A1 | 4/2006 | Torii et al. |
| 2006/0081348 A1 | 4/2006 | Graef et al. |
| 2006/0129114 A1 | 6/2006 | Mason et al. |
| 2006/0142724 A1 | 6/2006 | Watanabe et al. |
| 2006/0155057 A1 | 7/2006 | Hermeling et al. |
| 2006/0155254 A1 | 7/2006 | Sanz et al. |
| 2006/0167215 A1 | 7/2006 | Hermeling et al. |
| 2006/0177647 A1 | 8/2006 | Schmidt |
| 2006/0178071 A1 | 8/2006 | Schmidt et al. |
| 2006/0184146 A1 | 8/2006 | Suzuki |
| 2006/0184149 A1 | 8/2006 | Kasai et al. |
| 2006/0189954 A1 | 8/2006 | Kudo |
| 2006/0202380 A1 | 9/2006 | Bentley et al. |
| 2006/0206091 A1 | 9/2006 | Cole et al. |
| 2006/0211828 A1 | 9/2006 | Daniel et al. |
| 2006/0240229 A1 | 10/2006 | Ehrnsperger et al. |
| 2006/0264860 A1 | 11/2006 | Lavon |
| 2006/0264861 A1 | 11/2006 | Lavon et al. |
| 2006/0271010 A1 | 11/2006 | Lavon |
| 2007/0027436 A1 | 2/2007 | Nakagawa et al. |
| 2007/0043191 A1 | 2/2007 | Hermeling et al. |
| 2007/0043330 A1 | 2/2007 | Lankhof |
| 2007/0044903 A1 | 3/2007 | Wisneski et al. |
| 2007/0049892 A1 | 3/2007 | Lord et al. |
| 2007/0049897 A1 | 3/2007 | Lavon et al. |
| 2007/0073253 A1 | 3/2007 | Miyama et al. |
| 2007/0078422 A1 | 4/2007 | Glaug et al. |
| 2007/0088308 A1 | 4/2007 | Ehrnsperger et al. |
| 2007/0093164 A1 | 4/2007 | Nakaoka |
| 2007/0093767 A1 | 4/2007 | Carlucci et al. |
| 2007/0100307 A1 | 5/2007 | Nomoto et al. |
| 2007/0118087 A1 | 5/2007 | Flohr |
| 2007/0123834 A1 | 5/2007 | Mcdowall et al. |
| 2007/0156108 A1 | 7/2007 | Becker et al. |
| 2007/0167928 A1 | 7/2007 | Becker et al. |
| 2007/0179464 A1 | 8/2007 | Becker et al. |
| 2007/0179469 A1 | 8/2007 | Takahashi et al. |
| 2007/0191798 A1 | 8/2007 | Glaug et al. |
| 2007/0219521 A1 | 9/2007 | Hird |
| 2007/0219523 A1 | 9/2007 | Bruun et al. |
| 2007/0239125 A9 | 10/2007 | Erdman et al. |
| 2007/0244455 A1 | 10/2007 | Hansson et al. |
| 2007/0246147 A1 | 10/2007 | Venturino et al. |
| 2007/0255245 A1 | 11/2007 | Asp et al. |
| 2007/0282288 A1 | 12/2007 | Noda et al. |
| 2007/0282290 A1 | 12/2007 | Cole et al. |
| 2007/0282291 A1 | 12/2007 | Cole et al. |
| 2008/0027402 A1 | 1/2008 | Schmidt et al. |
| 2008/0032035 A1 | 2/2008 | Schmidt et al. |
| 2008/0091159 A1 | 4/2008 | Carlucci et al. |
| 2008/0119810 A1 | 5/2008 | Kuroda et al. |
| 2008/0125735 A1 | 5/2008 | Busam |
| 2008/0132864 A1 | 6/2008 | Lawson et al. |
| 2008/0208154 A1 | 8/2008 | Oetjen |
| 2008/0221538 A1 | 9/2008 | Zhao |
| 2008/0221539 A1 | 9/2008 | Zhao |
| 2008/0228158 A1 | 9/2008 | Sue et al. |
| 2008/0262459 A1 | 10/2008 | Kamoto et al. |
| 2008/0268194 A1 | 10/2008 | Kim et al. |
| 2008/0274227 A1 | 11/2008 | Boatman et al. |
| 2008/0281287 A1 | 11/2008 | Marcelo et al. |
| 2008/0294139 A1* | 11/2008 | Ecker ............... A61F 13/51401 604/385.01 |
| 2008/0312617 A1 | 12/2008 | Hundorf |
| 2008/0312618 A1 | 12/2008 | Hundorf et al. |
| 2008/0312619 A1 | 12/2008 | Ashton et al. |
| 2008/0312620 A1 | 12/2008 | Ashton et al. |
| 2008/0312621 A1 | 12/2008 | Hundorf et al. |
| 2008/0312622 A1 | 12/2008 | Hundorf |
| 2008/0312623 A1 | 12/2008 | Hundorf et al. |
| 2008/0312624 A1 | 12/2008 | Hundorf |
| 2008/0312625 A1 | 12/2008 | Hundorf et al. |
| 2008/0312627 A1 | 12/2008 | Takeuchi et al. |
| 2008/0312628 A1 | 12/2008 | Hundorf et al. |
| 2009/0056867 A1 | 3/2009 | Moriura et al. |
| 2009/0058994 A1 | 3/2009 | Kao et al. |
| 2009/0062760 A1 | 3/2009 | Wright et al. |
| 2009/0112173 A1 | 4/2009 | Bissah et al. |
| 2009/0112175 A1 | 4/2009 | Bissah et al. |
| 2009/0157022 A1 | 6/2009 | Macdonald et al. |
| 2009/0192035 A1 | 7/2009 | Stueven et al. |
| 2009/0240220 A1 | 9/2009 | Macdonald et al. |
| 2009/0247977 A1 | 10/2009 | Takeuchi |
| 2009/0258994 A1 | 10/2009 | Stueven et al. |
| 2009/0270825 A1 | 10/2009 | Wciorka et al. |
| 2009/0298963 A1 | 12/2009 | Matsumoto et al. |
| 2009/0299312 A1 | 12/2009 | Macdonald et al. |
| 2009/0306618 A1 | 12/2009 | Kudo et al. |
| 2009/0318884 A1 | 12/2009 | Meyer et al. |
| 2009/0326494 A1 | 12/2009 | Uchida et al. |
| 2010/0051166 A1 | 3/2010 | Hundorf |
| 2010/0062165 A1 | 3/2010 | Suzuki et al. |
| 2010/0062934 A1 | 3/2010 | Suzuki et al. |
| 2010/0063470 A1 | 3/2010 | Suzuki et al. |
| 2010/0068520 A1 | 3/2010 | Stueven |
| 2010/0100065 A1 | 4/2010 | De Angelis et al. |
| 2010/0115237 A1 | 5/2010 | Brewer et al. |
| 2010/0121296 A1 | 5/2010 | Noda et al. |
| 2010/0137773 A1 | 6/2010 | Gross et al. |
| 2010/0137823 A1 | 6/2010 | Corneliusson et al. |
| 2010/0147722 A1 | 6/2010 | Datta |
| 2010/0198179 A1 | 8/2010 | Noda et al. |
| 2010/0228210 A1 | 9/2010 | Busam |
| 2010/0241096 A1 | 9/2010 | Lavon et al. |
| 2010/0241097 A1 | 9/2010 | Nigam et al. |
| 2010/0262099 A1 | 10/2010 | Klofta |
| 2010/0262104 A1 | 10/2010 | Carlucci et al. |
| 2010/0274208 A1 | 10/2010 | Gabrielii et al. |
| 2010/0274210 A1 | 10/2010 | Noda et al. |
| 2010/0312208 A1 | 12/2010 | Bond et al. |
| 2010/0324521 A1 | 12/2010 | Mukai et al. |
| 2010/0324523 A1 | 12/2010 | Mukai et al. |
| 2011/0041999 A1 | 2/2011 | Hundorf et al. |
| 2011/0060301 A1* | 3/2011 | Nishikawa .......... A61F 13/4756 156/220 |
| 2011/0060303 A1 | 3/2011 | Bissah et al. |
| 2011/0066127 A1 | 3/2011 | Kuwano et al. |
| 2011/0071486 A1 | 3/2011 | Harada et al. |
| 2011/0092944 A1 | 4/2011 | Sagisaka et al. |
| 2011/0112498 A1 | 5/2011 | Nhan et al. |
| 2011/0125120 A1 | 5/2011 | Nishitani et al. |
| 2011/0130732 A1 | 6/2011 | Jackels et al. |
| 2011/0130737 A1 | 6/2011 | Sagisaka et al. |
| 2011/0137276 A1 | 6/2011 | Yoshikawa |
| 2011/0144602 A1 | 6/2011 | Long |
| 2011/0144604 A1 | 6/2011 | Noda et al. |
| 2011/0144606 A1 | 6/2011 | Nandrea et al. |
| 2011/0152813 A1 | 6/2011 | Ellingson |
| 2011/0166540 A1 | 7/2011 | Yang |
| 2011/0172630 A1 | 7/2011 | Nomoto et al. |
| 2011/0174430 A1 | 7/2011 | Zhao et al. |
| 2011/0196330 A1 | 8/2011 | Hammons |
| 2011/0208147 A1 | 8/2011 | Kawakami et al. |
| 2011/0250413 A1 | 10/2011 | Lu |
| 2011/0268932 A1 | 11/2011 | Catalan |
| 2011/0274834 A1 | 11/2011 | Brown et al. |

(56) References Cited

U.S. PATENT DOCUMENTS

| | | |
|---|---|---|
| 2011/0288513 A1 | 11/2011 | Hundorf et al. |
| 2011/0288514 A1 | 11/2011 | Kuroda et al. |
| 2011/0295222 A1 | 12/2011 | Becker et al. |
| 2011/0319846 A1 | 12/2011 | Rinnert et al. |
| 2011/0319848 A1 | 12/2011 | Mckiernan |
| 2011/0319851 A1 | 12/2011 | Kudo et al. |
| 2012/0004633 A1 | 1/2012 | Marcelo |
| 2012/0010581 A1* | 1/2012 | Mason, Jr. .......... A61F 13/5514 604/367 |
| 2012/0016326 A1 | 1/2012 | Brennan et al. |
| 2012/0022479 A1 | 1/2012 | Cotton |
| 2012/0035566 A1 | 2/2012 | Sagisaka et al. |
| 2012/0035576 A1 | 2/2012 | Ichikawa et al. |
| 2012/0064792 A1 | 3/2012 | Bauduin |
| 2012/0071848 A1 | 3/2012 | Zhang et al. |
| 2012/0165771 A1 | 6/2012 | Ruman et al. |
| 2012/0165776 A1 | 6/2012 | Mcgregor |
| 2012/0170779 A1 | 7/2012 | Hildebrandt |
| 2012/0175056 A1 | 7/2012 | Tsang et al. |
| 2012/0184934 A1 | 7/2012 | Venturino et al. |
| 2012/0220972 A1 | 8/2012 | Kawamura et al. |
| 2012/0232514 A1 | 9/2012 | Baker et al. |
| 2012/0238977 A1 | 9/2012 | Oku et al. |
| 2012/0253306 A1 | 10/2012 | Otsubo et al. |
| 2012/0256750 A1 | 10/2012 | Novak |
| 2012/0271262 A1 | 10/2012 | Venturino et al. |
| 2012/0312491 A1 | 12/2012 | Jackels |
| 2012/0316046 A1 | 12/2012 | Jackels et al. |
| 2012/0316523 A1 | 12/2012 | Hippe |
| 2012/0316526 A1 | 12/2012 | Rosati et al. |
| 2012/0316527 A1 | 12/2012 | Rosati et al. |
| 2012/0316528 A1 | 12/2012 | Kreuzer et al. |
| 2012/0316529 A1 | 12/2012 | Kreuzer et al. |
| 2012/0323195 A1 | 12/2012 | Ehrnsperger et al. |
| 2012/0323201 A1 | 12/2012 | Bissah et al. |
| 2012/0323202 A1 | 12/2012 | Bissah et al. |
| 2013/0035656 A1 | 2/2013 | Moriya et al. |
| 2013/0041334 A1 | 2/2013 | Prioleau et al. |
| 2013/0178811 A1 | 7/2013 | Kikuchi et al. |
| 2013/0211354 A1 | 8/2013 | Tsuji et al. |
| 2013/0211358 A1 | 8/2013 | Kikkawa et al. |
| 2013/0218115 A1 | 8/2013 | Katsuragawa et al. |
| 2013/0226119 A1 | 8/2013 | Katsuragawa et al. |
| 2013/0226120 A1 | 8/2013 | Van De Maele |
| 2013/0310784 A1 | 11/2013 | Bryant |
| 2014/0005622 A1 | 1/2014 | Wirtz |
| 2014/0005623 A1 | 1/2014 | Wirtz et al. |
| 2014/0027066 A1 | 1/2014 | Jackels et al. |
| 2014/0039437 A1 | 2/2014 | Van De Maele |
| 2014/0102183 A1 | 4/2014 | Agami et al. |
| 2014/0121623 A1 | 5/2014 | Kirby |
| 2014/0135726 A1 | 5/2014 | Busam et al. |
| 2014/0142531 A1 | 5/2014 | Sasayama et al. |
| 2014/0163500 A1 | 6/2014 | Roe et al. |
| 2014/0163501 A1 | 6/2014 | Ehmsperger et al. |
| 2014/0163502 A1 | 6/2014 | Arizti |
| 2014/0163503 A1 | 6/2014 | Arizti |
| 2014/0163506 A1 | 6/2014 | Roe |
| 2014/0163511 A1 | 6/2014 | Roe et al. |
| 2014/0171893 A1 | 6/2014 | Lawson et al. |
| 2014/0318694 A1 | 10/2014 | Blessing et al. |
| 2014/0324007 A1 | 10/2014 | Hundorf et al. |
| 2014/0324008 A1 | 10/2014 | Hundorf et al. |
| 2015/0065975 A1 | 3/2015 | Roe |
| 2015/0065981 A1 | 3/2015 | Roe |
| 2015/0065986 A1 | 3/2015 | Blessing et al. |
| 2015/0073366 A1 | 3/2015 | Ehrnsperger et al. |
| 2015/0080837 A1 | 3/2015 | Rosati et al. |
| 2015/0080839 A1 | 3/2015 | Trapp et al. |
| 2015/0173967 A1 | 6/2015 | Kreuzer |
| 2015/0173968 A1 | 6/2015 | Joseph |
| 2015/0250662 A1 | 9/2015 | Isele et al. |
| 2017/0020739 A1 | 1/2017 | Mason, Jr. et al. |
| 2017/0020745 A1 | 1/2017 | Mason, Jr. et al. |
| 2017/0065465 A1 | 3/2017 | Rosati et al. |
| 2017/0081862 A1 | 3/2017 | Güçbilmez |
| 2019/0201251 A1 | 7/2019 | Rosati et al. |

FOREIGN PATENT DOCUMENTS

| | | |
|---|---|---|
| CA | 2308961 | 11/2000 |
| CA | 2487027 | 12/2003 |
| CA | 2561521 | 3/2007 |
| CA | 2630713 | 11/2008 |
| CA | 2636673 | 1/2009 |
| CA | 2702001 | 10/2010 |
| CA | 2712563 A1 | 3/2011 |
| CN | 1238171 A | 12/1999 |
| CN | 2362468 Y | 2/2000 |
| CN | 1371671 A | 10/2002 |
| CN | 2527254 Y | 12/2002 |
| CN | 2535020 Y | 2/2003 |
| CN | 2548609 Y | 5/2003 |
| CN | 1539391 A | 10/2004 |
| CN | 1939242 | 4/2007 |
| CN | 101292930 | 10/2008 |
| CN | 101422405 A | 5/2009 |
| CN | 201263750 Y | 7/2009 |
| CN | 201591689 U | 9/2010 |
| CN | 201855366 U | 6/2011 |
| DE | 3205931 C2 | 8/1985 |
| DE | 3608114 A1 | 9/1987 |
| DE | 19732499 | 2/1999 |
| DE | 10204937 A1 | 8/2003 |
| EP | 083022 | 7/1983 |
| EP | 149880 A2 | 7/1985 |
| EP | 0149880 A2 | 7/1985 |
| EP | 0203289 A2 | 12/1986 |
| EP | 0206208 A1 | 12/1986 |
| EP | 0209561 A1 | 1/1987 |
| EP | 297411 | 1/1989 |
| EP | 374542 | 6/1990 |
| EP | 0403832 A1 | 12/1990 |
| EP | 481322 | 4/1992 |
| EP | 530438 A1 | 3/1993 |
| EP | 547847 | 6/1993 |
| EP | 555346 | 8/1993 |
| EP | 559476 A1 | 9/1993 |
| EP | 304957 B2 | 4/1994 |
| EP | 591647 | 4/1994 |
| EP | 597273 | 5/1994 |
| EP | 601610 | 6/1994 |
| EP | 632068 A1 | 1/1995 |
| EP | 0640330 A1 | 3/1995 |
| EP | 0668066 | 9/1995 |
| EP | 685214 | 12/1995 |
| EP | 687453 | 12/1995 |
| EP | 0689817 A2 | 1/1996 |
| EP | 0691133 | 1/1996 |
| EP | 0700673 A1 | 3/1996 |
| EP | 0394274 | 7/1996 |
| EP | 394274 B2 | 7/1996 |
| EP | 0724418 A1 | 8/1996 |
| EP | 0725613 A1 | 8/1996 |
| EP | 725615 | 8/1996 |
| EP | 758543 | 2/1997 |
| EP | 0761194 | 3/1997 |
| EP | 769284 | 4/1997 |
| EP | 0781537 A1 | 7/1997 |
| EP | 783877 | 7/1997 |
| EP | 787472 | 8/1997 |
| EP | 788874 | 8/1997 |
| EP | 799004 | 10/1997 |
| EP | 822794 | 2/1998 |
| EP | 826351 | 3/1998 |
| EP | 844861 | 6/1998 |
| EP | 0737055 | 8/1998 |
| EP | 863733 | 9/1998 |
| EP | 971751 | 9/1998 |
| EP | 875224 | 11/1998 |
| EP | 0875224 A1 | 11/1998 |
| EP | 880955 | 12/1998 |
| EP | 891758 | 1/1999 |

(56) References Cited

FOREIGN PATENT DOCUMENTS

| | | |
|---|---|---|
| EP | 0893115 | 1/1999 |
| EP | 724418 B1 | 3/1999 |
| EP | 725613 B1 | 3/1999 |
| EP | 725616 B1 | 3/1999 |
| EP | 0725616 B1 | 3/1999 |
| EP | 904755 | 3/1999 |
| EP | 916327 | 5/1999 |
| EP | 0916327 A1 | 5/1999 |
| EP | 925769 | 6/1999 |
| EP | 933074 | 8/1999 |
| EP | 937736 A2 | 8/1999 |
| EP | 941157 | 9/1999 |
| EP | 947549 | 10/1999 |
| EP | 951887 | 10/1999 |
| EP | 0951890 | 10/1999 |
| EP | 2295493 | 10/1999 |
| EP | 2305749 | 10/1999 |
| EP | 2330152 | 10/1999 |
| EP | 953326 | 11/1999 |
| EP | 0978263 A1 | 2/2000 |
| EP | 985397 | 3/2000 |
| EP | 1005847 B1 | 6/2000 |
| EP | 1008333 A3 | 6/2000 |
| EP | 1018999 | 7/2000 |
| EP | 1022008 | 7/2000 |
| EP | 1023884 | 8/2000 |
| EP | 1053729 | 11/2000 |
| EP | 1059072 A2 | 12/2000 |
| EP | 1063954 | 1/2001 |
| EP | 1071388 | 1/2001 |
| EP | 1078618 | 2/2001 |
| EP | 1088537 A2 | 4/2001 |
| EP | 0796068 | 5/2001 |
| EP | 796068 B1 | 5/2001 |
| EP | 752892 B1 | 7/2001 |
| EP | 1116479 A2 | 7/2001 |
| EP | 0790839 | 8/2001 |
| EP | 1132069 | 9/2001 |
| EP | 1173128 | 1/2002 |
| EP | 1184018 | 3/2002 |
| EP | 1199059 | 4/2002 |
| EP | 1199327 A2 | 4/2002 |
| EP | 1208824 | 5/2002 |
| EP | 0793469 | 6/2002 |
| EP | 793469 B1 | 6/2002 |
| EP | 1210925 | 6/2002 |
| EP | 1224922 | 7/2002 |
| EP | 1225857 | 7/2002 |
| EP | 1253231 | 10/2002 |
| EP | 1262531 A1 | 12/2002 |
| EP | 0737056 | 1/2003 |
| EP | 1275358 | 1/2003 |
| EP | 1275361 | 1/2003 |
| EP | 1293187 | 3/2003 |
| EP | 1339368 | 9/2003 |
| EP | 1374817 | 1/2004 |
| EP | 1388334 | 2/2004 |
| EP | 1402863 | 3/2004 |
| EP | 962208 | 8/2004 |
| EP | 1447066 A1 | 8/2004 |
| EP | 1447067 A1 | 8/2004 |
| EP | 1460987 | 9/2004 |
| EP | 963749 | 11/2004 |
| EP | 1263374 B1 | 11/2004 |
| EP | 1495739 | 1/2005 |
| EP | 1524955 | 4/2005 |
| EP | 1920743 | 4/2005 |
| EP | 1541103 | 6/2005 |
| EP | 1551344 | 7/2005 |
| EP | 1586289 | 10/2005 |
| EP | 1588723 | 10/2005 |
| EP | IN0984KO11999 | 10/2005 |
| EP | 1605882 | 12/2005 |
| EP | 1609448 | 12/2005 |
| EP | 1019003 B1 | 1/2006 |
| EP | 1621166 | 2/2006 |
| EP | 1621167 A2 | 2/2006 |
| EP | 1632206 | 3/2006 |
| EP | 1642556 | 4/2006 |
| EP | 1403419 | 5/2006 |
| EP | 1656162 | 5/2006 |
| EP | 1669046 | 6/2006 |
| EP | 1019002 B1 | 8/2006 |
| EP | 1688114 | 8/2006 |
| EP | 2314265 | 8/2006 |
| EP | 1723939 | 11/2006 |
| EP | 1192312 B1 | 12/2006 |
| EP | 1013252 B1 | 1/2007 |
| EP | 1738727 | 1/2007 |
| EP | 1754461 | 2/2007 |
| EP | 1787611 | 5/2007 |
| EP | 1175194 B1 | 6/2007 |
| EP | 1813238 | 8/2007 |
| EP | 1304986 B1 | 11/2007 |
| EP | 1332742 B1 | 6/2008 |
| EP | 2008626 | 12/2008 |
| EP | 2055279 A1 | 5/2009 |
| EP | IN0980MUM2009 | 6/2009 |
| EP | 2093049 | 8/2009 |
| EP | 2130522 | 12/2009 |
| EP | 1621165 | 4/2010 |
| EP | 1196122 B2 | 11/2011 |
| EP | 2444046 A1 | 4/2012 |
| EP | 2532328 | 12/2012 |
| EP | 2532329 A1 | 12/2012 |
| EP | 2532332 A1 | 12/2012 |
| EP | 2679210 A1 | 1/2014 |
| EP | 2740449 | 6/2014 |
| EP | 2740450 A1 | 6/2014 |
| EP | 2740452 A1 | 6/2014 |
| EP | 0778762 | 4/2020 |
| ES | 2213491 | 8/2004 |
| FR | 2566631 | 1/1986 |
| FR | 2583377 | 12/1986 |
| FR | 2612770 | 9/1988 |
| FR | 2810234 | 12/2001 |
| GB | 1307441 A | 2/1973 |
| GB | 1333081 A | 10/1973 |
| GB | 1513055 A | 6/1978 |
| GB | 2101468 | 1/1983 |
| GB | 2170108 A | 7/1986 |
| GB | 2262873 | 7/1993 |
| GB | 2288540 A | 10/1995 |
| GB | 2354449 A1 | 3/2001 |
| GB | 2452260 A | 3/2009 |
| GR | 851769 B | 11/1985 |
| IN | 212479 | 3/2007 |
| IN | 208543 | 8/2007 |
| JP | 5572928 | 5/1980 |
| JP | 598322 | 1/1984 |
| JP | 63148323 U | 9/1988 |
| JP | 2107250 | 4/1990 |
| JP | 03224481 | 10/1991 |
| JP | 04122256 | 4/1992 |
| JP | 04341368 | 11/1992 |
| JP | 06191505 | 7/1994 |
| JP | 06269475 A | 9/1994 |
| JP | 07124193 | 5/1995 |
| JP | 08215629 | 8/1996 |
| JP | H10295728 A | 11/1998 |
| JP | 10328232 | 12/1998 |
| JP | 11033056 | 2/1999 |
| JP | 11318980 | 11/1999 |
| JP | 11320742 | 11/1999 |
| JP | 2000232985 A | 8/2000 |
| JP | 2000238161 A | 9/2000 |
| JP | 2001037810 A | 2/2001 |
| JP | 2001046435 A | 2/2001 |
| JP | 2001120597 A | 5/2001 |
| JP | 2001158074 A | 6/2001 |
| JP | 2001178768 A | 7/2001 |
| JP | 2001198157 A | 7/2001 |
| JP | 2001224626 A | 8/2001 |
| JP | 2001277394 A | 10/2001 |

(56) References Cited

FOREIGN PATENT DOCUMENTS

| | | |
|---|---|---|
| JP | 03420481 | 11/2001 |
| JP | 2001321397 A | 11/2001 |
| JP | 2001353174 A | 12/2001 |
| JP | 2002052042 A | 2/2002 |
| JP | 2002065718 A | 3/2002 |
| JP | 2002113800 A | 4/2002 |
| JP | 2002165832 A | 6/2002 |
| JP | 2002165836 A | 6/2002 |
| JP | 2002178429 A | 6/2002 |
| JP | 2002272769 A | 9/2002 |
| JP | 2002325792 A | 11/2002 |
| JP | 2002325799 A | 11/2002 |
| JP | 2002369841 A | 12/2002 |
| JP | 2003126140 A | 5/2003 |
| JP | 2003153955 A | 5/2003 |
| JP | 2003265523 A | 9/2003 |
| JP | 2003265524 A | 9/2003 |
| JP | 2003275237 A | 9/2003 |
| JP | 2003325563 A | 11/2003 |
| JP | 2004089269 A | 3/2004 |
| JP | 03566012 | 6/2004 |
| JP | 03568146 | 6/2004 |
| JP | 03616077 | 11/2004 |
| JP | 2004337314 A | 12/2004 |
| JP | 2004337385 A | 12/2004 |
| JP | 2004350864 A | 12/2004 |
| JP | 03640475 | 1/2005 |
| JP | 2005000312 A | 1/2005 |
| JP | 03660816 | 3/2005 |
| JP | 03676219 | 5/2005 |
| JP | 03688403 | 6/2005 |
| JP | 03705943 | 8/2005 |
| JP | 03719819 | 9/2005 |
| JP | 03724963 | 9/2005 |
| JP | 03725008 | 9/2005 |
| JP | 03737376 | 11/2005 |
| JP | 2006014792 A | 1/2006 |
| JP | 03781617 | 3/2006 |
| JP | 2006110329 A | 4/2006 |
| JP | 2006513824 A | 4/2006 |
| JP | 03801449 | 5/2006 |
| JP | 2006116036 A | 5/2006 |
| JP | 03850102 | 9/2006 |
| JP | 03850207 | 9/2006 |
| JP | 03856941 | 9/2006 |
| JP | 03868628 | 10/2006 |
| JP | 03874499 | 11/2006 |
| JP | 03877702 | 11/2006 |
| JP | 2006325639 A | 12/2006 |
| JP | 2006346021 A | 12/2006 |
| JP | 03904356 | 1/2007 |
| JP | 2007007455 A | 1/2007 |
| JP | 2007007456 A | 1/2007 |
| JP | 03926042 | 3/2007 |
| JP | 03934855 | 3/2007 |
| JP | 2007089906 A | 4/2007 |
| JP | 2007105198 A | 4/2007 |
| JP | 2007152033 A | 6/2007 |
| JP | 03986210 | 7/2007 |
| JP | 03986222 | 7/2007 |
| JP | 2007167453 A | 7/2007 |
| JP | 2007175515 A | 7/2007 |
| JP | 2007195665 A | 8/2007 |
| JP | 2007267763 A | 10/2007 |
| JP | 2007275491 A | 10/2007 |
| JP | 04035341 | 11/2007 |
| JP | 04058281 | 12/2007 |
| JP | 04061086 | 12/2007 |
| JP | 04092319 | 3/2008 |
| JP | 2008080150 A | 4/2008 |
| JP | 2008093289 A | 4/2008 |
| JP | 04124322 | 5/2008 |
| JP | 2008119081 A | 5/2008 |
| JP | 2008136739 A | 6/2008 |
| JP | 2008136877 A | 6/2008 |
| JP | 04148594 | 7/2008 |
| JP | 04148620 | 7/2008 |
| JP | 2008154606 A | 7/2008 |
| JP | 04162609 | 8/2008 |
| JP | 04162637 | 8/2008 |
| JP | 04166923 | 8/2008 |
| JP | 04167406 | 8/2008 |
| JP | 04173723 | 8/2008 |
| JP | 4177770 B2 | 8/2008 |
| JP | 04190675 | 9/2008 |
| JP | 04190693 | 9/2008 |
| JP | 04208338 | 10/2008 |
| JP | 2008246089 A | 10/2008 |
| JP | 04230971 | 12/2008 |
| JP | 2008295475 A | 12/2008 |
| JP | 2008295713 A | 12/2008 |
| JP | 04261593 | 2/2009 |
| JP | 2009112590 A | 5/2009 |
| JP | 2009136601 A | 6/2009 |
| JP | 2009142401 A | 7/2009 |
| JP | 04322228 | 8/2009 |
| JP | 2009201878 A | 9/2009 |
| JP | 04392936 | 10/2009 |
| JP | 2009232987 A | 10/2009 |
| JP | 2009261777 A | 11/2009 |
| JP | 2009291473 A | 12/2009 |
| JP | 2009297048 A | 12/2009 |
| JP | 2010017342 A | 1/2010 |
| JP | 04458702 | 2/2010 |
| JP | 04459013 | 2/2010 |
| JP | 2010022560 A | 2/2010 |
| JP | 04481325 | 3/2010 |
| JP | 2010051654 A | 3/2010 |
| JP | 2010063814 A | 3/2010 |
| JP | 2010063944 A | 3/2010 |
| JP | 04492957 | 4/2010 |
| JP | 2010068954 A | 4/2010 |
| JP | 2010075462 A | 4/2010 |
| JP | 2010082059 A | 4/2010 |
| JP | 2010104545 A | 5/2010 |
| JP | 2010104547 A | 5/2010 |
| JP | 2010110535 A | 5/2010 |
| JP | 2010119454 A | 6/2010 |
| JP | 2010119605 A | 6/2010 |
| JP | 2010119743 A | 6/2010 |
| JP | 2010131131 A | 6/2010 |
| JP | 2010131132 A | 6/2010 |
| JP | 2010131206 A | 6/2010 |
| JP | 2010131297 A | 6/2010 |
| JP | 2010136917 A | 6/2010 |
| JP | 2010136973 A | 6/2010 |
| JP | 04540563 | 7/2010 |
| JP | 4577766 B2 | 9/2010 |
| JP | 04587947 | 9/2010 |
| JP | 2010194124 A | 9/2010 |
| JP | 2010201093 A | 9/2010 |
| JP | 2010221067 A | 10/2010 |
| JP | 04620299 | 11/2010 |
| JP | 04627472 | 11/2010 |
| JP | 04627473 | 11/2010 |
| JP | 04638087 | 12/2010 |
| JP | 04652626 | 12/2010 |
| JP | 2010273842 A | 12/2010 |
| JP | 2010284418 A | 12/2010 |
| JP | 2011000480 A | 1/2011 |
| JP | 2011030700 A | 2/2011 |
| JP | 04693574 | 3/2011 |
| JP | 2011067484 A | 4/2011 |
| JP | 2011072720 A | 4/2011 |
| JP | 2011104014 A | 6/2011 |
| JP | 2011104122 A | 6/2011 |
| JP | 2011120661 A | 6/2011 |
| JP | 2011125360 A | 6/2011 |
| JP | 2011125537 A | 6/2011 |
| JP | 04776516 | 7/2011 |
| JP | 2011130797 A | 7/2011 |
| JP | 2011130799 A | 7/2011 |
| JP | 2011156032 A | 8/2011 |
| JP | 2011156070 A | 8/2011 |

(56) References Cited

FOREIGN PATENT DOCUMENTS

| | | |
|---|---|---|
| JP | 2011156254 A | 8/2011 |
| JP | 04824882 | 9/2011 |
| JP | 4850272 B2 | 10/2011 |
| JP | 04855533 | 11/2011 |
| JP | 2011239858 A | 12/2011 |
| JP | 2011240050 A | 12/2011 |
| JP | 04931572 | 2/2012 |
| JP | 04953618 | 3/2012 |
| JP | 04969437 | 4/2012 |
| JP | 04969640 | 4/2012 |
| JP | 4971491 B2 | 4/2012 |
| JP | 04974524 | 4/2012 |
| JP | 04979780 | 4/2012 |
| JP | 04937225 | 5/2012 |
| JP | 05016020 | 6/2012 |
| JP | 05027364 | 6/2012 |
| JP | 5715806 B2 | 6/2012 |
| JP | 2012115378 A | 6/2012 |
| JP | 05031082 | 7/2012 |
| JP | 05042351 | 7/2012 |
| JP | 05043569 | 7/2012 |
| JP | 05043591 | 7/2012 |
| JP | 05046488 | 7/2012 |
| JP | 2012125452 A | 7/2012 |
| JP | 2012125625 A | 7/2012 |
| JP | 05053765 | 8/2012 |
| JP | 05070275 | 8/2012 |
| JP | 05079931 B1 | 9/2012 |
| JP | 05080189 | 9/2012 |
| JP | 05084442 | 9/2012 |
| JP | 05084476 | 9/2012 |
| JP | 5085770 B2 | 9/2012 |
| JP | 05089269 | 9/2012 |
| JP | 2012179286 A | 9/2012 |
| JP | 05113146 | 10/2012 |
| JP | 05129536 | 11/2012 |
| JP | 2012223231 A | 11/2012 |
| JP | 05105884 | 12/2012 |
| KR | 20010005620 A | 1/2001 |
| KR | 20020035634 A | 5/2002 |
| KR | 20080028771 A | 4/2008 |
| SE | 9400916 | 3/1994 |
| SE | 9704893 | 12/1997 |
| WO | 9015830 A1 | 12/1990 |
| WO | 9219198 A1 | 11/1992 |
| WO | 9321237 A1 | 10/1993 |
| WO | 9321879 A1 | 11/1993 |
| WO | 9510996 A1 | 4/1995 |
| WO | 9511652 A1 | 5/1995 |
| WO | 9514453 | 6/1995 |
| WO | 9515139 A1 | 6/1995 |
| WO | 9516424 A1 | 6/1995 |
| WO | 9516746 A1 | 6/1995 |
| WO | 9519753 A1 | 7/1995 |
| WO | 9521596 A1 | 8/1995 |
| WO | 9524173 A2 | 9/1995 |
| WO | 9526209 A1 | 10/1995 |
| WO | 9529657 A1 | 11/1995 |
| WO | 9532698 A1 | 12/1995 |
| WO | 9534329 A1 | 12/1995 |
| WO | 9616624 | 6/1996 |
| WO | 9619173 A1 | 6/1996 |
| WO | 96029967 | 10/1996 |
| WO | 9711659 A1 | 4/1997 |
| WO | 9717922 A1 | 5/1997 |
| WO | 9724096 A1 | 7/1997 |
| WO | 9816179 A1 | 4/1998 |
| WO | 9816180 A1 | 4/1998 |
| WO | 9843684 A1 | 10/1998 |
| WO | 9913813 A1 | 7/1999 |
| WO | 9934841 A1 | 7/1999 |
| WO | 9951178 A1 | 10/1999 |
| WO | 200000235 | 1/2000 |
| WO | 0032145 A1 | 6/2000 |
| WO | 200059430 A1 | 10/2000 |
| WO | 0115647 A1 | 3/2001 |
| WO | 200126596 | 4/2001 |
| WO | 0135886 A1 | 5/2001 |
| WO | 200207663 | 1/2002 |
| WO | 200232962 | 4/2002 |
| WO | 2002064877 | 8/2002 |
| WO | 2002067809 A2 | 9/2002 |
| WO | 2003009794 | 2/2003 |
| WO | 2003039402 | 5/2003 |
| WO | 2003053297 | 7/2003 |
| WO | 03079946 A2 | 10/2003 |
| WO | 03101622 | 12/2003 |
| WO | 2003105738 | 12/2003 |
| WO | 2004021946 A1 | 3/2004 |
| WO | 2004049995 A1 | 6/2004 |
| WO | 2004071539 A3 | 8/2004 |
| WO | 2004084784 A1 | 10/2004 |
| WO | 2004105664 A1 | 12/2004 |
| WO | 2005018694 A1 | 3/2005 |
| WO | 2005087164 A1 | 9/2005 |
| WO | 2005102237 A1 | 11/2005 |
| WO | 2006059922 A1 | 6/2006 |
| WO | 2006062258 A2 | 6/2006 |
| WO | 2006066029 A1 | 6/2006 |
| WO | 2006083584 | 8/2006 |
| WO | 2006104024 A1 | 10/2006 |
| WO | 2006134904 A1 | 12/2006 |
| WO | 2006134906 A1 | 12/2006 |
| WO | 2007000315 A1 | 1/2007 |
| WO | 2007046052 A1 | 4/2007 |
| WO | 2007047598 A1 | 4/2007 |
| WO | 2007049725 A1 | 5/2007 |
| WO | 2007061035 A1 | 5/2007 |
| WO | 2007141744 A1 | 12/2007 |
| WO | 2007142145 A1 | 12/2007 |
| WO | 2007148502 A1 | 12/2007 |
| WO | 2008018922 A1 | 2/2008 |
| WO | 2008065945 A1 | 6/2008 |
| WO | 2008146749 A1 | 12/2008 |
| WO | 2008155699 A1 | 12/2008 |
| WO | 2009004941 A1 | 1/2009 |
| WO | 2009005431 A1 | 1/2009 |
| WO | 2009041223 A1 | 4/2009 |
| WO | 2009096108 A1 | 8/2009 |
| WO | 2009107435 A1 | 9/2009 |
| WO | 2009122830 A1 | 10/2009 |
| WO | 2009139248 A1 | 11/2009 |
| WO | 2009139255 A1 | 11/2009 |
| WO | 2009152018 A1 | 12/2009 |
| WO | 2009155264 | 12/2009 |
| WO | 2009155265 | 12/2009 |
| WO | 2010071508 A1 | 6/2010 |
| WO | 2010074319 A1 | 7/2010 |
| WO | 2010107096 A1 | 9/2010 |
| WO | 2010114052 A1 | 10/2010 |
| WO | 2010117015 A1 | 10/2010 |
| WO | 2010118272 A1 | 10/2010 |
| WO | 201153044 A1 | 5/2011 |
| WO | 2011118725 A1 | 9/2011 |
| WO | 2011118842 A1 | 9/2011 |
| WO | 2011145653 A1 | 11/2011 |
| WO | 2011150955 A1 | 12/2011 |
| WO | 2011163582 A1 | 12/2011 |
| WO | 2012002252 A1 | 1/2012 |
| WO | 2012014436 A1 | 2/2012 |
| WO | 2012042908 A1 | 4/2012 |
| WO | 2012043077 A1 | 4/2012 |
| WO | 2012043078 A1 | 4/2012 |
| WO | 2012043082 A1 | 4/2012 |
| WO | 2012052172 A1 | 4/2012 |
| WO | 2012067216 A1 | 5/2012 |
| WO | 2012073499 A1 | 6/2012 |
| WO | 2012074466 A1 | 6/2012 |
| WO | 201291016 | 7/2012 |
| WO | 2012090508 A1 | 7/2012 |
| WO | 2012101934 A1 | 8/2012 |
| WO | 2012102034 A1 | 8/2012 |
| WO | 2012117764 A1 | 9/2012 |
| WO | 2012117824 A1 | 9/2012 |

(56) References Cited

FOREIGN PATENT DOCUMENTS

| WO | 2012132460 A1 | 10/2012 |
|---|---|---|
| WO | 2012170778 A1 | 12/2012 |
| WO | 2012170779 A1 | 12/2012 |
| WO | 2012170781 A1 | 12/2012 |
| WO | 2012170808 A1 | 12/2012 |
| WO | 2012174026 A1 | 12/2012 |
| WO | 2013001788 A1 | 1/2013 |
| WO | 2012177400 A1 | 4/2013 |
| WO | 2013046701 A1 | 4/2013 |
| WO | 2013060733 A1 | 5/2013 |
| WO | 2014073636 A1 | 5/2014 |
| WO | 2014078247 A2 | 5/2014 |

OTHER PUBLICATIONS

All Office Actions; U.S. Appl. No. 16/295,012, filed on Mar. 7, 2019.

All Office Actions; U.S. Appl. No. 14/077,355, filed on Nov. 12, 2013.

All Office Actions; U.S. Appl. No. 15/354,017, filed on Nov. 17, 2016.

All Office Actions; U.S. Appl. No. 15/824,002, filed on Nov. 28, 2017.

F.L. Buchholz et al. Modern Superabsorbent, "Modern Superabsorbent Polymer Technology", F.L. Buchholz, A.T. Graham, Wiley, dated 1998, p. 30.

International Search Report and Written Opinion; Application Ser. No. PCT/US2013/069521; dated Oct. 8, 2014, 16 pages.

\* cited by examiner

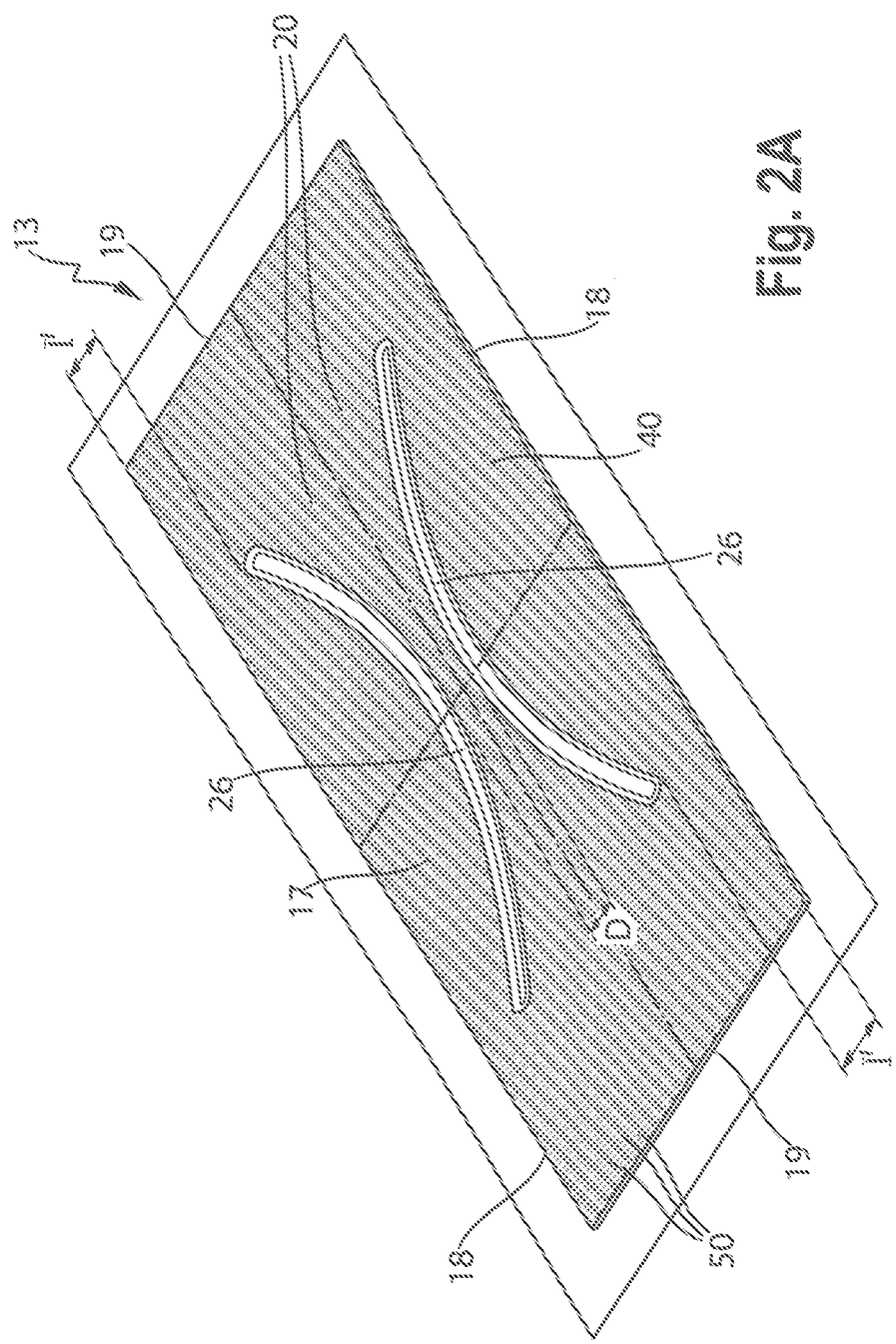

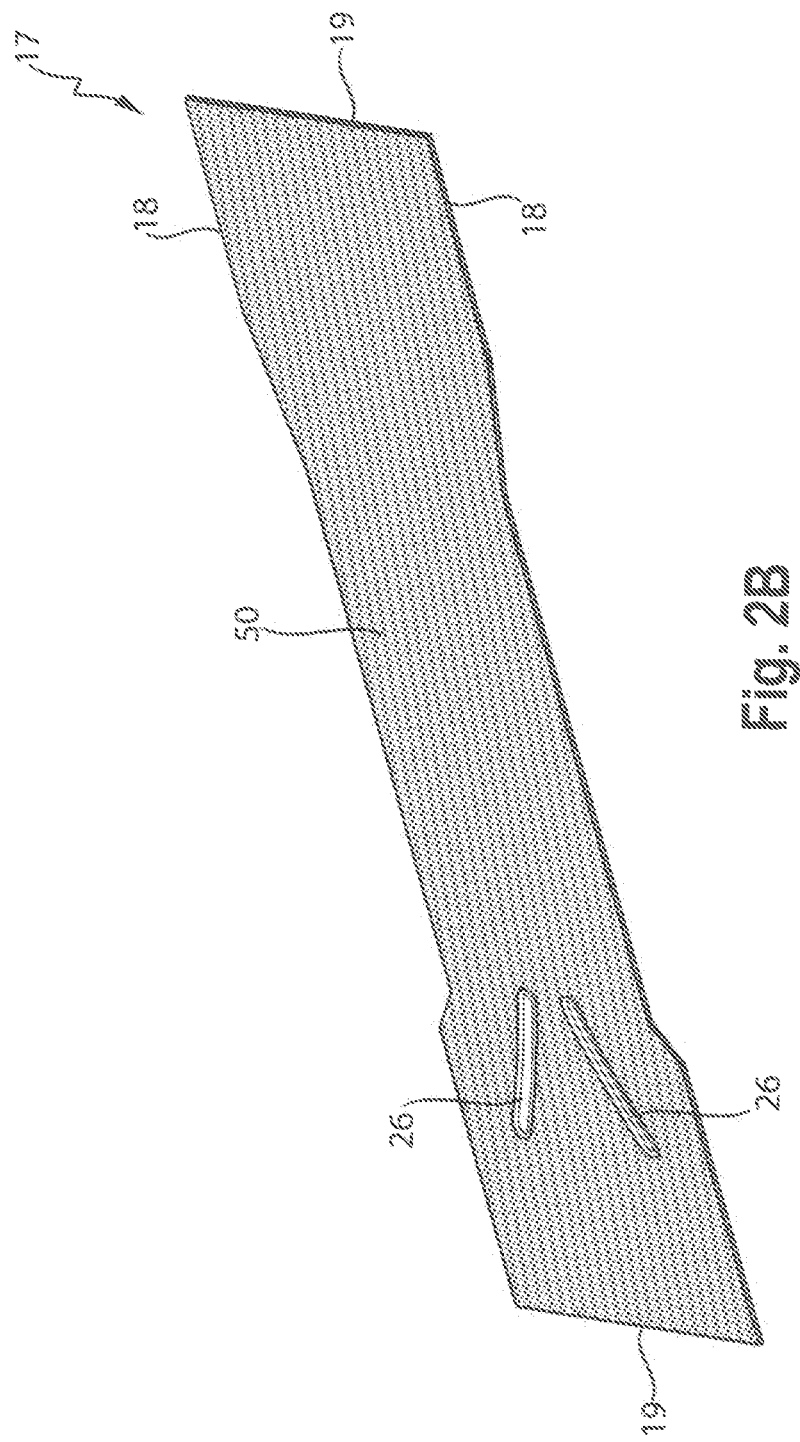

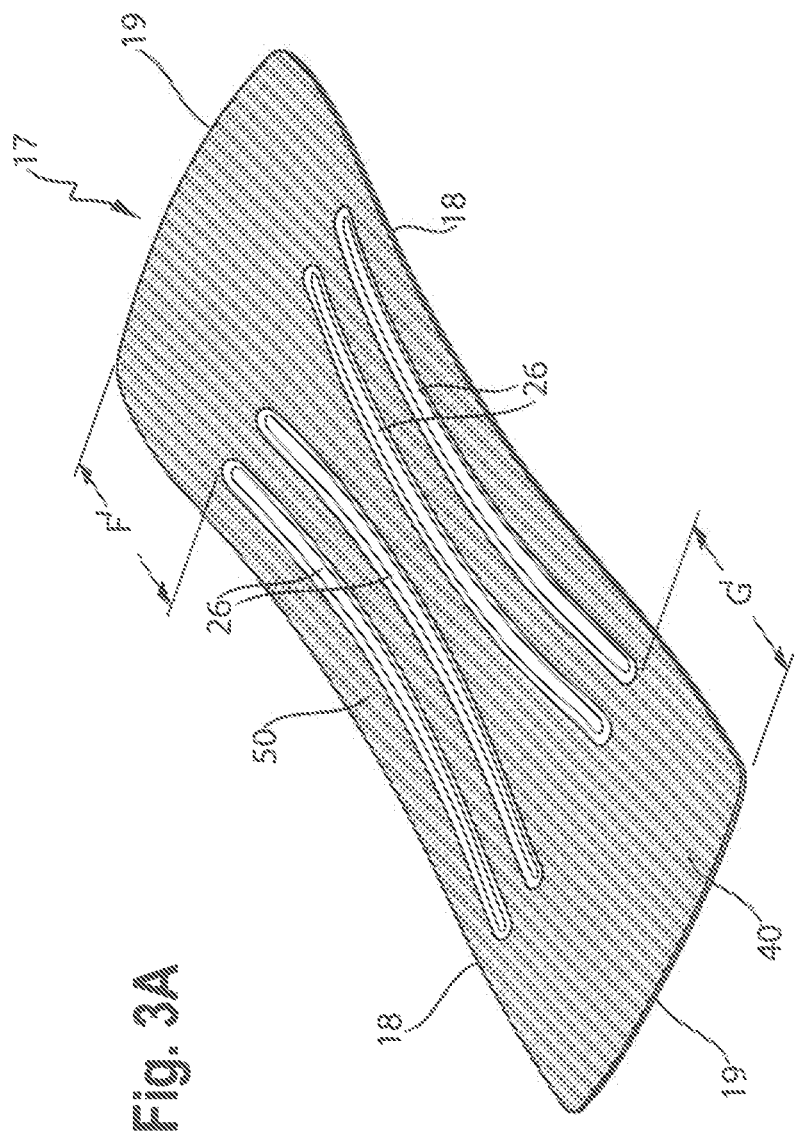

ABSORBENT ARTICLES WITH CHANNELS AND SIGNALS

FIELD OF THE INVENTION

The present invention relates to absorbent articles with channeled cores and printed signals.

BACKGROUND OF THE INVENTION

Absorbent articles for receiving and retaining bodily discharges such as urine or feces are well known in the art. Examples of these include disposable diaper(s), training pants and adult incontinence articles. Typically, disposable diapers comprise a liquid pervious topsheet that faces the wearer's body, a liquid impervious backsheet that faces the wearer's clothing and an absorbent core interposed between the liquid pervious topsheet and the backsheet.

An important component of disposable absorbent articles is the absorbent core/absorbent structure. The absorbent core/structure typically includes superabsorbent polymer material, such as hydrogel-forming polymer material, also referred to as absorbent gelling material, AGM, or superabsorbent polymer, SAP. This superabsorbent polymer material ensures that large amounts of bodily fluids, e.g. urine, can be absorbed by the absorbent article during its use and be locked away, thus providing low rewet and good skin dryness.

Traditionally, the superabsorbent polymer material is incorporated into the absorbent core structure with pulp, i.e. cellulose fibres. To make the absorbent core structures thinner, it has been proposed to reduce or eliminate these cellulose fibres from the absorbent core structures.

However, it was found that some absorbent core structures with reduced cellulose fibre levels, whilst very thin when not loaded with bodily fluids, may have an increased stiffness when partially loaded or fully loaded, especially in those regions which comprise most of the absorbent capacity of the absorbent article, such as the front region and crotch region of the diaper. It has been found that by providing specific permanent channels that are free of superabsorbent polymer particles or free of superabsorbent polymer material, improved liquid transport is achieved, and hence faster acquisition, and more efficient liquid absorbency over the whole absorbent structure; even though less absorbent material may be used, surprisingly improved performance can be achieved. By immobilising the absorbent material or channels (by the use of adhesive, the channels are more permanent, and remain channels during the use of the absorbent structure, e.g. when friction is applied to the absorbent structure, or when the absorbent structure is wetted, and the absorbent material expands. Furthermore, it has been found that by the provision of such channels, for example in the front region of the absorbent core/structure, and/or in the crotch region of the absorbent core/structure, a diaper of increased flexibility can be provided, whilst surprisingly maintaining its performance throughout its use.

As the functionality of the absorbent core is changed to improve, e.g. absorbency, fit, or reduced cost, the performance and/or appearance of the article may be affected negatively. Efforts can be made to modify the article or parts of the article in order to provide them with a particular appearance. In some examples, the article may be modified to communicate or signal to the caregiver that the channels exist in the absorbent core of the article, and that the channels are there to create faster and more efficient liquid absorbency. Such signalling or communication may be done, for example, via exterior graphics and/or interior printed adhesives. As such, there is a need for improved absorbent articles comprising absorbent cores with channels that exhibit excellent performance and that are aesthetically pleasing.

SUMMARY OF THE INVENTION

Absorbent articles herein may provide a topsheet, a backsheet, an absorbent core disposed between the topsheet and the backsheet. The absorbent core may comprise a channel, and the backsheet may comprise graphics which substantially match the shape of the channel.

BRIEF DESCRIPTION OF THE DRAWINGS

FIG. 2A shows a perspective view of an absorbent structure in accordance with one non-limiting embodiment.

FIG. 2B shows a perspective view of an alternative absorbent layer in accordance with one non-limiting embodiment.

FIG. 3A shows a perspective view of an alternative absorbent layer in accordance with one non-limiting embodiment.

DETAILED DESCRIPTION OF THE INVENTION

Definitions

Figure 1:
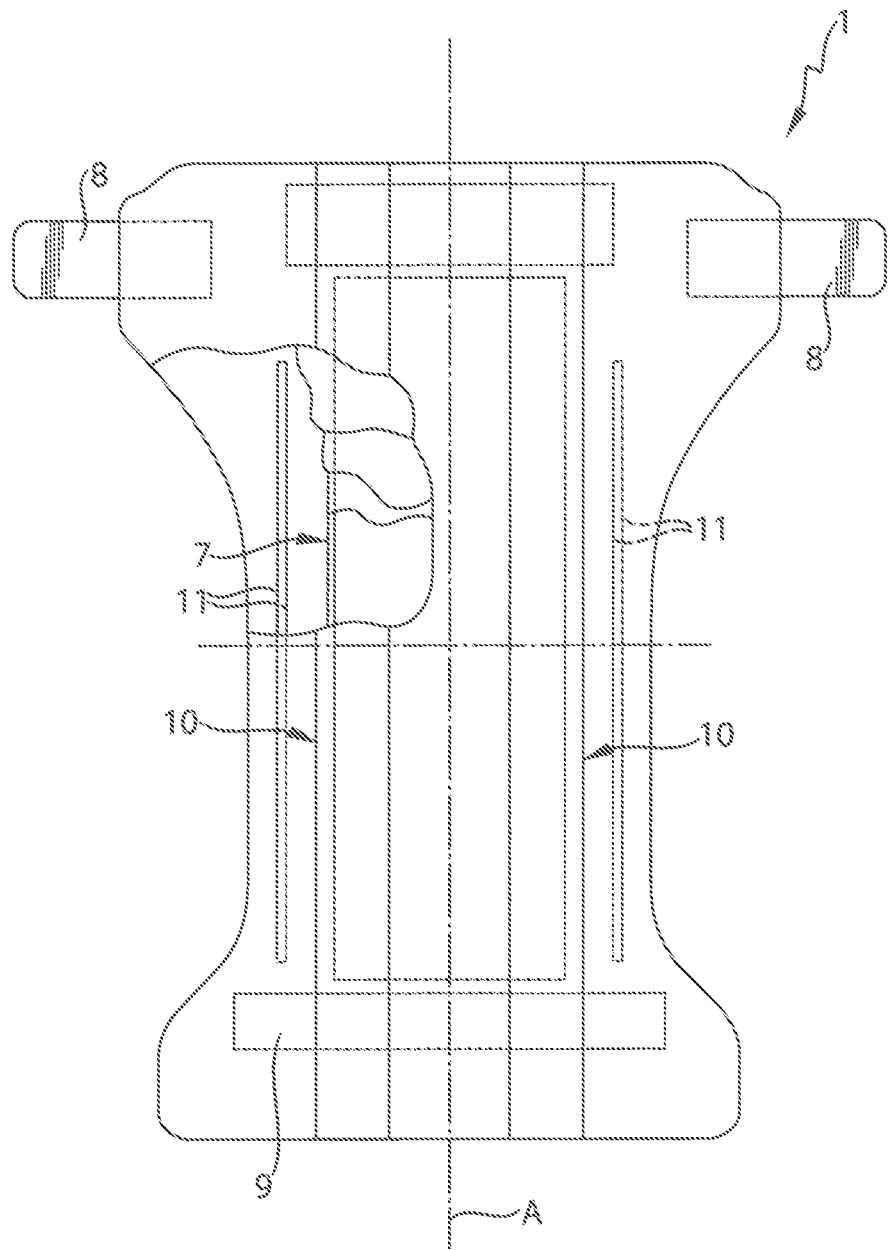
FIG. 1 shows a plan view of a diaper in accordance with one non-limiting embodiment.

"Absorbent article" refers to a device that absorbs and contains body exudates, and, more specifically, refers to devices that are placed against or in proximity to the body of the wearer to absorb and contain the various exudates discharged from the body. Absorbent articles may include adult and infant diaper (1), including pants, such as infant training pants and adult incontinence undergarments, and feminine hygiene products, such as sanitary napkins and panty-liners and adult in continent pads, and breast pads, care mats, bibs, wound dressing products, and the like. Absorbent articles may further include floor cleaning articles, food industry articles, and the like. As used herein, the term "body fluids" or "body exudates" includes, but is not limited to, urine, blood, vaginal discharges, breast milk, sweat and fecal matter.

As used herein "diaper (1)" refers to devices which are intended to be placed against the skin of a wearer to absorb and contain the various exudates discharged from the body. Diaper (1)s are generally worn by infants and incontinent persons about the lower torso so as to encircle the waist and legs of the wearer. Examples of diaper (1)s include infant or adult diaper (1)s and pant-like diaper (1)s such as training pants. A diaper may comprise a fastening system, which may include at least one fastening member (8) and at least one landing zone (9), and may also comprise leg cuffs (10) and elastic members (11). "Training pant", as used herein, refers to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened).

"Disposable" is used herein to describe articles that are generally not intended to be laundered or otherwise restored or reused (i.e., they are intended to be discarded after a single use and, may be recycled, composted or otherwise disposed of in an environmentally compatible manner).

As used herein "absorbent structure (13)" refers to a three dimensional structure useful to absorb and contain liquids, such as urine. The absorbent structure (13) may be the absorbent structure (13) of an absorbent article or may be only part of the absorbent core (7) of an absorbent article, i.e. an absorbent component of the absorbent core (7), as will be further described herein.

"Superabsorbent polymer material" as used herein refers to substantially water-insoluble polymer material that can absorb at least 10 times (and typically at least 15 times or at least 20 times) its weight of a 0.9% saline solution in de-mineralized water as measured using the Centrifuge Retention Capacity test (Edana 441.2-01).

"Nonwoven material" as used herein refers to a manufactured web of directionally or randomly orientated fibers, excluding paper and products which are woven, knitted, tufted, stitch-bonded incorporating binding yarns or filaments, or felted by wet-milling, whether or not additionally needled. Nonwoven materials and processes for making them are known in the art. Generally, processes for making nonwoven materials comprise laying fibers onto a forming surface, which may comprise spunlaying, meltblowing, carding, airlaying, wetlaying, coform and combinations thereof. The fibers may be of natural or man-made origin and may be staple fibers or continuous filaments or be formed in situ.

"Visible" as used herein means capable of being perceived by the unaided human eye.

Absorbent Structure (13) with Channels

The present invention provides absorbent articles with absorbent cores comprising channels and printed signals that communicate the channels. The present invention relates to absorbent articles with channels disclosed in U.S. application Ser. Nos. 13/491,642, 13/491,643, 13/491,644, and 13/491,648, all filed Jun. 10, 2011.

The absorbent structure (13) herein comprises a supporting sheet (16) with an absorbent layer (17) of absorbent material (50). The absorbent material (50) comprises at least a superabsorbent polymer material and optionally a cellulosic material, such as a cellulose, e.g. pulp, or modified cellulose.

The absorbent structure (13) also comprises one or more adhesive material(s), further described below. The absorbent layer (17) is three dimensional and comprises a first substantially longitudinal channel (26) and a second substantially longitudinal channel (26) that are substantially free of said superabsorbent polymer material. Other materials may be present in said channels (26), as further described below, for example said one or more adhesive material(s) (40; 60).

The absorbent structure (13) and the absorbent layer (17) each have a longitudinal dimension and average length L, e.g. extending in the longitudinal dimension of the structure or layer and a transverse dimension and average width W, e.g. extending in the transverse dimension of the structure or layer. The absorbent structure (13) and the absorbent layer (17) each have a front region, being in use towards the front of the user, back region, being in use towards the back of the user, and therein between a crotch region, each extending the full transverse width of the structure/layer, and each having ⅓ of the average length of the structure/layer.

The absorbent structure (13) and the absorbent layer (17) each possess a central longitudinal axis X, a central transverse axis Y perpendicular to said central longitudinal axis X; said absorbent layer (17) and said absorbent structure (13) have each a pair of opposing longitudinal side edges extending in the longitudinal dimension of the structure or layer and a pair of opposing transverse edges (19), e.g. front transverse edge being in use towards the front of a user (wearer), and a back transverse edge being in use towards the back of a user. The longitudinal side edges (18) and/or transverse edges (19) of the absorbent structure (13) or absorbent layer (17) may be parallel respectively to the central longitudinal axis and/or central transverse axis respectively or one or more may be curvilinear, and for instance provide for a narrower transverse dimension in the crotch region. Typically the longitudinal side edges are mirror images of one another in the longitudinal X-axis.

The central longitudinal X-axis of the absorbent layer (17) delimits first and second longitudinal side portions (20) of the absorbent layer (17), respectively, referred herein as longitudinal side portions (20). Each of said longitudinal side portions is thus present in said front region, crotch region and back region, and hence, there is a first longitudinal portion's front region, and a second longitudinal portion's front region etc. In some embodiments herein, said longitudinal portions of the absorbent layer (17) are mirror images of one another in the X-axis of the layer.

The absorbent layer (17) comprises at least a first channel (26) and second channel (26) that are substantially free of (e.g. free of) said superabsorbent polymer particles, said channels (26) extending through the thickness (height) of the absorbent layer (17). (It should be understood that, accidentally, a small, negligible amount of superabsorbent polymer particles may be present in the channel, which does not contribute to the overall functionality). When the absorbent layer (17) comprises cellulosic or cellulose, in some embodiments the said first and second channels (26) are also free of such cellulosic/cellulose material.

The first channel (26) is present in said first longitudinal side portion of the absorbent layer (17) and the second channel (26) is present in said second longitudinal side portion of the absorbent layer (17).

The first and second channel (26) each extend substantially longitudinally, which means typically that each channel (26) extends more in the longitudinal dimension than in the transverse dimension, and typically at least twice as much in the longitudinal dimension than in the transverse dimension.

Thus, this includes channels (26) that are completely longitudinal and parallel to the longitudinal direction of said absorbent layer (17) (i.e. paralleled to said longitudinal-axis); and this includes channels (26) that may be curved, provided the radius of curvature is typically at least equal (optionally at least 1.5 or at least 2.0 times this average transverse dimension) to the average transverse dimension of the absorbent layer; and this includes channels (26) that are straight but under an angle of (e.g. from 5°) up to 30°, or for example up to 20°, or up to 10° with a line parallel to the longitudinal axis. This may also includes channels with an angle therein, provided said angle between two parts of a channel is at least 120°, at least 150°; and in any of these cases, provided the longitudinal extension of the channel is more than the transverse extension.

In some embodiments, there may be no completely or substantially transverse channels present in at least said crotch region, or no such channels at all.

Each of said first and second channels (26) may have an average width W' that is least 4% of the average width W of said absorbent layer (17), or for example W' is at least 7% of W; and/or for example and up to 25% of W, or up to 15% of W; and/or for example at least 5 mm; and for example up to 25 mm, or for example up to 15 mm.

Each of said first and second channels (26) may have an average length L' which may for example be up to 80% of the average length L of said absorbent layer (17); if the channels (26) are only in the front region, or only in the crotch region, or only in the back region, L' is for example up to 25% of L, or up to 20% of L, and/or L' is for example at least 5% of L, or at least 10% of L; and/or L' is for example at least 10 mm, or at least 20 mm; if the channels (26) extend in said crotch region and front region, and optionally the back region, L' is for example up to 80% of L, or up to 70% of L, and/or L' is for example at least 40% of L, or at least 50% of L. In case the channel is not parallel to the longitudinal axis, the length L' of the channel is the length as measured by projection against the longitudinal axis.

The channels (26) may typically be so-called "permanent" channels (26). By permanent, it is meant that the integrity of the channels (26) is at least partially maintained both in the dry state and in the wet state, including during friction by the wearer thereon. The Wet Channel Integrity Test described below can be used to test if channels are permanent following wet saturation and to what extent.

Figure 7:
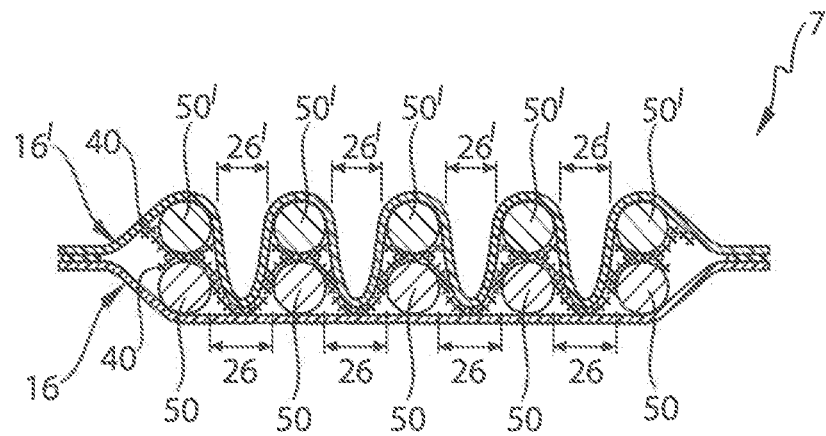
FIG. 7 shows a cross sectional view of an alternative absorbent core in accordance with one non-limiting embodiment.
Figure 8:
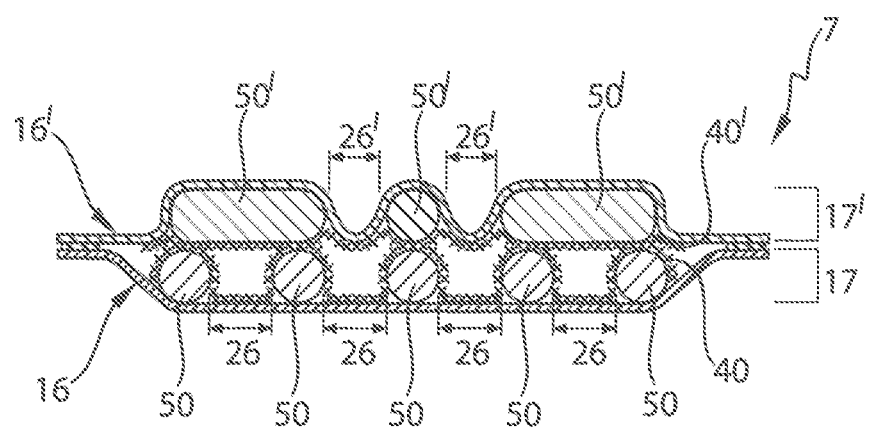
FIG. 8 shows a cross sectional view of an alternative absorbent core in accordance with one non-limiting embodiment.

Permanent channels (26) may be obtained by provision of one or more adhesive material that immobilize said absorbent material (50), and/or said channels (26), e.g. or said absorbent layer (17), and/or that immobilize said supporting sheet (16) into said channels (26), or part thereof. The absorbent cores (7) may comprise in particular permanent channels formed by bonding of the first supporting sheet (16) and second supporting sheet (16') through the channels, as exemplarily shown in FIG. 7 and FIG. 13 for example. Typically, glue may be used to bond both supporting sheets through the channel, but it is possible to bond via other known means, for example ultrasonic bonding, or heat bonding. The supporting layers can be continuously bonded or intermittently bonded along the channels.

Indeed, the inventors observed that such channels provide for fast liquid acquisition which reduces risk of leakages. The permanent channels help to avoid saturation of the absorbent layer in the region of fluid discharge (such saturation increases the risk of leakages). Furthermore, the inventors surprisingly found that, in contrast to what would be expected, whilst decreasing the overall amount of superabsorbent polymer material in the absorbent structure is reduced (by providing channels free of such material), the fluid handling properties of the absorbent structure, or diaper, are improved. Permanent channels, also have the further advantages that in wet state the absorbent material cannot move within the core and remains in its intended position, thus providing better fit and fluid absorption.

Figure 4A:
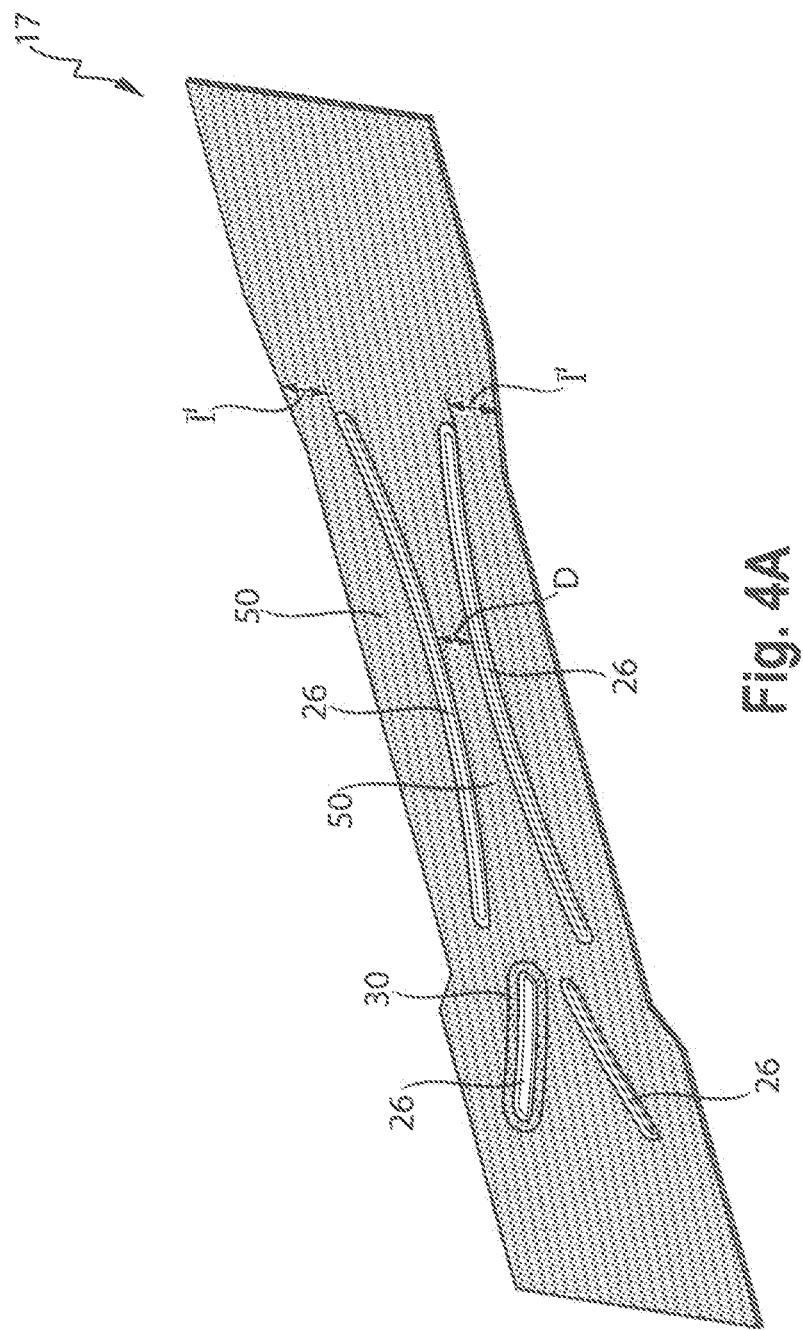
FIG. 4A shows a perspective view of an alternative absorbent layer in accordance with one non-limiting embodiment.

For example, the inventors have compared the amount of AGM loss in a wet state according to the WAIIT test for a core having two absorbent layers with permanent channels as shown in FIG. 4A relative to a similar core with same amount of AGM and glue but having no channels.

In short, the WAIIT test determines the amount of non-immobilized absorbent particulate material amount in the cores in wet conditions. In this test, the absorbent core is wet to 73% capacity and is cut in its middle in the transversal direction and left to fall from a pre-determined height and loss of material is measured. Further information regarding the test can be found in US 2008/0312622 A1.

The results were that the core had a Wet Immobilization of 87% (StDev=5%) of AGM compared to a Wet Immobilization of 65% (StDev=5%) for the comparative core without channels. In this example the channels were made permanent by adhesive bonding of the two supporting sheets in the channels using two layers of thermoplastic fibrous adhesive (Fuller 1151 applied twice at 5 gsm) and one layer of hotmelt adhesive (Fuller 1358 applied at 5 gsm).

Wet Channel Integrity Test

This test is designed to check the integrity of a channel following wet saturation. The test can be performed directly on an absorbent structure or on an absorbent core containing the absorbent structure.

1. The length (in millimeters) of the channel is measured in the dry state (if the channel is not straight, the curvilinear length through the middle of the channel is measured).

2. The absorbent structure or core is then immersed in 5 liters of synthetic urine "Saline", with a concentration of 9.00 g NaCl per 1000 ml solution prepared by dissolving the appropriate amount of sodium chloride in distilled water. The temperature of the solution must be 20+/−5° C.
3. After 1 minute in the saline, the absorbent structure or core is removed and held vertically by one end for 5 seconds to drain, then extended flat on a horizontal surface with the garment-facing side down, if this side is recognizable. If the absorbent structure or core comprises stretch elements, the absorbent structure or core is pulled taut in both X and Y dimensions so that no contraction is observed. The extremes/edges of the absorbent structure or core are fixed to the horizontal surface, so that no contraction can happen.
4. The absorbent structure or core is covered with a suitably weighted rigid plate, with dimensions as follows: length equal to the extended length of the absorbent structure or core, and width equal to the maximum absorbent structure or core width in the cross direction.
5. A pressure of 18.0 kPa is applied for 30 seconds over the area of the rigid plate above mentioned. Pressure is calculated on the basis of overall area encompassed by the rigid plate. Pressure is achieved by placing additional weights in the geometric center of the rigid plate, such that the combined weight of the rigid plate and the additional weights result in a pressure of 18.0 kPa over the total area of the rigid plate.
6. After 30 seconds, the additional weights and the rigid plate are removed.
7. Immediately afterwards, the cumulative length of the portions of the channel which remained intact is measured in millimeters; (if the channel is not straight, the curvilinear length through the middle of the channel is measured). If no portions of the channel remained intact then the channel is not permanent.
8. The percentage of integrity of the permanent channel is calculated by dividing the cumulative length of the portions of the channel which remained intact by the length of the channel in the dry state, and then multiplying the quotient by 100.

Advantageously, a permanent channel according to the disclosure has a percentage of integrity of at least 20%, or 30%, or 40%, or 50%, or 60, or 70%, or 80%, or 90% following this test.

Figure 5:
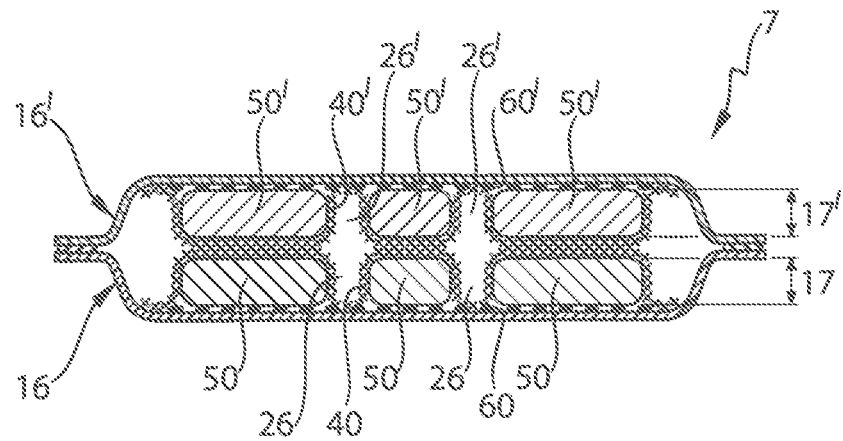
FIG. 5 shows a cross sectional view of an absorbent core in accordance with one non-limiting embodiment.
Figure 6:
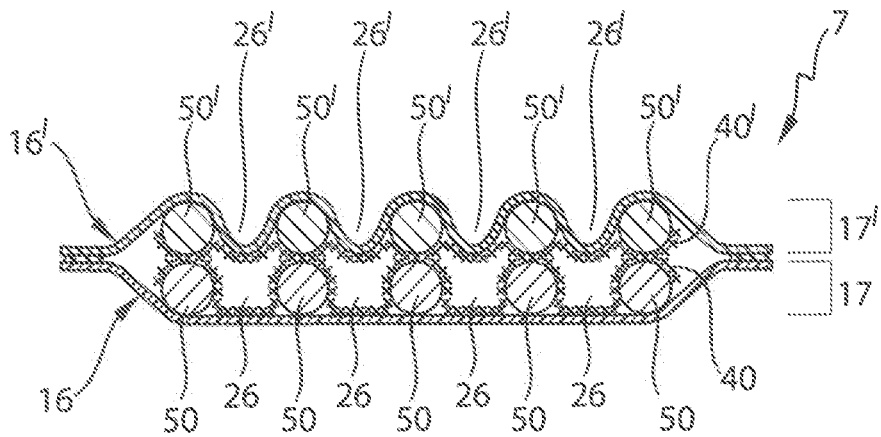
FIG. 6 shows a cross sectional view of an alternative absorbent core in accordance with one non-limiting embodiment.
Figure 9:
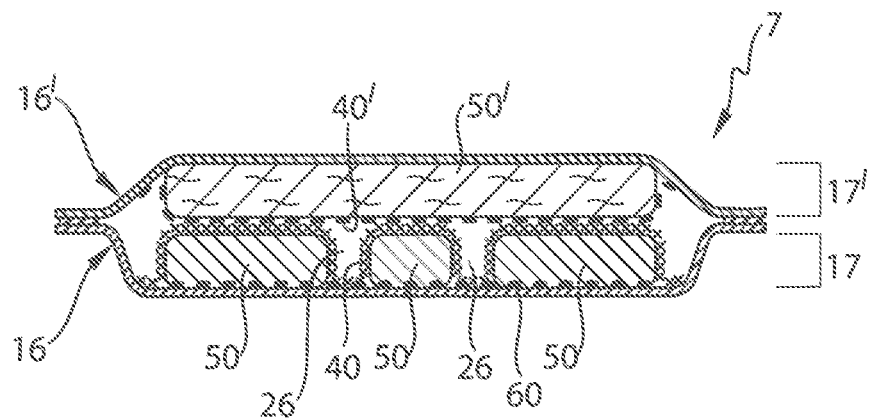
FIG. 9 shows a cross sectional view of an alternative absorbent core in accordance with one non-limiting embodiment.
Figure 10:
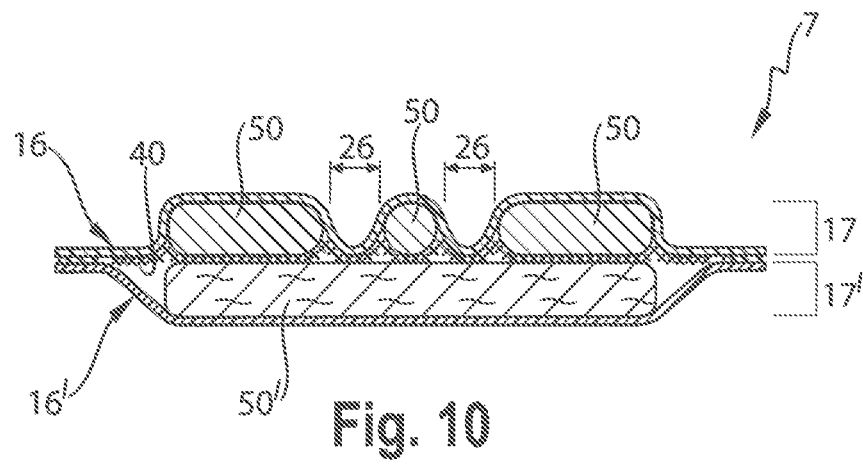
FIG. 10 shows a cross sectional view of an alternative absorbent core in accordance with one non-limiting embodiment.
Figure 11:
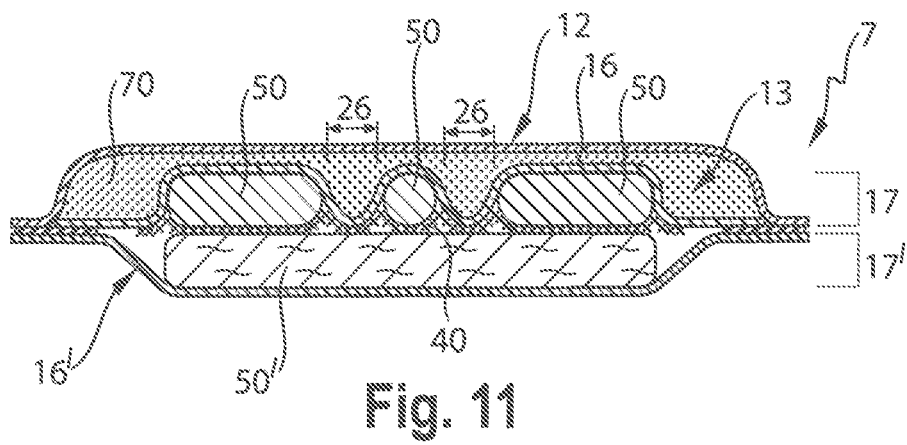
FIG. 11 shows a cross sectional view of an alternative absorbent core in accordance with one non-limiting embodiment.
Figure 12:
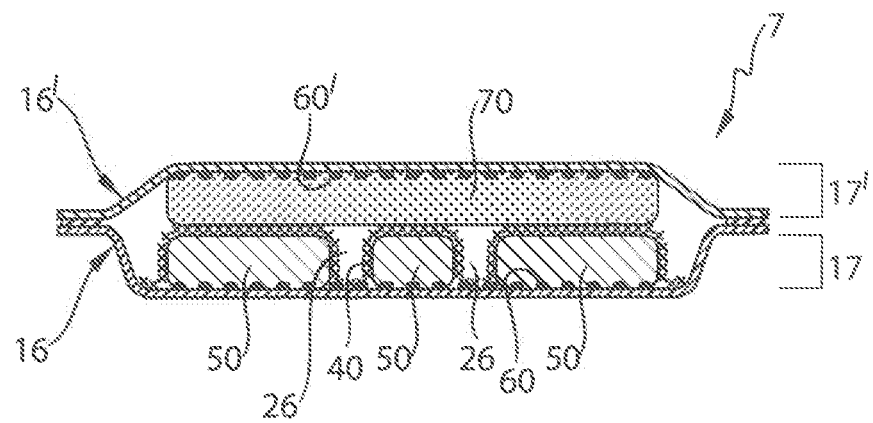
FIG. 12 shows a cross sectional view of an alternative absorbent core in accordance with one non-limiting embodiment.

As for example shown in FIGS. 5 and 9, one or more adhesive material(s) (60) may be present between said supporting sheet (16) and said absorbent layer (17), or parts thereof (e.g. herein referred to as, "second adhesive material"). For example, an adhesive material is applied to portions of said supporting sheet (16) that are to coincide with the channels (26), so that in said channels the supporting sheet can be bonded with said adhesive to the walls of the channel, or part thereof or to a further material, as described herein; and/or the adhesive may be applied to portions of the supporting sheet (16) that are to coincide with the absorbent material (50), to immobilize said material and avoid extensive migration thereof into said channels; the adhesive may be applied over substantially the whole surface area of the supporting sheet (16), e.g. substantially continuously and/or homogeneously. This may for example be a hotmelt adhesive applied by printing, slot coating or spraying.

In addition, or alternatively, the absorbent structure (13) may comprise one or more adhesive materials (40) applied on said absorbent layer (17) or part thereof, that is already supported by said supporting sheet (16), (herein referred to as "first adhesive material") e.g. after said absorbent material (50) is combined with/deposited on said supporting sheet (16) to form an absorbent layer (17). This may for example be a thermoplastic fibrous adhesive, as described herein after. It some embodiments, this may be applied continuously over the absorbent layer (17), hence over the absorbent material (50) and in the channels (26), to immobilize the absorbent layer and to optionally also adhere the supporting sheet in said channel, as described above. This is for example shown in FIGS. 5 to 11.

It should be understood that the first and second adhesive material may be the same type of adhesive, for example as a thermoplastic hotmelt adhesive, for example as described below, the difference between the first and second adhesive thus being the location where it is applied.

In some embodiments, said one or more adhesive material are at least present in the channels (26), for example at least said first adhesive material, or both said first and second adhesive material. It may thus be present on the longitudinal walls of the channels (26) (extending the height of the absorbent layer (17) and the length thereof). If the supporting sheet (16) material folds into said channels (26), or part thereof, e.g. the supporting sheet (16) has undulations into said channels (26) or part thereof, said undulations may be fixed to said walls or part thereof, to ensure the channels (26) are maintained (at least partially) during use. This is for example shown in FIGS. 10 and 11

The first and second channels (26) may be mirror images of one another with respect to the central longitudinal axis (X-axis) of the absorbent layer (17)/structure.

In some embodiments, and as for example shown in the Figures, there is no channel (26) that coincides with said longitudinal axis of said absorbent layer (17). The channels (26) may be spaced apart from one another over their whole longitudinal dimension. The smallest spacing distance D may for example be at least 5% of average transverse dimension W of layer, or for example at least 10% of W, or at least 15% of W; or for example may be at least 5 mm, or for example at least 8 mm.

Furthermore, in order to reduce the risk of fluid leakages, the longitudinal main channels (26) typically do not extend up to any of the transverse edges (19) and/or longitudinal edges (18) of the absorbent layer (17), as for example shown in the Figures. Typically, the smallest distance I between a channel (26) and the nearest longitudinal edge corresponds to at least 5% of W, or for example to at least 10% of W. In some embodiments, the distance is for example at least 10 mm; the smallest distance F between a channel and the nearest transverse edge (19) of the absorbent layer (17) may for example be at least 5% of the average length L of the layer.

Figure 2C:
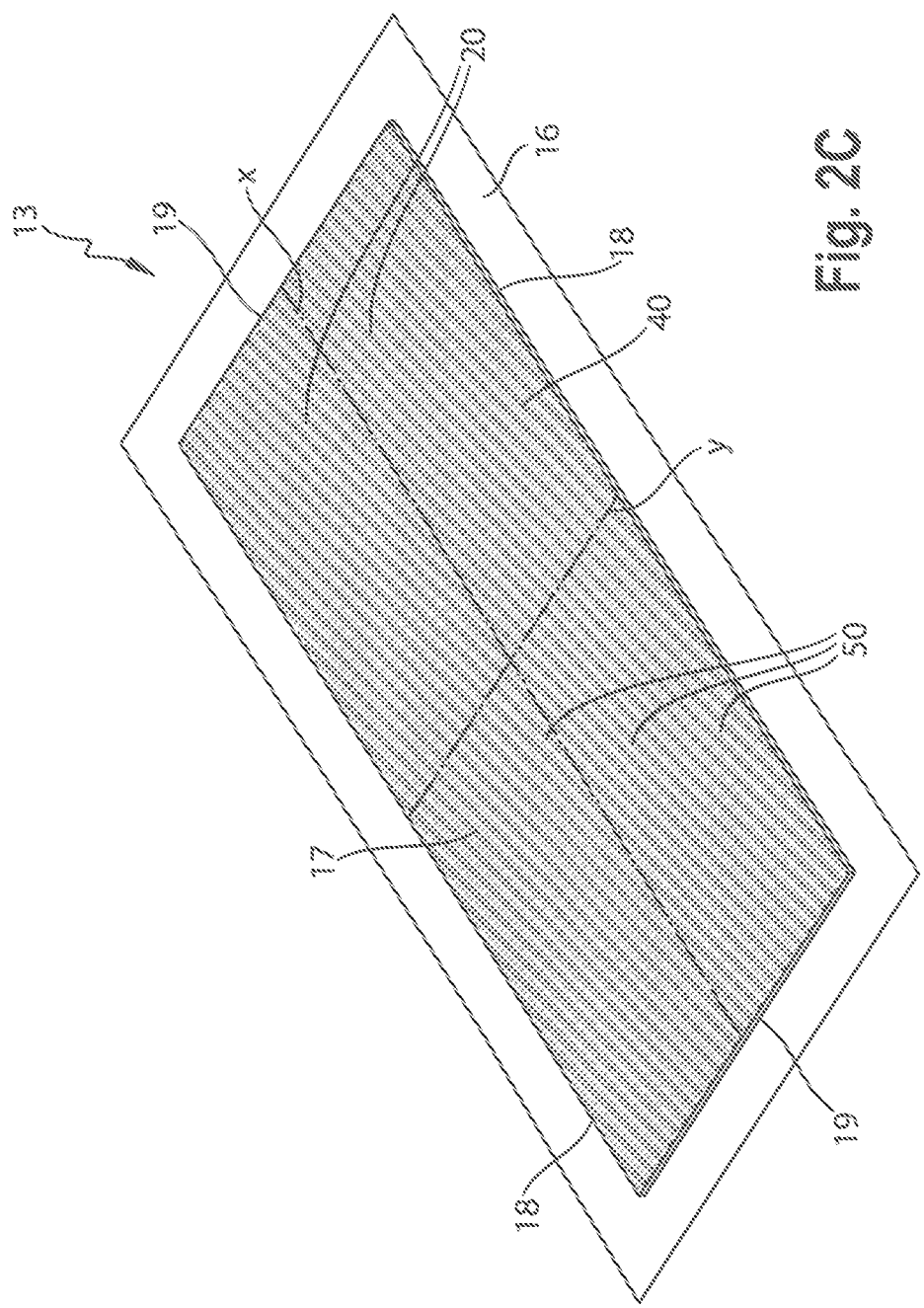
FIG. 2C shows a perspective view of an absorbent structure that may be combined with the absorbent structure in accordance with one non-limiting embodiment.

The absorbent structure may comprise only two channels, for example only in the front region, such as for example shown in FIG. 2B, or for example in the central (crotch) region, and optionally extending into the front and/or back region, such as shown FIG. 2A.

Figure 3B:
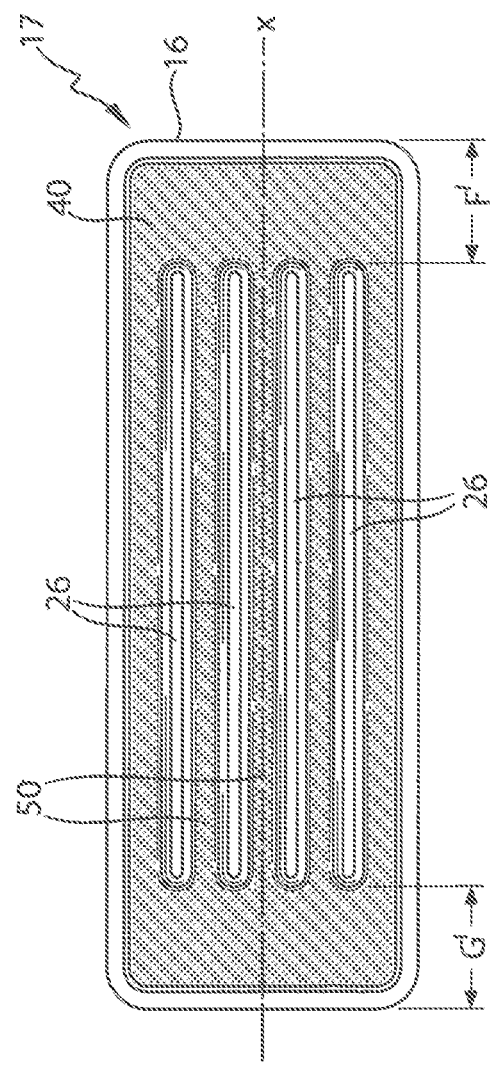
FIG. 3B shows a perspective view of an alternative absorbent structure in accordance with one non-limiting embodiment.

The absorbent structure (13) may comprise more than two of such channels (26), for example at least 4, or at least 5 or at least 6. Some or all of these may be substantially parallel to one another, for example being all straight and completely longitudinally, and/or two or more or all may be mirror images of one another in the longitudinal axis, or two or more may be curved or angled and for example mirror images of one another in the longitudinal axis, and two or more may be differently curved or straight, and for example mirror images of one another in the longitudinal axis. This is for example shown in FIGS. 3A and 3B.

Figure 4B:
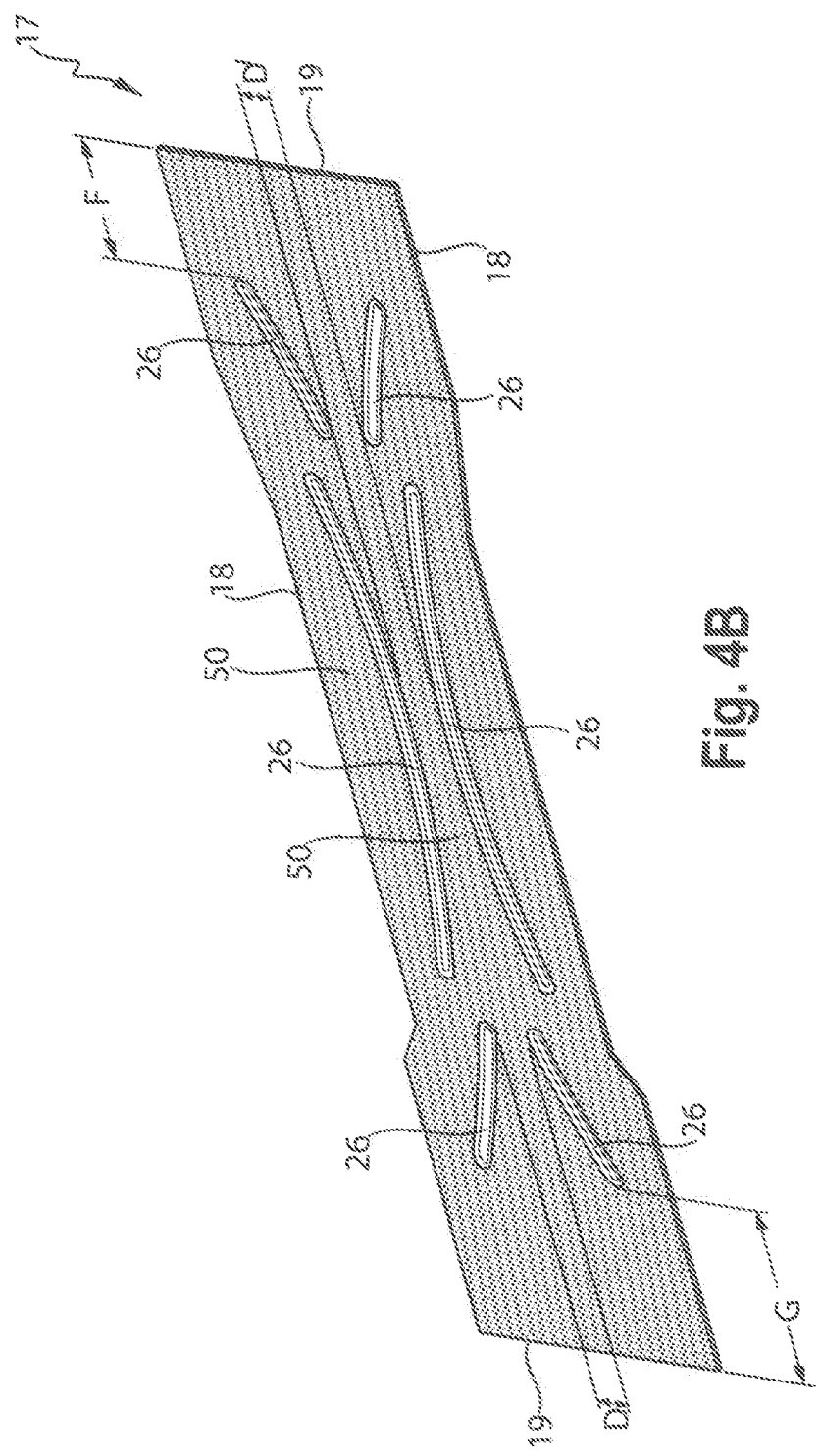
FIG. 4B shows a perspective view of an alternative absorbent layer in accordance with one non-limiting embodiment.

For example the front region of the absorbent layer (17) may comprise two or more channels (26), that are typically mirror images of one another in the longitudinal axis of the layer, and the crotch region may comprise two or more channels (26), that are typically mirror images of one another in the longitudinal axis of the layer, for example shown in FIG. 4A, and the latter may optionally extend into the front region and/or back region, with any of applicable dimensions and other characteristics described above. Optionally, further channel(s) may be present in the back region, for example two, such as for example shown in FIG. 4B.

The first and second channels (26), and optionally further channels (26), may be positioned in said absorbent layer (17) such that there is a central longitudinal strip, coinciding with said longitudinal axis, which is free of any channels (26); said absorbent material (50) may be substantially continuously present in said strip. For example, said strip may have a minimum width D of at least 5% of W, or at least 10% of W, and/or for example at least 5 mm, or at least 10 mm or at least 15 mm, and/or even up to 40 mm.

In some embodiments, in said central longitudinal strip between two neighboring channels (26) the average basis weight of absorbent material (50), or of said superabsorbent polymer material, is at least 350, and for example up to 1000 grams per m$^2$, or for example from 450 grams per m$^2$, and for example up to 750 grams per m$^2$.

In some embodiments, adjacent each first and second channel, and optionally adjacent said further channel(s), said absorbent material (50) is substantially continuously present.

The absorbent structure (13) typically comprises one or more further material(s) (e.g. a further material layer) to cover the absorbent layer (17), herein referred to as further material; the further material may be a layer comprising adhesive, for example on the surface that is to contact the absorbent layer (17) of the absorbent structure (13) herein. Thus, the further material may comprise, on the surface to be placed adjacent said absorbent layer (17) of the absorbent structure (13), an adhesive material.

The resulting structure is herein referred to as "absorbent core (7)". Examples thereof are shown in FIGS. 5 to 13.

This further material may be a further absorbent structure (13'), with a second absorbent layer (17') and a second supporting sheet (16'), so that both absorbent layers (17, 17') are sandwiched between said supporting sheets (16; 16'); this may be a further absorbent structure (13') of the disclosure, with two or more channels (26') as described herein, and for example shown in FIGS. 5, 6, 7, 8; or this may be a absorbent structure as described herein but without channels, such as for example shown in FIG. 9; and/or it may be an absorbent structure as described herein but without adhesive.

The second absorbent structure (13') may be identical to the first absorbent structure (13), or they may both be absorbent structure with channels (26; 26') of the disclosure, but they may be different, for example having different channels, different number of channels (such as for example shown in FIG. 8), different adhesive, different adhesive application or combinations thereof.

The channels (26), or some of those, of the first absorbent structure (13) and the channels (26') of the second absorbent structure (13'), or some of those, may coincide and overlap with one another; e.g. completely or for example coincide only partially and overlap only partially; or some or all of the channels (26; 26') may even not coincide and not overlap one another. In some embodiments they are about identical to one another and the channels (26) of one structure substantially completely coincide and overlap the channels (26) of another structure. This is for example shown in FIG. 12.

In some embodiments, the further material may be a part of the supporting sheet (16), which is folded over the absorbent layer (17) and then sealed along the peripheral edges, to enclose the absorbent layer (17).

In some embodiments, the further material is a further supporting sheet (16'), i.e. the absorbent structure (13) is covered with a further supporting sheet (16'), said absorbent layer then being sandwiched between the two supporting sheets.

In some embodiments, the further material may be an acquisition material layer (70) and/or an acquisition sheet (12), for example sealed to said supporting sheet (16). In some embodiments, the further material includes a further absorbent structure, e.g. any of those described above, or further supporting sheet (16'), and then combined with an acquisition material layer (70), and optionally a further acquisition sheet (12). This is for example shown in FIG. 11.

Figure 13:
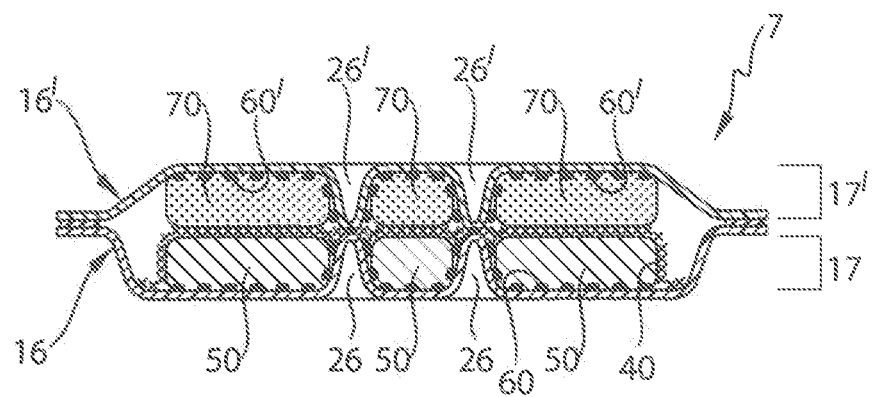
FIG. 13 shows a cross sectional view of an alternative absorbent core in accordance with one non-limiting embodiment.
Figure 14:
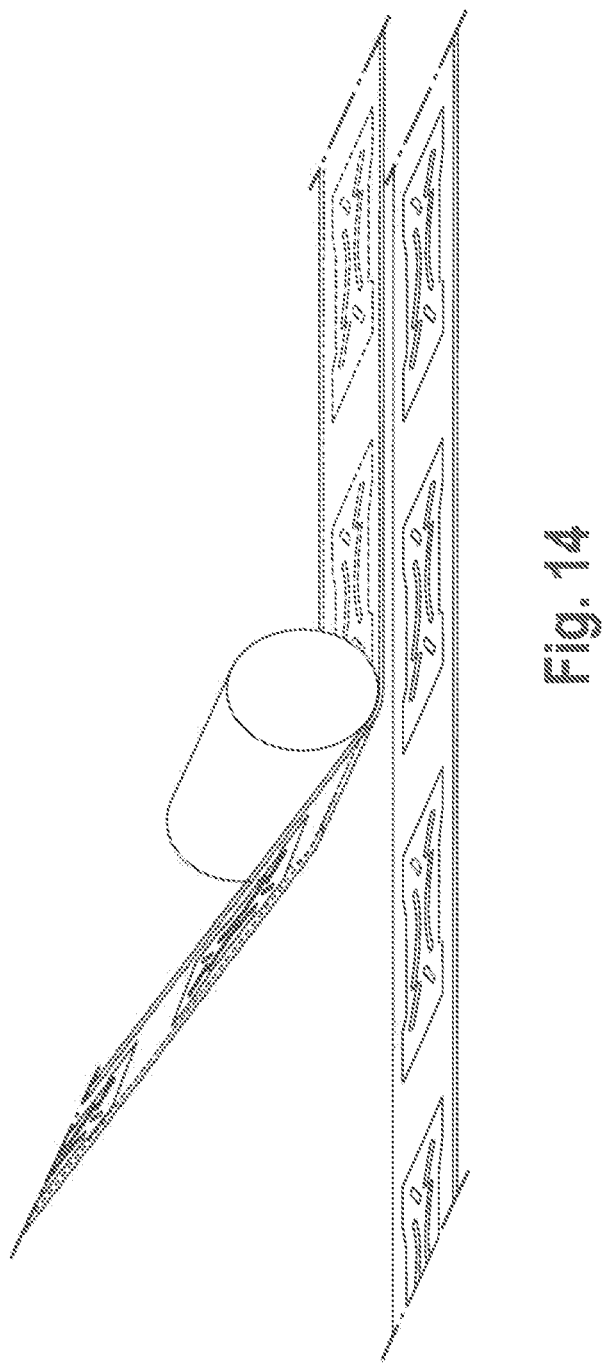
FIG. 14 shows a method/apparatus of forming an absorbent core in accordance with one non-limiting embodiment comprising two absorbent structures of the disclosure.

The further material may also be an acquisition material layer (70) present adjacent said absorbent layer (17), the acquisition material layer (70) optionally comprising chemically cross-linked cellulosic fibers, and the acquisition material layer being supported on a second supporting sheet (16'). The absorbent layer (17) and the acquisition material layer (70) may then be sandwiched between said supporting sheet (16) of the first structure and said second supporting sheet (16'), as exemplary shown in FIG. 12. The acquisition material layer (70) may also further comprise channels (26'), in particular substantially completely overlapping with the channels (26) of said first absorbent structure (13) as shown in FIG. 13.

The supporting sheet (16) of the first structure and/or the second supporting sheet (16') of the acquisition material layer (70) may fold into the channels (26) of the first absorbent structure (13) and/or optionally into the channels (26') of the acquisition material layer (70), if present, or part of these channels (26,26'). The one or more adhesive material(s) may be at least present in the channels (26, 26'), or part thereof, and the supporting sheets (16; 16') may be adhered to one another in said channels (26, 26') by one or more of these adhesive material(s). Another second adhesive (60') may be present between the second supporting sheet (16') and the acquisition material layer (70). Another adhesive (not represented) may be placed between the acquisition material layer (70) and the absorbent layer (17), in addition to the thermoplastic adhesive (40), to improve better adhesion of both layers.

In any of these cases, the further material, can then be sealed to the supporting sheet (16) along the peripheral edges thereof, to enclose the absorbent layer (s) (17; optionally 17').

In any of these cases the supporting sheet (16) or acquisition layer/sheet may fold into (i.e. undulate into) said channels (26) or part thereof. This is shown for example in FIGS. 6, 7, 8.

It may be adhered to the supporting sheet (16) of the absorbent structure (13) of the disclosure in said channels (26), e.g. by an adhesive material, as described herein. Alternatively, or in addition, it may be adhered to the walls of the channels (26 and/or 26') or part thereof.

In some embodiments the absorbent structure (13) comprises such a further material overlaying said absorbent layer (17), and a pressure means is applied selectively to said supporting sheet (16) and/or to said further material, in those parts that coincide with said channels (26 and/or 26'), to pressurize said supporting sheet (16) and/or said further material into said channels of the absorbent structure (13) and/or into the channels of a further (second) absorbent structure 913') if present (so: into channels 26 and/or 26', if present), to aid formulation of said undulations and/or to aid adhering of the further material and said supporting sheet (16) to one another in said channels (26 and/or 26'), if an adhesive material is present as described herein.

The pressure means may be a pressure roll with raised portions that have substantially the size, shape, pattern of said channels (26 and/or 26'), that can coincide (i.e.: mate) with said parts of the supporting sheet (16) or further material coinciding with said channels (26 and/or 26'). In some embodiments, the further (e.g. second) supporting sheet (16') may be wider than the absorbent structure to enable the second supporting sheet (16') to fold into the channels (26 and/or 26') or part thereof, and thereby may adhere to the first supporting sheet (16). This is for example shown in FIGS. 6, 7 and 8.

In embodiments wherein the absorbent core (7) comprises two (or more) absorbent structures (13; 13') comprising the channels (26; 26'), described herein, it may be that one or two, or more, or all, of the channels (26) of one absorbent structure (13) substantially superpose the channels (26') of the adjacent absorbent structure (13'). The resulting absorbent core (7) is then a laminate of absorbent structures (13'; 13') with channels (26; 26'), wherein the channels (26;26') extend substantially through the thickness of the absorbent layers (17;17'). This is for example shown in FIG. 12.

In addition or alternatively, it may be that one or two, or more, or all, channels (26) of one absorbent structure (13) do not superpose the channels (26') of the adjacent absorbent structure (13'); they may for example be complementary with the channels (26) of the adjacent structure. By complementary it is meant that the channels (26') of the second absorbent structure (13') form an extension of the channels (26) of the first absorbent structure (13).

In some embodiments, the absorbent core (7) may comprise two or more absorbent structures (13), one of which being the structure of the disclosure, and one being an absorbent structure (13) with a supporting sheet (16') with thereon an absorbent layer (17') (with superabsorbent polymer material) without channels and/or without adhesive.

If a second absorbent structure (13') is present in the absorbent core (7), this may comprise one or more adhesives, in the manner as described above, and for the reasons described above.

For example, it may be present such that it coincides with the channels (26) of the first absorbent structure (13) at least, and/or with its channels (26'), if present.

Absorbent Material (50)

The absorbent layer (17) comprises absorbent material (50) that comprises superabsorbent polymer material (e.g. particles), optionally combined with cellulosic material (including for example cellulose, comminuted wood pulp in the form of fibers). The further material described above (e.g. a further, second absorbent structure (13') may include an absorbent material, and the following may apply thereto too.

In some embodiment, the absorbent material (50) may comprise at least 60%, or at least 70% by weight of superabsorbent polymer material, and at the most 40% or at the most 30% of cellulosic material.

In some other embodiments, the absorbent layer (17) comprises absorbent material (50) that consists substantially of absorbent polymer material, e.g. particles, e.g. less than 5% by weight (of the absorbent material (50)) of cellulosic material is present; and said absorbent layer (17)/absorbent structure (13), may be free of cellulosic material.

Typically, the superabsorbent polymer material is in the form of particles. Suitable for use in the absorbent layer (17) can comprise any superabsorbent polymer particles known from superabsorbent literature, for example such as described in Modern Superabsorbent Polymer Technology, F. L. Buchholz, A. T. Graham, Wiley 1998. The absorbent polymer particles may be spherical, spherical-like or irregular shaped particles, such as Vienna-sausage shaped particles, or ellipsoid shaped particles of the kind typically obtained from inverse phase suspension polymerizations. The particles can also be optionally agglomerated at least to some extent to form larger irregular particles.

In some embodiments herein, the absorbent material (50) as a whole and/or said particulate superabsorbent polymer material at least, has a high sorption capacity, e.g. having a CRC of for example at least 20 g/g, or at 30 g/g. Upper limits may for example be up to 150 g/g, or up to 100 g/g.

In some embodiments herein, the absorbent material (50) comprising or consisting of superabsorbent polymer particles that are formed from polyacrylic acid polymers/polyacrylate polymers, for example having a neutralization degree of from 60% to 90%, or about 75%, having for example sodium counter ions.

The superabsorbent polymer may be polyacrylates and polyacrylic acid polymers that are internally and/or surface cross-linked. Suitable materials are described in the PCT Patent Application WO 07/047598 or for example WO 07/046052 or for example WO2009/155265 and WO2009/155264. In some embodiments, suitable superabsorbent polymer particles may be obtained by current state of the art production processes as is more particularly described in WO 2006/083584. The superabsorbent polymers may be internally cross-linked, i.e. the polymerization is carried out in the presence of compounds having two or more polymerizable groups which can be free-radically copolymerized into the polymer network. Useful crosslinkers include for example ethylene glycol dimethacrylate, diethylene glycol diacrylate, allyl methacrylate, trimethylolpropane triacrylate, triallylamine, tetraallyloxyethane as described in EP-A 530 438, di- and triacrylates as described in EP-A 547 847, EP-A 559 476, EP-A 632 068, WO 93/21237, WO 03/104299, WO 03/104300, WO 03/104301 and in DE-A 103 31 450, mixed acrylates which, as well as acrylate groups, include further ethylenically unsaturated groups, as described in DE-A 103 31 456 and DE-A 103 55 401, or crosslinker mixtures as described for example in DE-A 195 43 368, DE-A 196 46 484, WO 90/15830 and WO 02/32962 as well as cross-linkers described in WO2009/155265. The superabsorbent polymer particles may be externally surface cross-linked, or: post cross-linked).

Useful post-crosslinkers include compounds including two or more groups capable of forming covalent bonds with the carboxylate groups of the polymers. Useful compounds include for example alkoxysilyl compounds, polyaziridines, polyamines, polyamidoamines, di- or polyglycidyl compounds as described in EP-A 083 022, EP-A 543 303 and EP-A 937 736, polyhydric alcohols as described in DE-C 33 14 019, cyclic carbonates as described in DE-A 40 20 780, 2-oxazolidone and its derivatives, such as N-(2-hydroxyethyl)-2-oxazolidone as described in DE-A 198 07 502, bis- and poly-2-oxazolidones as described in DE-A 198 07 992, 2-oxotetrahydro-1,3-oxazine and its derivatives as described in DE-A 198 54 573, N-acyl-2-oxazolidones as described in DE-A 198 54 574, cyclic ureas as described in DE-A 102 04 937, bicyclic amide acetals as described in DE-A 103 34 584, oxetane and cyclic ureas as described in EP-A 1 199 327 and morpholine-2,3-dione and its derivatives as described in WO 03/031482.

The superabsorbent polymers or particles thereof may have surface modifications, such as being coated or partially coated with a coating agent. Examples of coated absorbent polymer particles are disclosed in WO2009/155265. The coating agent may be such that it renders the absorbent polymer particles more hydrophilic. For example, it may be hydrophilic (i.e., fumed) silica, such as Aerosils. The coating agent may be a polymer, such as an elastic polymer or a film-forming polymer or an elastic film-forming polymer, which forms an elastomeric (elastic) film coating on the particle. The coating may be a homogeneous and/or uniform coating on the surface of the absorbent polymer particles. The coating agent may be applied at a level of from 0.1% to 5%.

The superabsorbent polymer particles may have a particle sizes in the range from 45 µm to 4000 µm, more specifically a particle size distribution within the range of from 45 µm to about 2000 µm, or from about 100 µm to about 1000 or to 850 µm. The particle size distribution of a material in particulate form can be determined as it is known in the art, for example by means of dry sieve analysis (EDANA 420.02 "Particle Size distribution).

In some embodiments herein, the superabsorbent material is in the form of particles with a mass medium particle size up to 2 mm, or between 50 microns and 2 mm or to 1 mm, or from 100 or 200 or 300 or 400 or 500 µm, or to 1000 or to 800 or to 700 µm; as can for example be measured by the method set out in for example EP-A-0691133. In some embodiments of the disclosure, the superabsorbent polymer material is in the form of particles whereof at least 80% by weight are particles of a size between 50 µm and 1200 µm and having a mass median particle size between any of the range combinations above. In addition, or in another embodiment of the disclosure, said particles are essentially spherical. In yet another or additional embodiment of the disclosure the superabsorbent polymer material has a relatively narrow range of particle sizes, e.g. with the majority (e.g. at least 80%, at least 90% or even at least 95% by weight) of particles having a particle size between 50 µm and 1000 µm, between 100 µm and 800 µm, between 200 µm and 600 µm.

Supporting Sheet (16; 16')

The absorbent structure (13) herein comprises a supporting sheet (16) on which said absorbent material (50) is supported and immobilized. The further material may be or include a supporting sheet (16'), and the following applies also to such a sheet (16').

This supporting sheet (16) may be an individual sheet or a web material that is subsequently divided in to individual absorbent structure (13)s, in particular paper, films, wovens or nonwovens, or laminate of any of these.

In some embodiments herein, the supporting sheet (16) is a nonwoven, e.g. a nonwoven web, such as a carded nonwoven, spunbond nonwoven or meltblown nonwoven, and including nonwoven laminates of any of these.

The fibers may be of natural or man-made origin and may be staple or continuous filaments or be formed in situ. Commercially available fibers have diameters ranging typically from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). The fibers may be bicomponent fibers, for example having a sheath-core arrangement, e.g. with different polymers forming the sheath and the core. Nonwoven fabrics can be formed by many processes such as meltblowing, spunbonding, solvent spinning, electrospinning, and carding. The basis weight of nonwoven fabrics is usually expressed in grams per square meter (gsm).

The nonwoven herein may be made of hydrophilic fibers; "Hydrophilic" describes fibers or surfaces of fibers, which are wettable by aqueous fluids (e.g. aqueous body fluids) deposited on these fibers. Hydrophilicity and wettability are typically defined in terms of contact angle and the strike through time of the fluids, for example through a nonwoven fabric. This is discussed in detail in the American Chemical Society publication entitled "Contact angle, wettability and adhesion", edited by Robert F. Gould (Copyright 1964). A fiber or surface of a fiber is said to be wetted by a fluid (i.e. hydrophilic) when either the contact angle between the fluid and the fiber, or its surface, is less than 90°, or when the fluid tends to spread spontaneously across the surface of the fiber, both conditions are normally co-existing. Conversely, a fiber or surface of the fiber is considered to be hydrophobic if the contact angle is greater than 90° and the fluid does not spread spontaneously across the surface of the fiber.

The supporting sheet (16) herein may be air-permeable. Films useful herein may therefore comprise micro pores. Nonwovens herein may for example be air permeable. The supporting sheet (16) may have for example an air-permeability of from 40 or from 50, to 300 or to 200 $m^3/(m^2 \times min)$, as determined by EDANA method 140-1-99 (125 Pa, 38.3 cm 2). The supporting sheet (16) may alternatively have a lower air-permeability, e.g. being non-air-permeable, to for example be better detained on a moving surface comprising vacuum.

In some executions, the supporting sheet (16) is a nonwoven laminate material, a nonwoven laminate web, for example of the SMS or SMMS type.

In order to form easily said undulations, the supporting sheet (16) may have a basis weight that is less than 60 gsm, or for example than 50 gsm, for example from 5 gsm to 40 gsm, or to 30 gsm.

The supporting sheet (16) may have a CD-extensibility or a MD-extensibility.

In one of the embodiment herein, the supporting sheet (16) has undulations that fold (undulate) into said first and second channels (26), and optionally in to said further channel(s), of part thereof. For example the undulations may extend over about the full longitudinal dimension of the channel; they may for example extend to complete average height of the absorbent layer (17)/channel, or for example only up to 75% thereof, or up to 50% of the average height of the absorbent layer (17)/channel. This aids immobilization of the absorbent material (50) adjacent said channels (26) and said channels (26) of said layers.

The undulations may be adhered with said one or more adhesive material, e.g. said second adhesive material, to said walls of said channels (26). The supporting sheet (16) may alternatively, or in addition, be adhered in said channels (26) to said further material, e.g. second supporting sheet (16), describe herein above, e.g. with said first and/or second adhesive.

Adhesive Material

The absorbent structure (13) may comprise one or more adhesive materials. In some embodiments, it comprises a first adhesive material and/or a second adhesive material, as described above, and in the manner described above.

The absorbent core herein may comprise a further second absorbent structure (13') that may comprise one or more adhesive materials; the following equally applies thereto.

Any suitable adhesive can be used for this, for example so-called hotmelt adhesives used. For example, a sprayable hot melt adhesives, such as H.B. Fuller Co. (St. Paul, MN) Product No. HL-1620-B, can be used.

The adhesive material(s) may not only help in immobilizing the absorbent material on the supporting sheet but it may also help in maintaining the integrity of the channels in the absorbent structure absorbent core during storage and/or during use of the disposable article. The adhesive material may help to avoid that a significant amount of absorbent material migrates into the channels. Furthermore, when the adhesive material is applied in the channels or on the supporting sheet portions coinciding with the channels it may thereby help to adhere the supporting sheet of the absorbent structure to said walls, and/or to a further material, as will be described in further details below.

In some embodiments, the first adhesive (40) and/or the second adhesive (60) may be a thermoplastic adhesive material.

In some embodiments, the first adhesive (40) may be applied as fibers, forming a fibrous network that immobilizes the absorbent material on the supporting sheet. The thermoplastic adhesive fibers may be partially in contact with the supporting sheet of the absorbent structure; if applied also in the channels, it (further) anchors the absorbent layer to the supporting sheet.

The thermoplastic adhesive material may for example allow for such swelling, without breaking and without imparting too many compressive forces, which would restrain the absorbent polymer particles from swelling. Thermoplastic adhesive materials (40; 60) suitable for use in the present disclosure includes hot melt adhesives comprising at least a thermoplastic polymer in combination with a plasticizer and other thermoplastic diluents such as tackifying resins and additives such as antioxidants. Exemplary suitable hot melt adhesive materials (40; 60) are described in EP 1447067 A2. In some embodiments, the thermoplastic polymer has a molecular weight (Mw) of more than 10,000 and a glass transition temperature (Tg) below room temperature or −6° C.>Tg<16° C. In certain embodiments, the concentrations of the polymer in a hot melt are in the range of about 20 to about 40% by weight. In certain embodiments, thermoplastic polymers may be water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof.

Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alpha olefins.

The thermoplastic adhesive material, typically a hot-melt adhesive material, is generally present in the form of fibres, i.e. the hot melt adhesive can be fiberized. In some embodiments, the thermoplastic adhesive material forms a fibrous network over the absorbent polymer particles. Typically, the fibres can have an average thickness from about 1 µm to about 100 µm, or from about 25 µm to about 75 µm, and an average length from about 5 mm to about 50 cm. In particular the layer of hot melt adhesive material can be provided such as to comprise a net-like structure. In certain embodiments the thermoplastic adhesive material is applied at an amount of from 0.5 to 30 g/m$^2$, or from 1 to 15 g/m$^2$, or from 1 and 10 g/m$^2$ or even from 1.5 and 5 g/m$^2$ per supporting sheet (16).

A typical parameter for an adhesive suitable for use in the present disclosure can be a loss angle tan Delta at 60° C. of below the value of 1, or below the value of 0.5. The loss angle tan Delta at 60° C. is correlated with the liquid character of an adhesive at elevated ambient temperatures. The lower tan Delta, the more an adhesive behaves like a solid rather than a liquid, i.e. the lower its tendency to flow or to migrate and the lower the tendency of an adhesive superstructure as described herein to deteriorate or even to collapse over time. This value is hence particularly important if the absorbent article is used in a hot climate.

It may be beneficial, e.g. for process reasons and/or performance reasons, that the thermoplastic adhesive material has a viscosity of between 800 and 4000 mPa s, or from 1000 mPa s or 1200 mPa s or from 1600 mPa s to 3200 mPa s or to 3000 mPa s or to 2800 mPa s or to 2500 mPa s, at 175° C., as measurable by ASTM D3236-88, using spindle 27, 20 rpm, 20 minutes preheating at the temperature, and stirring for 10 min.

The thermoplastic adhesive material may have a softening point of between 60° C. and 150° C., or between 75° C. and 135° C., or between 90° C. and 130° C., or between 100° C. and 115° C., as can be determined with ASTM E28-99 (Herzog method; using glycerine).

In one embodiment herein, the thermoplastic adhesive component may be hydrophilic, having a contact angle of less than 90°, or less than 80° or less than 75° or less than 70°, as measurable with ASTM D 5725-99.

Signals

The absorbent articles of the present invention may comprise signals that communicate to the consumer the functionality and benefits of the absorbent core channels. Non-limiting examples of such signals may include printed adhesive layers, backsheet graphics, embossing of the topsheet and/or acquisition layer, and combinations thereof.

One type of signal that may be used to communicate the existence and the benefits of the channels is a printed adhesive layer. In some embodiments, an article with channels in the core may have a layer of an adhesive that is applied in a pattern that connotes the absorbency and other benefits of the channels. This adhesive layer may be applied to a substrate, such as a supporting layer, in some embodiments an acquisition layer, that may be positioned between a topsheet and the absorbent core with channels. In some embodiments, the layer of printed adhesive may be visible through the topsheet.

In some embodiments, a fluid, such as an adhesive, may be applied or printed onto an advancing substrate. The fluid application apparatus may include a slot die applicator and a substrate carrier. The slot die applicator may include a slot opening, a first lip, and a second lip, the slot opening located between the first lip and the second lip. And the substrate carrier may include one or more pattern elements and may be adapted to advance the substrate past the slot die applicator as the slot die applicator discharges adhesive onto the substrate. In operation, when the first surface of the substrate is disposed on the substrate carrier, the substrate carrier advances the second surface of the substrate past the slot opening of the slot die applicator. In turn, the substrate is intermittently compressed between the slot die applicator and the pattern surface of the pattern element. As the substrate is intermittently compressed, adhesive discharged from the slot die applicator is applied onto the second surface of the advancing substrate in an area having a shape that is substantially the same as a shape defined by the pattern surface. In some embodiments, the adhesive may be a different color than the substrate. The adhesive may comprise pigments or dyes. Other methods and apparatuses involved for the application of adhesives in pre-determined patterns to an advancing substrate are disclosed in U.S. Pat. No. 8,186,296. In some embodiments, the fluid printed on the substrate may be an ink without an adhesive.

Figure 17A:
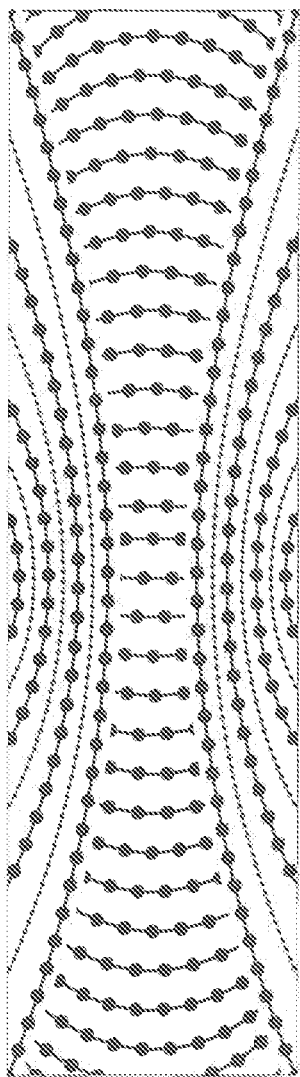
FIGS. 17A, 17B, 17C, and 18 show top view representations of non-limiting embodiments of printed adhesive patterns.
Figure 17B:
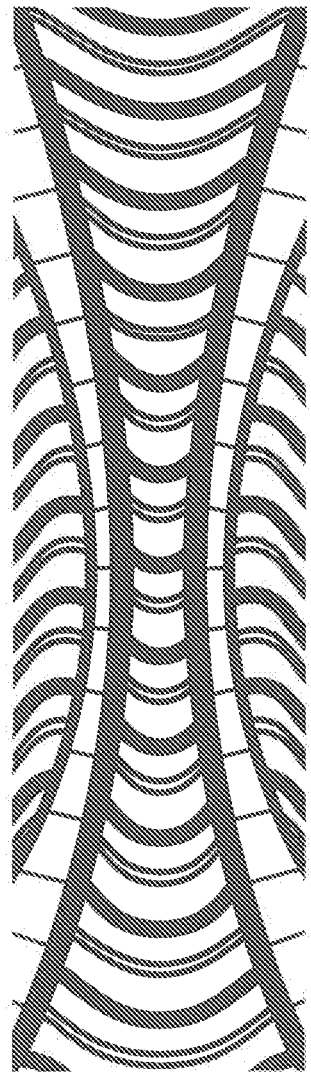
Figure 17C:
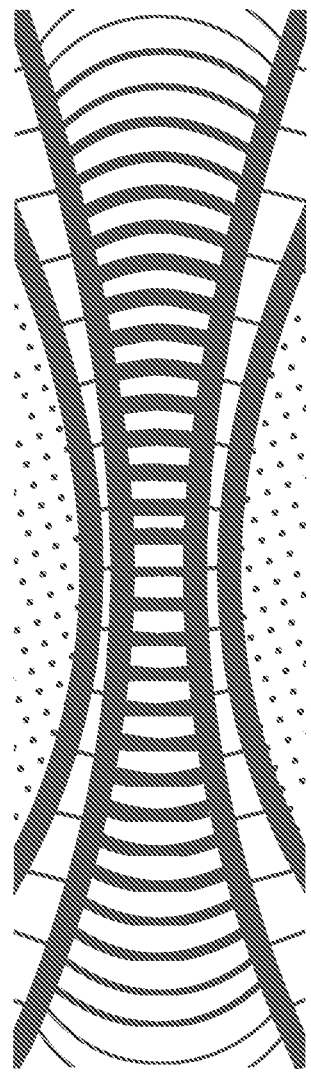
Figure 18:
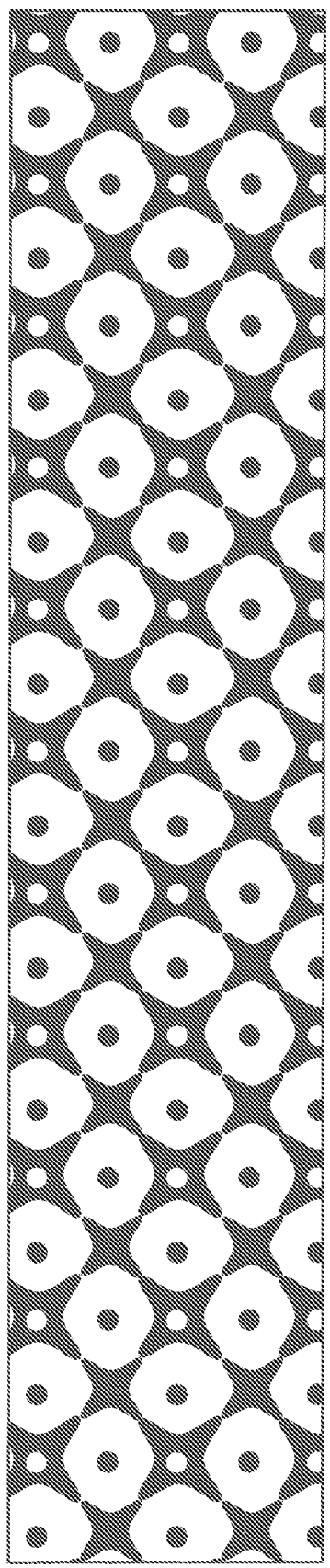

The term "pattern" as used herein means a decorative or distinctive design, not necessarily repeating or imitative, including but not limited to the following: marbled, check, mottled, veined, clustered, geometric, spotted, helical, swirl, arrayed, variegated, textured, spiral, cycle, contoured, laced, tessellated, starburst, lobed, lightning, blocks, textured, pleated, cupped, concave, convex, braided, tapered, and combinations thereof. Examples of patterns for the printed adhesive layer may be seen in FIGS. 17A, 17B, 17C, and 18. In FIGS. 17A to 17C, the curved lines of the printed adhesive layer, and in FIG. 18, the pattern of the printed adhesive layer, may signal to the consumer one or more benefits of the channels. For example, the channels may act as a conduit, distributing fluid to a more comfortable place, while the printed adhesive layer, visible to the caregiver through the topsheet, may signal or communicate the fluid distribution and comfort that the article can provide.

As discussed above, the absorbent structure of the present invention typically comprises one or more further materials, such as a further material layer, to cover the absorbent layer. This layer may comprise an adhesive, for example on the surface that is to contact the absorbent layer of the absorbent structure. Thus, the further material may comprise on the surface to be placed adjacent said absorbent layer of the absorbent structure, an adhesive material. In some embodiments, the further material layer may be an acquisition material layer that may have the adhesive printed onto it to form a patterned appearance. Thus, the adhesive is printed onto the surface of the acquisition layer that is adjacent to the absorbent core. In addition to an absorbent core with channels and a printed adhesive layer printed onto the surface of the acquisition layer adjacent to the absorbent core, the article may also comprise a topsheet, wherein the printed adhesive layer is visible through the topsheet. In some embodiments, the printing (ink or an adhesive with ink) may be on the topsheet itself, and where ink is the substance being printed, the printing may be performed using digital printing.

In some embodiments, the absorbent article may comprise graphics printed onto the backsheet. As the absorbent core is loaded with fluid, the absorbent material will expand in particular towards the backsheet, while the channels which do not comprise absorbent material will not expand. This difference may be used, as the channels will become more perceptible through the backsheet as fluid is absorbed as they may form depressions. These depressions will become more pronounced as the absorbent article absorbs the fluid.

The depth of these depressions formed by the channels on the backsheet side will be proportional to the amount of fluid absorbed, and the inventors have found that that the visual appearance to the caregiver may be improved by providing a backsheet printing which matches or at least indicates the region of the channels to the caregiver. Thus the backsheet printing may comprise a line or a curve which substantially matches the shape and/or position of the channels.

Figure 15:
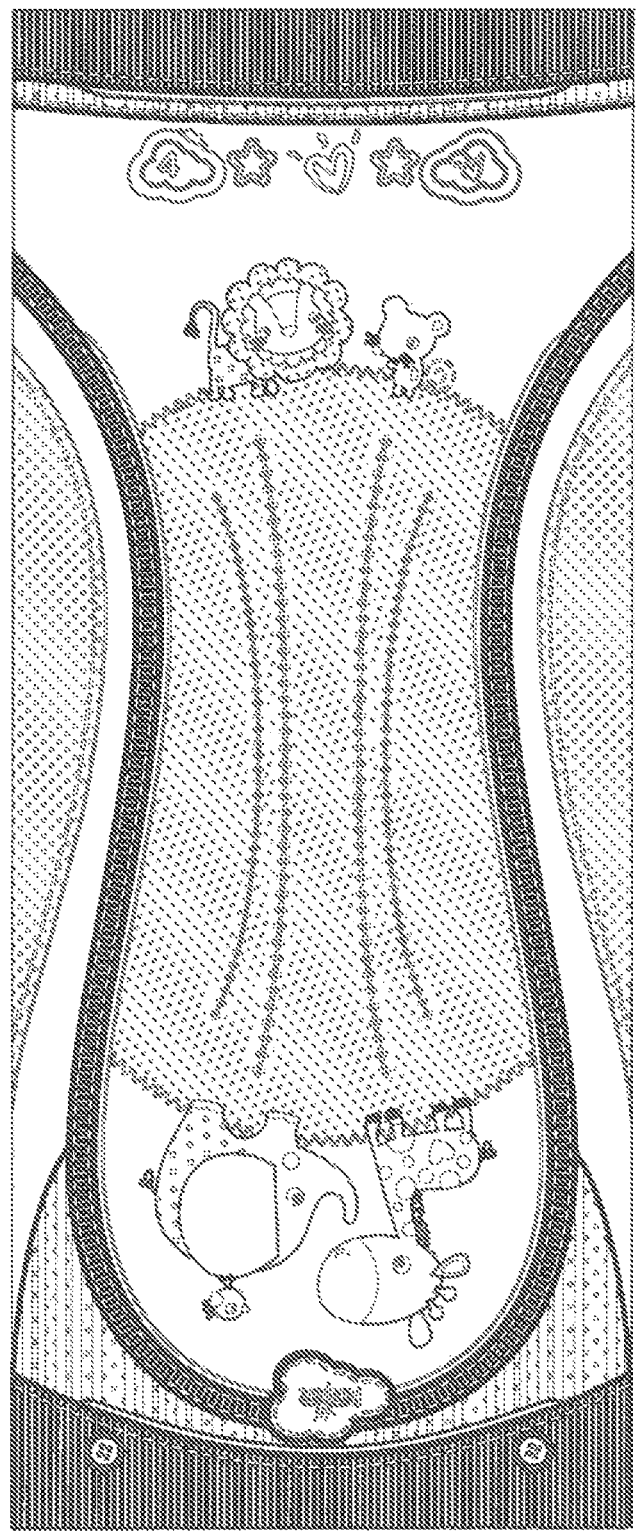
FIGS. 15 and 16 show plan views of non-limiting embodiments of an absorbent article of the present invention comprising backsheet graphics.
Figure 16:
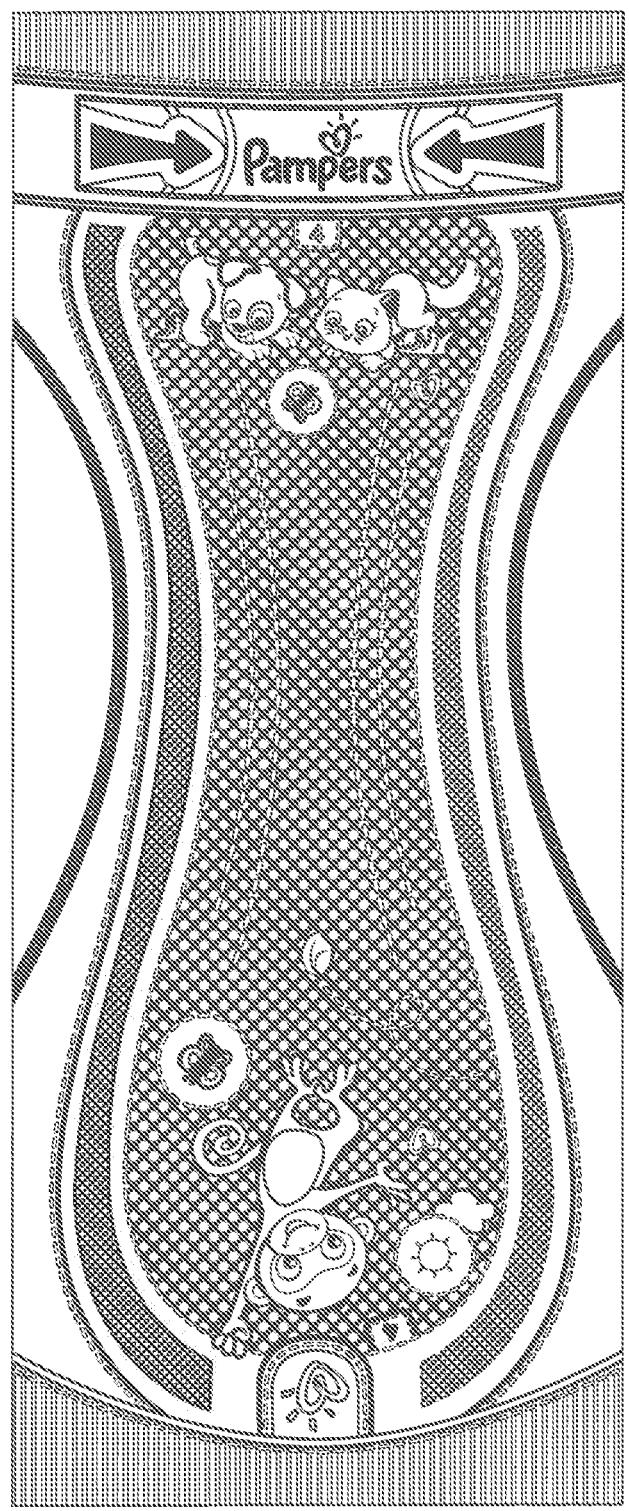

Backsheet graphics, for example, as shown in FIGS. 15 and 16, may similarly signal to the caregiver the attributes of the channels. In some embodiments, the only visual signal of the channels may be the backsheet printing. In some embodiments, the backsheet printing may be curves, lines, or other patterns that approximate the shape and contours of the channels. In some embodiments, the article may comprise both a printed adhesive layer and backsheet graphics, the combination of which work together or separately to accentuate certain channel aspects.

Figure 19:
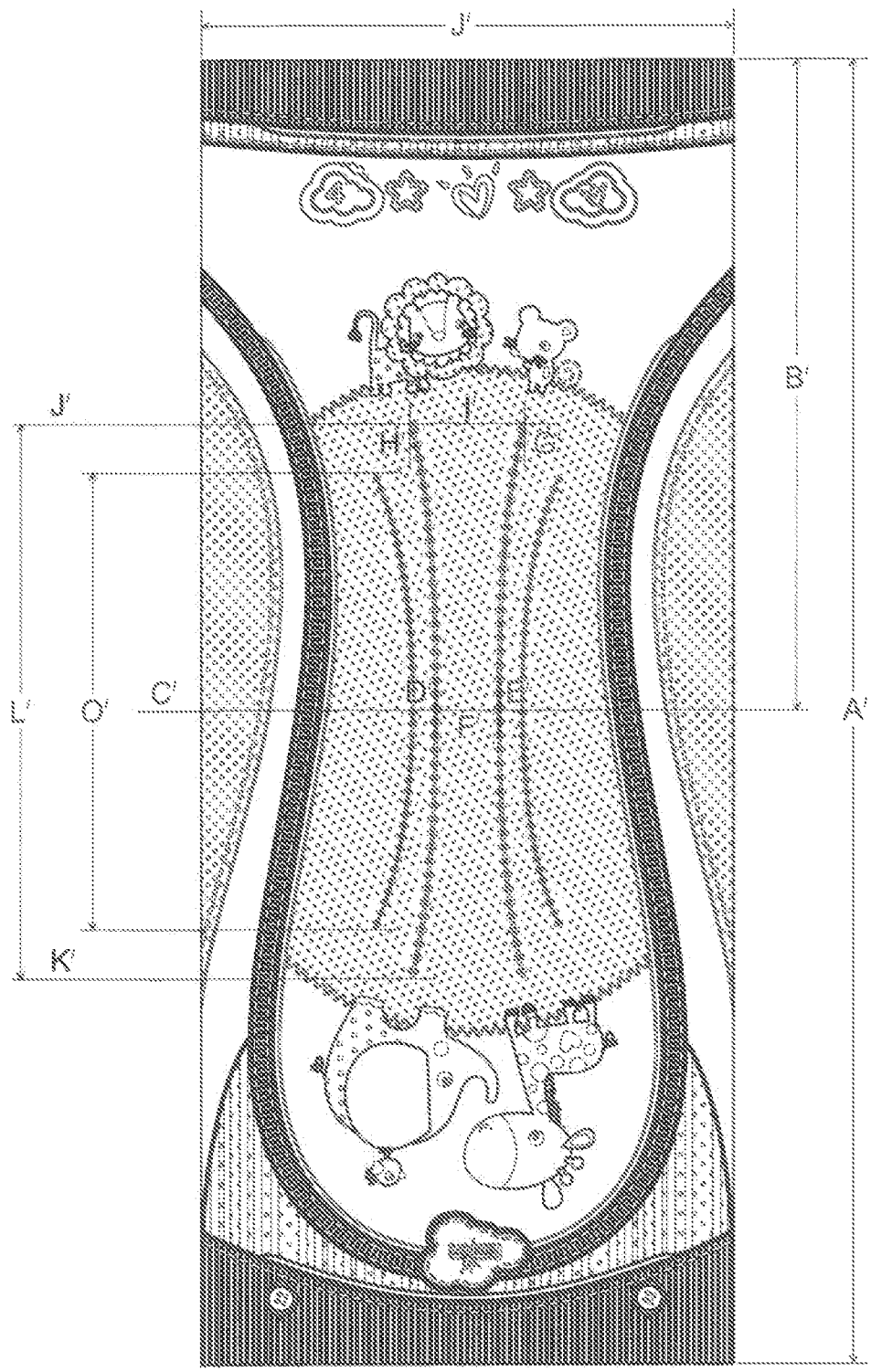
FIG. 19 shows a plan view of backsheet graphics that approximate the shape and contours of the channels.

As shown in FIG. 19, backsheet graphics that approximate the shape and contours of the channels may be arranged such that they fit within the absorbent core area of the absorbent article without extending beyond such area, thereby providing a caregiver a clearer communication of the benefits of the channels. An exemplary backsheet containing graphics that approximate the shape and contours of the underlying channels is depicted. The length A' of the backsheet in the machine direction may be, e.g. 478 mm, and its width P' in the cross-direction may be 196 mm. A centerline in the machine direction of the backsheet is shown by Line C', and thus the half length B' is 239 mm. The distance between the graphics that visually signal the inner channels is shown as the distance F' between lines D' and E', taken along centerline C'. The distance F' may be 22 mm. The distance between the graphics that visually signal the outer channels is shown as the distance I' between lines G' and H', taken along Line J'. The distance I' may be 37.5 mm. Lines J' and K' are drawn parallel to centerline C' and are taken along the terminating points of the graphics visually signaling the inner channels, termination referring to the points at which the graphics end, starting from centerline C'. The distance between these terminating points, in the machine direction is shown by Line L'. This distance may be 198 mm. Lines M' and N' are drawn parallel to centerline C' and are taken along the terminating points of the graphics visually signaling the outer channels, termination referring to the points at which the graphics end, starting from centerline C'. The distance between these terminating points, in the machine direction is shown by Line 0'. This distance may be 158 mm. The distance between the graphics visually signaling the inner channels and graphics visually signaling the outer channels, taken along Line C', may be 6 mm. In a preferred embodiment, where all lengths are given in mm: A'=478; P'=206; L'=205; O'=165; I'=43; and F'=22.

The relative lengths of any of the lines above may be expressed as ratios, and may be exact, or may be expressed with a tolerance of plus or minus 2%, 3%, 4%, 5%, 7%, or 10%, alone or in combination with other ratios of lengths, and the length may be rounded to the nearest whole number or multiple of 5, after the percent of tolerance is applied.

Applicants have found that ratios particularly important in signaling one or more benefits of the channels are those of: (a) A' to L'; (b) B' to L'; and (c) P' to F'. In some embodiments: the A' to L' ratio will range from 2.2 to 2.7, preferably from 2.3 to 2.5, more preferably it will be 2.4. In some embodiments: the B' to L' ratio will range from 1.0 to 1.4, preferably from 1.1 to 1.3, more preferably it will be 1.2. In some embodiments: the P' to F' ratio will range from 8.0 to 9.8, preferably from 8.5 to 9.4, more preferably it will be 8.9.

Further, in some embodiments, the graphics visually signaling the inner channels will not extend beyond the area of the outer channels themselves, and/or the area where the absorbent core is present, and in some embodiments, the graphics visually signaling the outer channels will not extend beyond the area of the outer channels themselves, and/or the area where the absorbent core is present, and in some embodiments, the graphics visually signaling the inner and outer channels will not extend beyond the area of the inner and outer channels themselves, and/or the area where the absorbent core is present.

In addition, the article may comprise other or additional visual cues that signal the absorbent core channels, such as, for example, embossing. Embossing may be done on the topsheet or on the absorbent core, or, in some embodiments, there may be multi-layer embossing of both the topsheet and the absorbent core. For example, thermal embossing may be done over the channels (where there is no superabsorbent polymer) at a small gap setting to enhance the visual presence. Any embossing may be done alone or in combination with printing to help signal the absorbent core channels. Further, any embossing may be done to the topsheet, core, or both, on-line (during assembly of the absorbent article's component parts) or prior to such assembly, e.g. at the site where a supplier of component parts makes the component part itself.

In some embodiments, the printed adhesive layer or the backsheet printing may be a pattern that covers the majority or even all of the absorbent core. In other embodiments, the printed adhesive layer or backsheet printing may be printed only in discrete areas. For example, in some embodiments, the printed adhesive layer or backsheet printing may be printed so as to not overlap or intersect with the absorbent core channels. The term "overlap" as used herein means to cover over a part of, or to have an area in common. The term "intersect" as used herein means items that cut across or through each other, or that narrow and merge.

In order to ensure that absorbent article components (including graphic absorbent article components) are properly oriented when attached to other absorbent article components, registration may be used. Registration may include using a system to detect a location on an absorbent article component and to compare the location against a set point (which may be an operator desired or machine set location). The system may adjust placement of the absorbent article component in accordance with said comparison. For example, the location of absorbent core channels and a printed adhesive layer may be detected and a repeat length of the printed adhesive layer may be altered via a length control system (described in U.S. Pat. Nos. 6,444,064 and 6,955,733). Alternatively, a system may be used to detect and control the longitudinal or machine direction position of a component relative to a desired position on the absorbent article wherein the position at which subsequent occurrences of a first component is attached to a second component is altered to ensure the first component is in the desired location. Such can be performed based on multiple detections and the use of an averaging position, deviation from the desired position, or by detecting less frequently than every occurrence. Additionally, a system may detect a first location on a first absorbent article component and a second location on a second absorbent article component, where the first and second locations may be compared relative to each other and against a set point or desired offset position. The system may adjust placement of the first and/or second absorbent article components in accordance with said comparison. Combinations of detection methods may be used.

In some embodiments, registration may be used to optimize the visual impression of the printing and the absorbent core channels.

In some embodiments, any printing, whether a printed adhesive layer, a backsheet graphic, or some combination, may match, or substantially match the shape or contour of the absorbent core channels. In some embodiments, the printing will not necessarily match or correlate with the shape or contour of the absorbent core channels, but will otherwise communicate or signal to the consumer the existence and/or benefits of the channels.

Absorbent Articles, e.g. Diapers

The absorbent structure (13) or absorbent core (7) herein may be useful in an absorbent article, such as described above, and in particular in a diaper (1), including fastenable diapers (1) and (refastenable) training pants, for infants or for adults, or in an absorbent pad, such as a sanitary napkin or adult incontinence undergarment pad.

The article may comprise, in addition to an absorbent structure (13) or absorbent core (7) as described herein, a topsheet and backsheet, and for example one or more side flaps or cuffs. The topsheet or cuffs or side flaps may comprise a skin care composition or lotion or powder, known in the art, panels, including those described in U.S. Pat. Nos. 5,607,760; 5,609,587; 5,635,191; U.S.

Articles herein comprise a topsheet, facing the wearer in use, for example a nonwoven sheet, and/or an apertured sheet, including apertured formed films, as known in the art, and a backsheet.

The backsheet may be liquid impervious, as known in the art. In some embodiments, the liquid impervious backsheet comprises a thin plastic film such as a thermoplastic film having a thickness of about 0.01 mm to about 0.05 mm. Suitable backsheet materials comprise typically breathable material, which permit vapors to escape from the diaper (1) while still preventing exudates from passing through the backsheet. Suitable backsheet films include those manufactured by Tredegar Industries Inc. of Terre Haute, IN and sold under the trade names X15306, X10962 and X10964.

The backsheet, or any portion thereof, may be elastically extendable in one or more directions. The backsheet may be attached or joined to a topsheet, the absorbent structure/core, or any other element of the diaper (1) by any attachment means known in the art.

Diapers herein may comprise leg cuffs and/or barrier cuffs; the article then typically has a pair of opposing side flaps and/or leg and/or barrier cuffs, each of a pair being positioned adjacent one longitudinal side of the absorbent structure/core, and extending longitudinally along said structure/core, and typically being mirror images of one another in the longitudinal-axis of the article; if leg cuffs and barrier cuffs are present, then each leg cuffs is typically positioned outwardly from a barrier cuff. The cuffs may be extending longitudinally along at least 70% of the length of the article. The cuff(s) may have a free longitudinal edge that can be positioned out of the X-Y plane (longitudinal/transverse directions) of the article, i.e. in z-direction. The side flaps or cuffs of a pair may be mirror images of one another in the longitudinal axis of the article. The cuffs may comprise elastic material.

The diapers herein may comprise a waistband, or for example a front waistband and back waist band, which may comprise elastic material.

The diaper (1) may comprise side panels, or so-called ear panels. The diaper (1) may comprise fastening means, to fasten the front and back, e.g. the front and back waistband. Fastening systems may comprise fastening tabs and landing zones, wherein the fastening tabs are attached or joined to the back region of the diaper (1) and the landing zones are part of the front region of the diaper (1).

The absorbent structure (13) may be combined with, and the absorbent core (7) or diaper (1) may comprise, an acquisition layer (12) and/or acquisition material layer (70), or system thereof this may comprise chemically cross-linked cellulosic fibers. Such cross-linked cellulosic fibers may have desirable absorbency properties. Exemplary chemically cross-linked cellulosic fibers are disclosed in U.S. Pat. No. 5,137,537. In certain embodiments, the chemically cross-linked cellulosic fibers are cross-linked with between about 0.5 mole % and about 10.0 mole % of a $C_2$ to $C_9$ polycarboxylic cross-linking agent or between about 1.5 mole % and about 6.0 mole % of a $C_2$ to $C_9$ polycarboxylic cross-linking agent based on glucose unit. Citric acid is an exemplary cross-linking agent. In other embodiments, polyacrylic acids may be used. Further, according to certain embodiments, the cross-linked cellulosic fibers have a water retention value of about 25 to about 60, or about 28 to about 50, or about 30 to about 45. A method for determining water retention value is disclosed in U.S. Pat. No. 5,137,537. According to certain embodiments, the cross-linked cellulosic fibers may be crimped, twisted, or curled, or a combination thereof including crimped, twisted, and curled.

In a certain embodiment, one or both of the upper and lower acquisition layers may comprise a non-woven, which may be hydrophilic. Further, according to a certain embodiment, one or both of the upper and lower acquisition layers may comprise the chemically cross-linked cellulosic fibers, which may or may not form part of a nonwoven material. According to an exemplary embodiment, the upper acquisition layer may comprise a nonwoven, without the cross-linked cellulosic fibers, and the lower acquisition layer may comprise the chemically cross-linked cellulosic fibers. Further, according to an embodiment, the lower acquisition layer may comprise the chemically cross-linked cellulosic fibers mixed with other fibers such as natural or synthetic polymeric fibers. According to exemplary embodiments, such other natural or synthetic polymeric fibers may include high surface area fibers, thermoplastic binding fibers, polyethylene fibers, polypropylene fibers, PET fibers, rayon fibers, lyocell fibers, and mixtures thereof. Suitable nonwoven materials for the upper and lower acquisition layers include, but are not limited to SMS material, comprising a spunbonded, a melt-blown and a further spunbonded layer. In certain embodiments, permanently hydrophilic non-wovens, and in particular, nonwovens with durably hydrophilic coatings are desirable. Another suitable embodiment comprises a SMMS-structure. In certain embodiments, the nonwovens are porous.

The diaper (1) may include a sub-layer disposed between the topsheet and the absorbent structure (13)/absorbent core (7), capable of accepting, and distributing and/or immobilizing bodily exudates. Suitable sublayers include acquisition layers, surge layers and or fecal material storage layers, as known in the art. Suitable materials for use as the sub-layer may include large cell open foams, macro-porous compression resistant non woven highlofts, large size particulate forms of open and closed cell foams (macro and/or microporous), highloft non-wovens, polyolefin, polystyrene, polyurethane foams or particles, structures comprising a multiplicity of vertically oriented, looped, strands of fibers, or apertured formed films, as described above with respect to the genital coversheet. (As used herein, the term "microporous" refers to materials that are capable of transporting fluids by capillary action, but having a mean pore size of more than 50 microns. The term "macroporous" refers to materials having pores too large to effect capillary transport of fluid, generally having pores greater than about 0.5 mm (mean) in diameter and more specifically, having pores greater than about 1.0 mm (mean) in diameter, but typically less than 10 mm or even less than 6 mm (mean).

Processes for assembling the absorbent article or diaper (1) include conventional techniques known in the art for constructing and configuring disposable absorbent articles. For example, the backsheet and/or the topsheet can be joined to the absorbent structure/core or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minnesota under the designation HL-1258 or H-2031. While the topsheet, the backsheet, and the absorbent structure (13)/core may be assembled in a variety of well-known configurations, diaper (1) configurations are described generally in U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

Method of Making the Absorbent Structure (13)

The absorbent structure (13) herein may be made by any method comprising the step of depositing absorbent material (50) onto a supporting sheet (16), for example by pacing first said supporting sheet (16) onto raised portions in the shape and dimensions of said channels (26) to be produced and then depositing said absorbent material (50) thereon; thereby, the absorbent material (50) does not remain onto said raised portions, but only on the remaining portions of the supporting sheet (16).

In some embodiments, the absorbent structure (13) with the absorbent layer (17) with therein two or more channels (26) with substantially no absorbent material (50) is for example obtainable by a method comprising the steps of:

a) providing a feeder for feeding said absorbent material (50) to a first moving endless surface, such as a hopper;
b) providing a transfer means for transferring a supporting sheet (16) to a second moving endless surface;
c) providing a first moving endless surface, having one or more absorbent layer (17)-forming reservoirs with a longitudinal dimension and averaged length, a perpendicular transverse dimension and average width, and, perpendicular to both, a depth dimension and average depth, and a void volume for receiving said absorbent material (50) therein, said reservoir(s) comprising one or more substantially longitudinally extending raised strips, not having a void volume, for example each having an average width W of at least 4% or at least 5% of the average width of the reservoir, and an average length L of at least 5% and at the most 30% of the average longitudinal dimension of the reservoir; said reservoir(s) being for transferring said absorbent material (50) to said second moving endless surface adjacent and in proximity thereto
d) providing a second moving surface, having an outer shell that has one or more air permeable or partially air permeable receptacles with for receiving said supporting sheet (16) thereon or therein, with a receiving area and with one or more substantially longitudinally extending mating strips that may be air impermeable, and having each an average width of for example W' of at least 2.5 mm, from 0.5×W to 1.2×W, an average length of for example L' being from about 0.8×L to 1.2×L;

whereby said air-permeable outer shell is connected to one or more secondary vacuum systems for facilitating retention of supporting sheet (16) and/or said absorbent material (50) thereon, and whereby, in a meeting point, said first moving endless surface and said outer shell are at least partially adjacent to one another and in close proximity of one another during transfer of said absorbent material (50) and such that each mating strip is substantially completely adjacent and in close proximity to a raised strip during transfer of said absorbent material (50);

e) feeding with said feeder an absorbent material (50) to said first moving endless surface, in at least said reservoir (s) thereof;

f) optionally, removing any absorbent material (50) on said raised strips (s);

g) simultaneously, transferring said supporting sheet (16) to said second moving endless surface, onto or into said receptacle(s);

h) selectively transferring in said meeting point, said absorbent material (50) with said first moving endless surface only to said part of the supporting sheet (16) that is on or in said receiving area of said receptacle; and i) 1) applying an adhesive material (i.e. a first adhesive material (40)) to said absorbent structure (13) of step g; and/or i) 2) applying an adhesive material (i.e. a second adhesive material (60)) to said supporting sheet (16), prior or step f, or simultaneously therewith, but in any event prior to step g).

Step i) 1) may involve spraying said first adhesive material in the form of fibers onto said absorbent layer (17), or part thereof, for example substantially continuously, so it is also present in said channels (26).

Step i) 2) may involve slot coating or spray-coating the supporting sheet (16), either continuously, or for example in a pattern corresponding to the channel (26) pattern.

Said reservoir(s) may be formed by of a multitude of grooves and/or cavities with a void volume, for receiving said absorbent material (50) therein. In some embodiments, the average width W of (each) strip may be at least 6 mm, or for example at least 7 mm, and/or at least at least 7%, or for example at least 10% of the average width of the respective reservoir.

Said grooves and/or cavities may each for example have a maximum dimension in transverse direction which is at least 3 mm, and whereby the shortest distance between directly neighboring cavities and/or grooves in substantially transverse dimension, is less than 5 mm. Cavities and/or grooves that are directly adjacent a raised strip may have a volume that is more than the volume of one or more, or all of their neighboring cavities or grooves, that are not directly adjacent said strip or another strip (thus further removed from a strip).

Said first moving endless surface's reservoir may be at least partially air permeable and said first moving endless surface may have a cylindrical surface with said reservoirs, rotatably moving around a stator, comprising a vacuum chamber; said second moving surface's outershell may be cylindrical, rotatably moving around a stator, comprising a secondary vacuum chamber connected to said secondary vacuum system.

The method may be to produce an absorbent core (7) or structure that comprises two or more of the above described absorbent structures (13;13'); for example two such layers, superposed on one another such that the absorbent material (50) of a first layer and the absorbent material (50) of the other second layer are adjacent one another and sandwiched between the supporting sheet (16) of the first layer and the supporting sheet (16) of the second layer.

The method may involve the provision of a pressure means, such as a pressure roll, that can apply pressure onto the absorbent structure (13), and typically an absorbent structure (13) whereby the absorbent material (50) is sandwiched between the supporting sheet (16) a further material; the pressure may be applied onto said supporting sheet (16) or on any of the further material/layer that placed over the absorbent layer (17), as described above in this section. This pressure application may be done to selectively apply pressure only onto the channels (26 and/or 26') of the absorbent structure (13), e.g. on the portions of the supporting sheet (16) that correspond to the channels (26), and that thus not comprise (on the opposed surface) absorbent material (50), to avoid compaction of said absorbent material (50) itself and/or on the portions of the further material, e.g. the supporting sheet (16') thereof, that correspond to the channels (26'), and that thus not comprise (on the opposed surface) absorbent material (50), to avoid compaction of said absorbent material (50) itself.

Thus, the pressure means may have a raised pressuring pattern corresponding to said pattern of the raised strip(s) and/or of said mating strip(s), in some corresponding to the pattern of the mating strip(s).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
    a central longitudinal axis and a central longitudinal strip, coinciding with the central longitudinal axis;
    a topsheet, a backsheet, an absorbent core disposed between the topsheet and the backsheet, and an acquisition layer disposed between the topsheet and the absorbent core;

wherein the absorbent core has a supporting sheet and comprises a channel, wherein the supporting sheet in the channel is bonded such that the supporting sheet is present on a longitudinal wall of the channel;

wherein the central longitudinal strip is free of the channel;

wherein the topsheet or the backsheet has printing; and wherein the channel and the printing do not overlap.

2. The absorbent article of claim 1, wherein the printing is of a fluid, the fluid being an ink and substantially free, or free, of adhesive.

3. The absorbent article of claim 1, wherein the printing is of a fluid, the fluid being an adhesive and substantially free, or free, of ink.

4. The absorbent article of claim 1, wherein the printing is of a fluid, the fluid being a mixture of adhesive and ink.

5. The absorbent article of claim 1, wherein the printing is of a fluid, the fluid being an ink, and the printing being performed using digital printing.

6. The absorbent article of claim 1, wherein the acquisition layer has a surface that is adjacent to the absorbent core.

7. The absorbent article of claim 1, wherein the printing is on the backsheet.

8. The absorbent article of claim 1, wherein the printing is on the topsheet.

9. The absorbent article of claim 1, comprising a second channel, and wherein the channel and the second channel are mirror images of one another with respect to the central longitudinal axis.

10. An absorbent article comprising:

a central longitudinal axis and a central longitudinal strip, coinciding with the central longitudinal axis;

a topsheet, a backsheet, an absorbent core disposed between the topsheet and the backsheet, and an acquisition layer disposed between the topsheet and the absorbent core;

wherein the absorbent core has a supporting sheet and comprises two channels, wherein the supporting sheet in a portion of the channels is bonded such that the supporting sheet is present on longitudinal walls of the channels;

wherein the central longitudinal strip is free of the channels;

wherein the topsheet or the backsheet has printing; and wherein the channels and the printing do not overlap.

11. The absorbent article of claim 10, wherein the printing is visible through the topsheet or the backsheet.

\* \* \* \* \*